(12) United States Patent
Keck et al.

(10) Patent No.: US 7,346,883 B2
(45) Date of Patent: Mar. 18, 2008

(54) SYSTEM AND METHOD FOR INTEGRATED DATA TRANSFER, ARCHIVING AND PURGING OF SEMICONDUCTOR WAFER DATA

(75) Inventors: Jay Keck, Portland, OR (US); David M. Kallus, Needham, MA (US); Daniel P. Croft, Beaverton, OR (US); Zachary J. Vergow, Norton, MA (US); Daniel K. Kesler, Pawtucket, RI (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 321 days.

(21) Appl. No.: 11/177,702

(22) Filed: Jul. 8, 2005

(65) Prior Publication Data
US 2006/0009942 A1 Jan. 12, 2006

Related U.S. Application Data

(60) Provisional application No. 60/587,001, filed on Jul. 9, 2004.

(51) Int. Cl.
*G06F 17/50* (2006.01)
(52) U.S. Cl. .................. 716/19; 716/20; 716/21; 700/121; 709/201; 709/202; 709/203
(58) Field of Classification Search ............ 716/19–21; 700/96, 121, 173, 179, 180; 709/201–203
See application file for complete search history.

(56) References Cited

U.S. PATENT DOCUMENTS

| | | | |
|---|---|---|---|
| 6,167,358 A | | 12/2000 | Othmer et al. |
| 6,701,259 B2 * | 3/2004 | Dor et al. ..................... 702/35 |
| 6,980,873 B2 * | 12/2005 | Shen ........................ 700/108 |
| 6,990,385 B1 * | 1/2006 | Smith et al. ................ 700/110 |
| 7,123,980 B2 * | 10/2006 | Funk et al. ................. 700/121 |
| 7,218,985 B2 * | 5/2007 | Naya et al. ................. 700/121 |
| 2002/0161532 A1 * | 10/2002 | Dor et al. ..................... 702/35 |
| 2002/0165636 A1 | 11/2002 | Hasan |

\* cited by examiner

*Primary Examiner*—Jack Chiang
*Assistant Examiner*—Nghia M. Doan
(74) *Attorney, Agent, or Firm*—Caven & Aghevli LLC

(57) ABSTRACT

A system for the integrated archiving, restoring, purging, importing and exporting of semiconductor wafer data, the system including a data acquisition system for acquiring scan data from differing types of semiconductor wafer scanning tools such as wafer dimensional tools, wafer inspection tools, and wafer nanotopography tools, a buffer system for providing temporary storage for scan data transmitted over a network from the data acquisition system and for providing fault tolerance, a server system for providing storage for the scan data transmitted from the buffer system and converting the scan data into a format used by and stored in a database management system; and an analysis system client station including a display and communicating with the server system over the network, the analysis system and the server system managing the purging, archiving, restoring, importing and exporting of scan data.

25 Claims, 46 Drawing Sheets

Fig. 3

|  | Embodiment 1 | Embodiment 2 | Embodiment 3 |
|---|---|---|---|
| Data Acquisition System: | 5 tools (any combination of defect and dimensional tools) | 10 tools (any combination of defect and dimensional tools) | 25 tools (any combination of defect and dimensional tools) |
| Buffer System: | 5 Buffer Boxes | 10 Buffer Boxes | 25 Buffer Boxes |
| Server System | Dual Xeon CPU Server<br>• 1 TByte Fibre Channel RAID Storage Array<br>• Backup Server & Software<br>• Backup Tape Library<br>• Server Software | Dual Xeon CPU Server<br>• 2 TByte Fibre Channel RAID Storage Array<br>• Backup Server & Software<br>• Backup Tape Library<br>• Server Software | Quad Xeon CPU Server<br>• 5 TByte Fibre Channel RAID Storage Array<br>• Backup Server & Software<br>• Backup Tape Library<br>• Server Software |
| Data Analysis System (client) | 3 Pentium 4 3.0 Ghz Workstations<br>• 3 Client Software<br>• 3 ReportTools Client Software<br>• 3 WisNT Client Software<br>• Color Laserjet 4600 Printer | 5 Pentium 4 3.0 Ghz Workstations<br>• 5 Client Software<br>• 5 ReportTools Client Software<br>• 5 WisNT Client Software<br>• Color Laserjet 5500 Printer | 10 Pentium 4 3.0 Ghz Workstations<br>• 10 Client Software<br>• 10 ReportTools Client Software<br>• 10 WisNT Client Software<br>• Color Laserjet 5500 Printer |

Fig. 8

| Product | Process | Ingot | Cassette | Wafer |
|---|---|---|---|---|
| Product1 | Lapping | Kjh | Westwood | 0004 |
| Product1 | Lapping | Fdh | Westwood | 0005 |
| Product1 | Lapping | Sjm | Westwood | 0001 |
| Product1 | Lapping | Dgf | Westwood | 0002 |
| Product1 | Lapping | Gfd | Westwood | 0003 |
| Product1 | Lapping | Dgs | Westwood | 0004 |
| Product1 | Lapping | Sdg | Westwood | 0005 |
| Product1 | PostPolish | Sdg | Westwood | 0001 |
| Product1 | PostPolish | Ger | Westwood | 0002 |
| Product1 | PostPolish | Gsf | Westwood | 0003 |
| Product1 | PostPolish | Wff | Westwood | 0004 |
| Product1 | PrePolish | Bsf | Westwood | 0005 |
| Product1 | PrePolish | Gff | Westwood | 0001 |
| Product1 | PrePolish | Sdg | Westwood | 0002 |
| Product1 | PrePolish | Gff | Westwood | 0003 |
| Product1 | PrePolish | Dgs | Westwood | 0004 |

Test Data ▼

Wafers    Layouts    Legend Filter    Legend Filter

Fig. 9

| STIR Sites | | | |
|---|---|---|---|
| STIR Bounds | Count | % | |
| 0.000 – 0.080 | 1 | 0.73 | |
| 0.080 – 0.160 | 14 | 10.22 | |
| 0.160 – 0.240 | 18 | 13.14 | |
| 0.240 – 0.320 | 36 | 26.28 | |
| 0.320 – 0.400 | 14 | 10.22 | |
| 0.400 – 0.480 | 16 | 11.68 | |
| 0.480 – 0.560 | 8 | 5.84 | |
| 0.560 – 0.640 | 5 | 3.65 | |
| 0.640 – 0.720 | 5 | 3.65 | |
| 0.720 – INF | 20 | 14.60 | |

○ Wafers    Layouts    Legend Filter 34    Legend Filter 36

Fig. 14

| X vs. Y Data | |
|---|---|
| Bins | Count STIR |
| 1 | 1 |
| 0.25 | 123 |
| 0.5 | 207 |
| 0.75 | 117 |
| 1 | 60 |
| 1.25 | 35 |
| 1.5 | 18 |
| 1.75 | 11 |

Properties  Attributes  Data  Views  Tasks

| Task Name | Start | Finish | Status | Progress | Canceled |
|---|---|---|---|---|---|
| Loading | 8/24/01 3:32:43PM | 8/24/01 3:32:46PM | Loaded 150 records | 100% | ☐ |
| Initializing Wafermap | 8/24/01 3:33:42PM | 8/24/01 3:35:05PM | Graph Initialized | 100% | ☐ |
| Initialize Chart | 8/24/01 3:33:42PM | 8/24/01 3:35:07PM | Chart Rendered | 100% | ☐ |
| Compositing Dataset row | 3:33:42PM 3:33:42PM | 3:35:05PM 3:35:07PM | Composite Operation Completed | 100% | ☐ |

Properties  Attributes  Data  Views  Tasks  Log 56  58  60

3D Surface Contour

Cross Section

Defect Rings

Defect Sectors

3D Z-Scale set to 0.200

3D Z-Scale set to 1.00

Fig. 41

General

Elect a recipe or edit the current recipe fields, parameters and set selections. Press 'Commit' to save the edited recipe to the server, or 'Reset' to reset the current recipe.

- 254, 250, 260
- Name: r0 ▼ | Name... | New
- ☐ Hidden  ☐ Draft | Parameters...
- Description: Recipe created from CR8X recipe <05WATEST.RCP> and <GRADE.GRD>. | Tool Signature Files..
- 256
- Copy...
- 252
- Wafer Diameter: 200mm ▼ | Delete...
- 258

Configuration Sets

- 260
- Bin Set: bD ▼
- 262
- Bin Status Set: None ▼
- 264
- Calibration Set: None ▼
- 266
- Exclusion Zone Set: xO ▼
- 270
- Edit Sets...
- 272

274 — Commit | Reset

Fig. 42

| Recipe Name | Recipe Path |
|---|---|
| 2mmFQA | \\ADEYES-WA2K\Data\DemoDB\2mmFQA.rpt |
| 3mmFQA | \\ADEYES-WA2K\Data\DemoDB\3mmfqa.rpt |
| ICQA | \\ADEYES-WA2K\Data\DemoDB\ICQA.setup |
| THKQA2 | \\ADEYES-WA2K\Data\DemoDB\THKQA2.setup |

[ New... ] [ Edit... ] [ Delete ]

Dimensional Recipe                                      X

Recipe Name: [ THKOA2.setup ]

Recipe Path: [ \\ADEYES-WA2K\Data\DemoDB\THKQA2.setup ]  [...]

[ OK ]   [ Cancel ]

| Fvconfig – [Console Root\Fabvision Servers\(local)\Fabvision Databases\DEMODB\Purge Data] | | | | | | | | | -- | X |
|---|---|---|---|---|---|---|---|---|---|---|
| Console | | Window | Help | | | | | | | |
| Product | Process | User Scan | Lot | Wafer | Data base Rec. Age In | Scan File Age In Days | Thumbnail File Age In Days | Temp File Age In Days | Archive File Age In Days | |
| Prod1 | Post Polish | * | * | * | 20 | 10 | 20 | 0 | 0 | |
| Prod1 | Post Polish | * | * | * | 20 | 10 | 20 | 0 | 0 | |

Select Data Type: All

New Mask 280     Edit Mask 282     Delete Mask 284

Purge Frequency

☑ Automatically Perform Purge
Every 7 days
At: 12:00:00 AM

Purge Now

Save

Drive Capacity Monitor

Select Drive Letter: C:\

Notification email: admin@fab.com

Max % Threshold: 100

Save 288     286

FIG. 45

| Edit/New Purge Mask | X |

Product | Process | Lot | Wafer | UserScan

Enter Age for Database Purge
(0 Disables Purge)
Older than: 0 days

Enter Age for Scan File Purge
(0 Disables Purge)
Older than: 0 days

Enter Age for Thumbnail File Purge
(0 Disables Purge)
Older than: 0 days

File Extension to Purge
All ▼

Enter Age for Archived File Purge
(0 Disables Purge)
Older than: 0 days

Enter Age for Temp File Purge
(0 Disables Purge)
Older than: 0 days

Save | Cancel

Fig. 47

| Fvconfig – [Console Root\Fabvision Servers\(local)\Fabvision Databases\DEMODB\Purge/Archive Data | -- | X |
|---|---|---|
| Console　　Window　　Help | -- | X |

Action　　View → ☐ ☐ ☐ ☐

Tree　　　　　304

Console Root
　Fabvision Servers
　　(local)
　　　Fabvision Databas
　　　　DEMODB
　　　　　Task Queue
　　　　　Users
　　　　　Directory Setup
　　　　　Tool Configurati
　　　　　Purge/Archive D
　　　　　Backup
　　　　　Defect Recipes
　　　　　Log Viewer
　　　　　SQM Recipes
　　　　　Configure Fab K
　　　　　Report Maintene
　　　　　Dimensional Rec
　　　NewDB

| Mask Type | Product | Process | UserScan | Lot | Wafer |
|---|---|---|---|---|---|
| Archive Purge | Product2 CSV | Lapping Post | 001 * | ABC * | 00002 * |

| Data base Rec. Age in days | Scan File Age in days | Thumbnail File Age in days | Temp File Age in days | Archive File Age in days | Archive Path 306 |
|---|---|---|---|---|---|
| 600 | 0 | 0 | 0 | 0 | c:\Fabvision\A |
| 100 | 100 | 100 | 0 | 0 | |

Select Mask Type　[All ▼]　　Restore Records Age( days)　[Edit Mask]

New Purge Mask 300　　[55]　　[Delete Mask]

New Archive Mask 302　　＼308

Frequency
☐ Automatically Perform Purge/Archive
Every [55] days
At:
[12:00:00 AM ▲▼]　[Run Now]

Drive Capacity Monitor
Select Drive Letter　　Notification email
[c:\ ▼]　　[dcroft@ade.com]
Max % Threshold　[95]

[Save]　[Cancel]

330

332

SYSTEM AND METHOD FOR INTEGRATED DATA TRANSFER, ARCHIVING AND PURGING OF SEMICONDUCTOR WAFER DATA

CROSS-REFERENCE TO RELATED APPLICATION

The present application claims the benefit of the filing date of U.S. Provisional Patent Application No. 60/587,001, filed Jul. 9, 2004, now abandoned, the entire disclosure of which is incorporated herein by reference.

TECHNICAL FIELD

The present invention is directed to the field of materials processing, and more particularly to a system and method for integrating data transfer, archiving and purging of semiconductor wafer data.

BACKGROUND

The manufacturing of semiconductor wafer and integrated circuits has traditionally employed several types of systems and tools to provide quality control and process monitoring.

For example, wafer geometry systems, ranging from the tabletop gauges to high volume multi-functional sorting systems on state of the art robotic transfer platforms, are used to obtain wafer characterization data to provide an accurate knowledge of wafer dimensional characteristics such as flatness, diameter, thickness, bow, warp, shape, nanotopography, resistivity, background characteristics, thermal shape change, among others. In addition, surface inspection systems are used to identify defects occurring on a surface of a semiconductor wafer, such as particles, scratches, COP's, mounds, dimples, stacking faults, haze and more. Further, certain defect and dimensional analysis systems perform thin film analysis, providing full wafer mapping of surfaces with thin epitaxial film or other dielectric films such as $SiO_2$, CVD, SOI, and photoresist with transition region thickness and substrate carriers.

Software has been developed to analyze the measurement data generated by such systems and transform the data to produce information about process-induced defects, system degradation, and other potential problem areas. Thus, data from dimensional and inspection systems allow process engineers to maintain process control and optimal tool parameters, and provide them with valuable insight when developing new advanced wafer processes.

However, with the wide variety of and large amounts of data from the numerous tools used in the manufacturing of semiconductor wafer and integrated circuits, managing, analyzing and automating wafer data has become extremely complicated. Traditionally, the data generated by the dimensional and inspection systems were treated separately, not combined. In the past, wafer data management and analysis systems have been developed for dimensional systems, but they have not included data from surface inspection systems such as defect evaluation systems. Defect evaluation systems were developed, but they did not support wafer characterization tools or automation features. Because the disparities between the data from the numerous systems, the ability of engineering to use all of the data available to it to optimize manufacturing processes was limited.

In addition, given the large amounts of data developed by each of the numerous tools, it has become apparent that traditional methods of managing older data are inadequate. Analyzing and automating wafer data has become extremely complicated. Further, cross-site transfer of data and review of data from multiple fabrication processes in order to control production across several manufacturing processes, while theoretically possible, was rendered practically difficult by the sheer amount of data and wide variation in types of data to be transferred and reviewed. It would be desirable to provide for transfer of only selective data to a central system to provide multi-plant production management.

Further, the amount of data produced during such production is so great that purging data after a selected interval is necessary in order to make storage room available for new data to be produced. However, some data in a data set could be useful for longer than other data. Traditionally, data purging is conducted by establishing a threshold data and deleting data older than that date. Therefore, it has been necessary to store un-needed data for longer than it was necessary, simply because it was in the same data set as the needed data. It would be desirable to provide a purging system in which data in a data set may be purged as it is no longer needed.

It has become desirable to provide a system for integrated wafer data management and process monitoring system for data management, analysis, and automation from all systems used in the wafer and integrated circuit production process, including both dimensional and inspection systems, along with the software for analyzing such data.

DISCLOSURE AND SUMMARY OF INVENTION

The present invention provides an integrated semiconductor production system for performing wafer data management, process monitoring, data analysis, and data automation, allowing for detailed offline analysis of wafers based on data acquired from both wafer dimensional and surface inspection systems. The integration of wafer data management, process monitoring, data analysis, and data automation for both defect and dimensional tools allows the identification of process-related problems, determination of the origin of those problems, and evaluation of the impact of those problems on manufacturing yields.

The system provides integrated archiving, restoring, purging, importing and exporting of semiconductor wafer data. The system includes a data acquisition system for acquiring scan data from differing types of semiconductor wafer scanning tools such as wafer dimensional tools, wafer inspection tools, and wafer nanotopography tools and also includes a buffer system for providing temporary storage for the scan data transmitted over a network from the data acquisition system and for providing fault tolerance, as well as a server system for providing storage for the scan data transmitted from the buffer system and for converting the scan data into a format used by and stored in a database management system. The system also includes an analysis system operating in client system communicating with the server system over a network so that the analysis system and the server system provide management for purging, archiving, restoring, importing and exporting scan data in one or more locations. The transfer of data can be done manually, using manual archive, restore or purge operations, and the system allows a user to automate archive, restore, and purge operations. The system also enables a user to transfer scan data to different sites for analysis and review, enabling review of scan data from a number of production lots, processes and sites.

The integrated system allows the building of a database of wafer data using the measurement files output by multiple wafer production systems. Querying is provided to create and save datasets using criteria based on metrology values, identification of when the data was acquired or wafer equipment, or process labels. Thumbnail images of and measurement results for specified datasets can be viewed and sorted, the results exported to file, or wafers selected for use in a chart, report or wafer map. Layouts comprising saved sets of setup parameters that define datasets, charts, reports, wafer maps and activities may be saved. Such layouts may be created and shared among multiple system users.

In addition, routine tasks may be automated and conditional operations performed based on measurement results using the Batches feature or the Automated Activities feature. Batches link a named dataset layout with a named report, chart or wafer map layout. The Automated Activities feature comprises a visual macro system in which visual elements created for all of the available layouts, output to printers, status notification and email messages with attachments may be combined to specify a set of actions to be executed. Decisions can be added to the visual elements to allow varying paths of actions to be executed, depending on the outcome of a logical expression based on selected wafer data. Activities may be scheduled for execution at regular intervals or whenever a certain trigger value or label is observed in incoming wafer data.

The integration of wafer data management, process monitoring, data analysis, and data automation into one system allows improved metrology and inspection tool use, allowing for surface inspection and characterization of both thin film devices and bare wafers with the same system. With the system, engineering focus changes from data collection to process optimization. Process excursions are identified more quickly, resulting in reduction in impact of the excursion on work in progress. Report preparation is automated, and paper based quality records are eliminated.

BRIEF DESCRIPTION OF THE DRAWINGS

FIG. 3 is a table showing alternative configurations of the integrated system of the present invention;

FIG. 8 is a block diagram of the Extended Data Mode screen of the Wafers tab of the Utility Window shown in FIG. 4;

FIG. 9 is a block diagram of the Legends Filter tab screen of the Utility Window shown in FIG. 4;

FIG. 14 is a block diagram of a Data tab for the Analysis Window shown in FIG. 4;

FIG. 15 is a block diagram of a Tasks tab for the Analysis Window shown in FIG. 4;

FIG. 41 is a block diagram of a Nanotopography Recipe screen for creating new nanotopography recipes using the Configuration Application system;

FIG. 42 is a block diagram of a screen for the Dimensional Node of the Server System of the Configuration Application system;

FIG. 43 is a block diagram of a selection and specifying screen for selection and specifying dimensional recipes for creation or modification using the Configuration Application system;

FIG. 44 is a block diagram of the main Purge Data graphics user interface screen for the Purge capability of the present invention;

FIG. 45 is a block diagram of the Purge Mask Definition screen for the Purge Data graphics user interface of FIG. 44;

FIG. 47 is a block diagram of the screen showing the tree-view pane of a server configuration, exploded to show the details of the defined Purge/Archive masks for an illustrative embodiment, and for managing the masks;

DETAILED DESCRIPTION OF THE INVENTION

Figure 1:
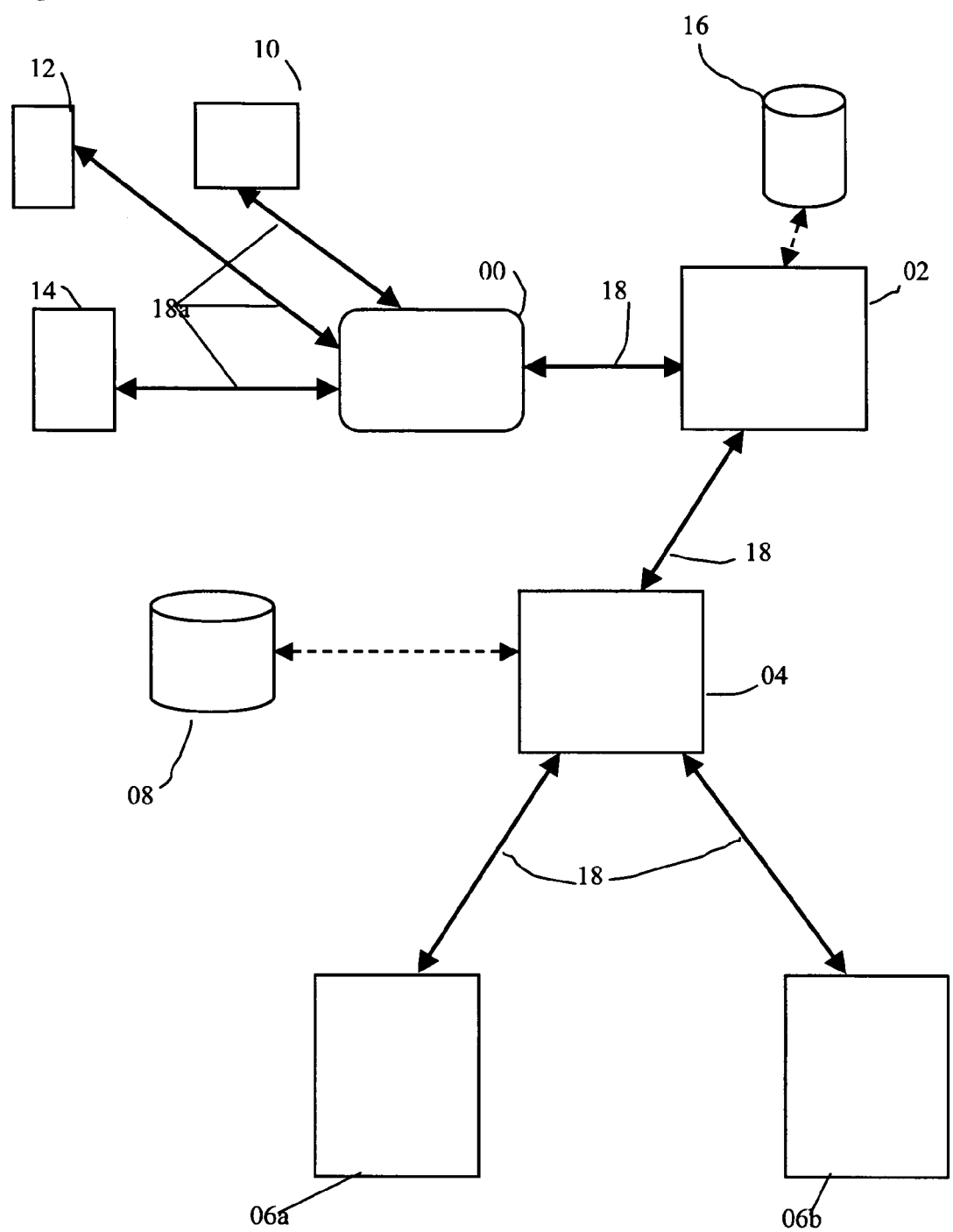
FIG. 1 is a block diagram of the integrated semiconductor wafer data management, process monitoring, data analysis, and data automation system of the present invention.

As seen in FIG. 1, the present invention comprises a data acquisition system 00 for acquiring semiconductor wafer scan data from metrology and inspection tools such as wafer dimensional scanning tool 10, device inspection tool 12 and nanotopography tool 14. Each tool communicates with data acquisition system 00 using its own communications or interface protocol, over a communications path 18a. Data acquisition system 00, in turn, communicates over a communications path 18 with buffer system 02. Buffer system 02 provides temporary storage 16 for scan data transmitted from the wafer scanning tools and also provides fault tolerance features. Still in FIG. 1, buffer system 02 transmits data to server system 04 over communications path 18. Server system 04 provides storage for scan data transmitted by buffer system 02 in a database management system 08. Server system 04 converts the scan data into a format used by data management system 08.

Still in FIG. 1, server system 04 transmits scan data over communications path 18 to one or more analysis systems 06, shown in FIG. 1, as analysis systems client stations 06a and 06b. In the embodiments shown, analysis systems client stations 06a and 06b may be in two different physical locations or in different manufacturing or fabrication plants. Analysis system 06, communicating with server system 04 provides wafer data management, process monitoring, wafer data analysis and data automation. With the system and method of the present invention, users are able to archive, restore, purge, import, and export scan data to and from different locations for review, analysis, and optimization of wafer manufacturing and device fabrication processes. The ability to combine scan data from different tools, locations and processes and transfer it to other locations also makes it possible for users to search for patterns of defects or anomalies in wafers and devices in ways that have not been possible heretofore.

Figure 2:
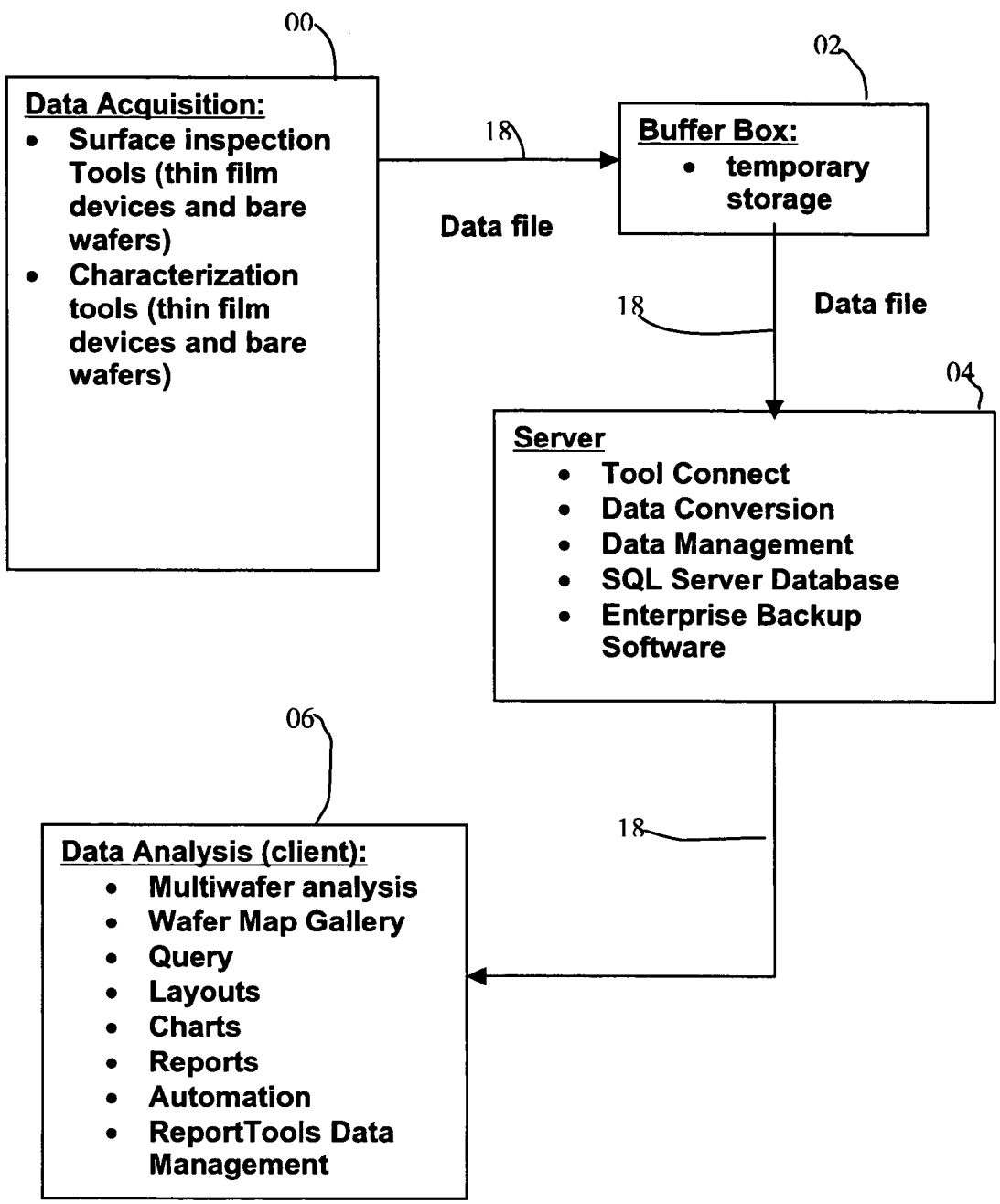
FIG. 2 is a block diagram of the integrated semiconductor wafer data management, process monitoring, data analysis, and data automation system of the present invention.

With reference now to FIG. 2, the integrated semiconductor wafer data management, process monitoring, data analysis, and data automation system of the present invention has the following components, which are connected together using standard networking connections in the embodiments shown:

Data acquisition system 00 contains a comprehensive set of wafer metrology and inspection tools, of both defect and dimensional types. Physically, the data acquisition system 00 is resident in the clean room in the embodiments shown.

Buffer system 02 provides normalization for networking protocols and temporary storage for the tools data from data acquisition system 00. Preferably, the buffer system 02 is also resident in the clean room with the data acquisition system 00. The buffer system 02 may have one Buffer Box for each tool in the data acquisition system 00, or it may have one Buffer Box for the entire tool set. Along with the data acquisition system 00, buffer system 02 forms a tools network that is operable when the server is down. In addition, the temporary storage capability of the buffer system 02 provides a level of fault tolerance, allowing scanning to continue, even if server system 04 is down.

The server system 04 provides storage for data from the tools of the data acquisition system 00. Any time that a data file is input to the server system 04 from the scan of a wafer by a tool, server system 04 converts the tools' data, called in this embodiment a ProcessScan, from the tools' formats to the format used by the data analysis system 06. Server system 04, which may comprise one or more servers, also stores the scan files, using relational database management for main database 08 to facilitate the combination of metrology and inspection tools. Server system 04 has Configuration Application software that provides a unified interface to a set of largely independent server applications. In one embodiment, the server is a computer running Microsoft SQL Server, providing and maintaining a relational database using the SQL language.

Still in FIG. 2, analysis system 06, which is a client system, is software that conducts multi-wafer analysis on the stored scan files. The analysis system 06, in the embodiments shown, preferably comprises multiple desktops linked to the server.

Alternative embodiments of the integrated system of the present invention are shown in FIG. 3. Those skilled in the art will appreciate that database management systems other than those provided by Microsoft Corporation can be used without deviating from the spirit of the present invention. Similarly, various types of networks and computer input/output buses can be used for the communication paths between elements of the present invention without deviating from the spirit of the invention.

Data Analysis System

Analysis system 06 has a user interface with which the system of the present invention can be accessed. The user interface is accessed through a system icon provided on the desktop screen of the computer on which the data analysis system 06 is located.

Note that the data analysis system 06 is a client system in the client/server embodiment shown. While it is not necessary for data acquisition system 00 to be operating in order to operate the analysis system 06, server system 04 must be operating in order to use the data analysis system 06, when these are implemented in client/server methodology. Those skilled in the art will appreciate that the functionality of analysis system 06 and server system 04 can be provided in different ways, including being implemented as one integrated application without deviating from the present invention. In the embodiments shown, if server system 04 is not running properly, a red icon will appear on the lower right corner of the task bar of the computer on which analysis system 06 is located. If a red icon appears, the user may click the icon and perform any instructions, or consult a system administrator. If the Server System is running properly, a green icon will appear. If the user double-clicks on the system icon, the application will load and the main screen will appear.

Each time the integrated system is launched, a user must supply a log-in name and password before the main screen and all of the windows appear.

Log-in Procedure

1. Type the log-in name and password into the appropriate fields.
2. Click the Advanced button.
3. In the Server area of the Login dialog, select the Computer and Database from which wafer records will be obtained for use with the integrated system. The available and appropriate choices will vary depending on the user's system configuration.
4. Click OK.

A user may update a log-in password any time.

User Interface

Figure 4:
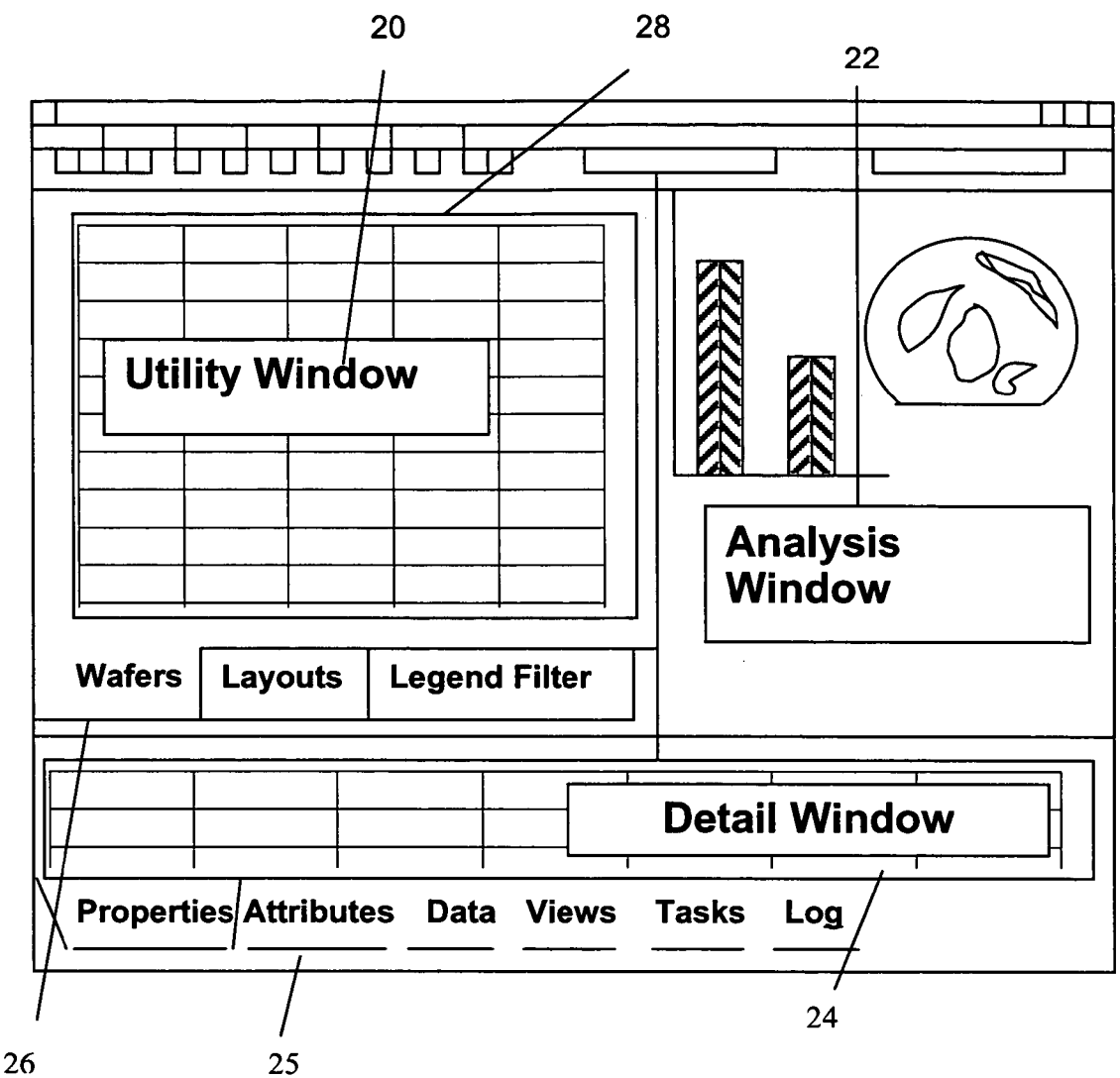
FIG. 4 is a block diagram of the user interface screen of the present invention.

The user interface has three main windows, as shown in FIG. 4.

Utility Window

The Utility Window 20 appears at the upper left of the display shown in FIG. 4. Tabs allow the window display to toggle between wafer data and lists of user-defined "layouts" specifying datasets and outputs (wafer maps, charts, reports). Icons allow toggling among the various report types and specifying whether wafer data values are displayed numerically ("Extended Data" mode) or graphically as thumbnail images ("Gallery" mode).

Analysis Window 22 Display Area

Depending on the information that is currently being displayed, the work area on the right side of the display of FIG. 4 will contain the Wafer Map, Report or Chart Window.

Detail Window 24

Still in FIG. 4, Detail Window 24 appears on the bottom of the display shown in FIG. 4. Tabs allow for toggling between display of wafer properties and data, thumbnail previews of graphical wafer maps, and diagnostic and task status information.

The Utility Window 20

The Utility Window 20 is used to manipulate the wafer maps, reports and charts that are displayed in the Analysis Window 22. The Utility Window 20 includes the Wafers, Layouts and Legends tabs 26.

Wafers Tab

In the Wafers 26 tab, wafer data or thumbnail previews of wafer maps may be viewed, wafers sorted, wafers selected for view in the Analysis Window 22 Display Area, or a single wafer or a group of wafers may be selected to view in the Wafer Display Area. The Wafers 26 tab displays the current wafer dataset in either Classic Gallery Mode, Group Gallery Mode, Multi Dataset Gallery Mode or Extended Data Mode, as described below.

Figure 5:
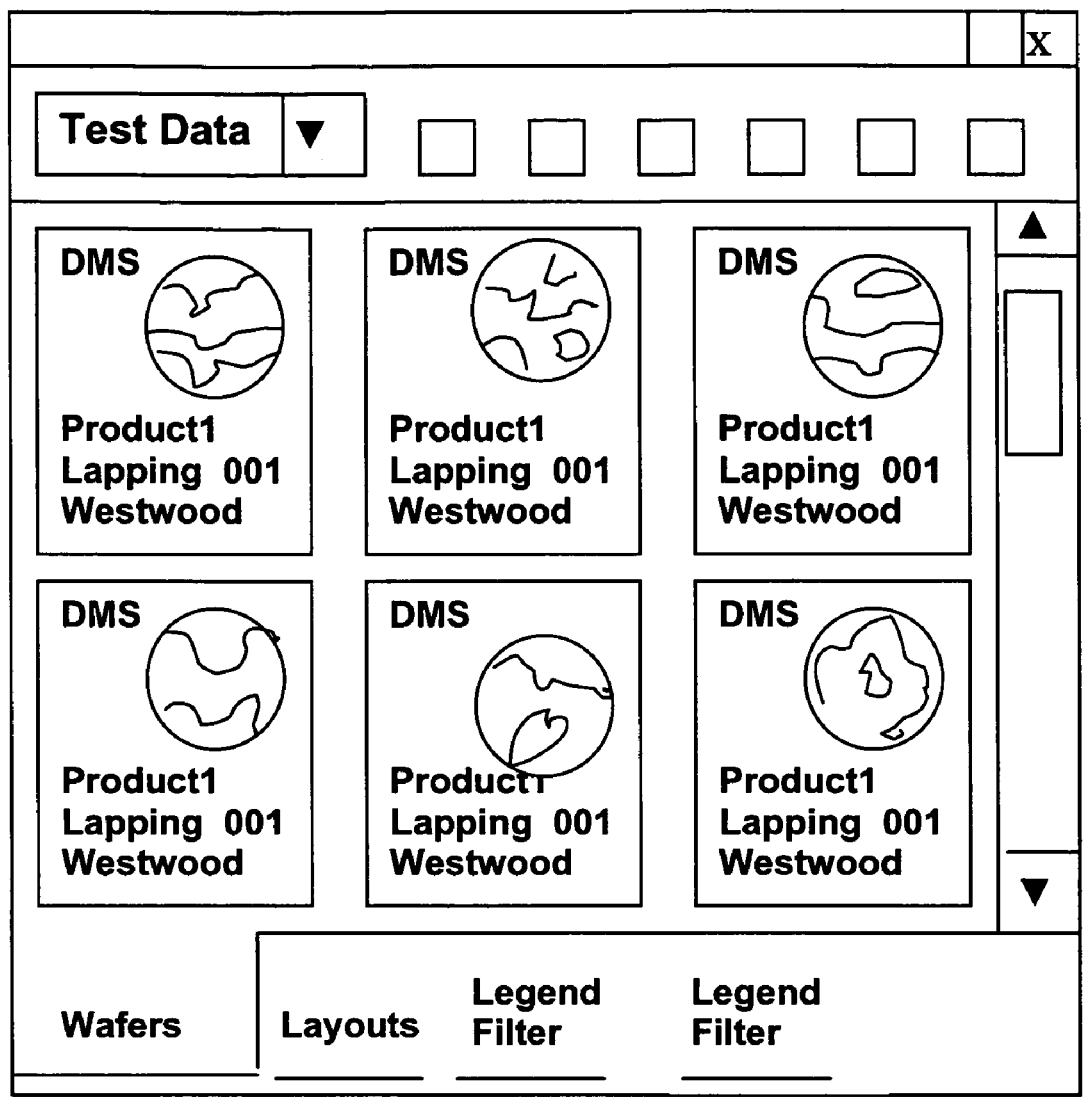
FIG. 5 is a block diagram of the Classic Gallery Mode screen of the Wafers tab of the Utility Window shown in FIG. 4.

As shown in FIG. 5, Classic Gallery Mode displays the dataset as a series of thumbnail images, providing immediate visual representation of the wafer maps within the dataset.

Figure 6:
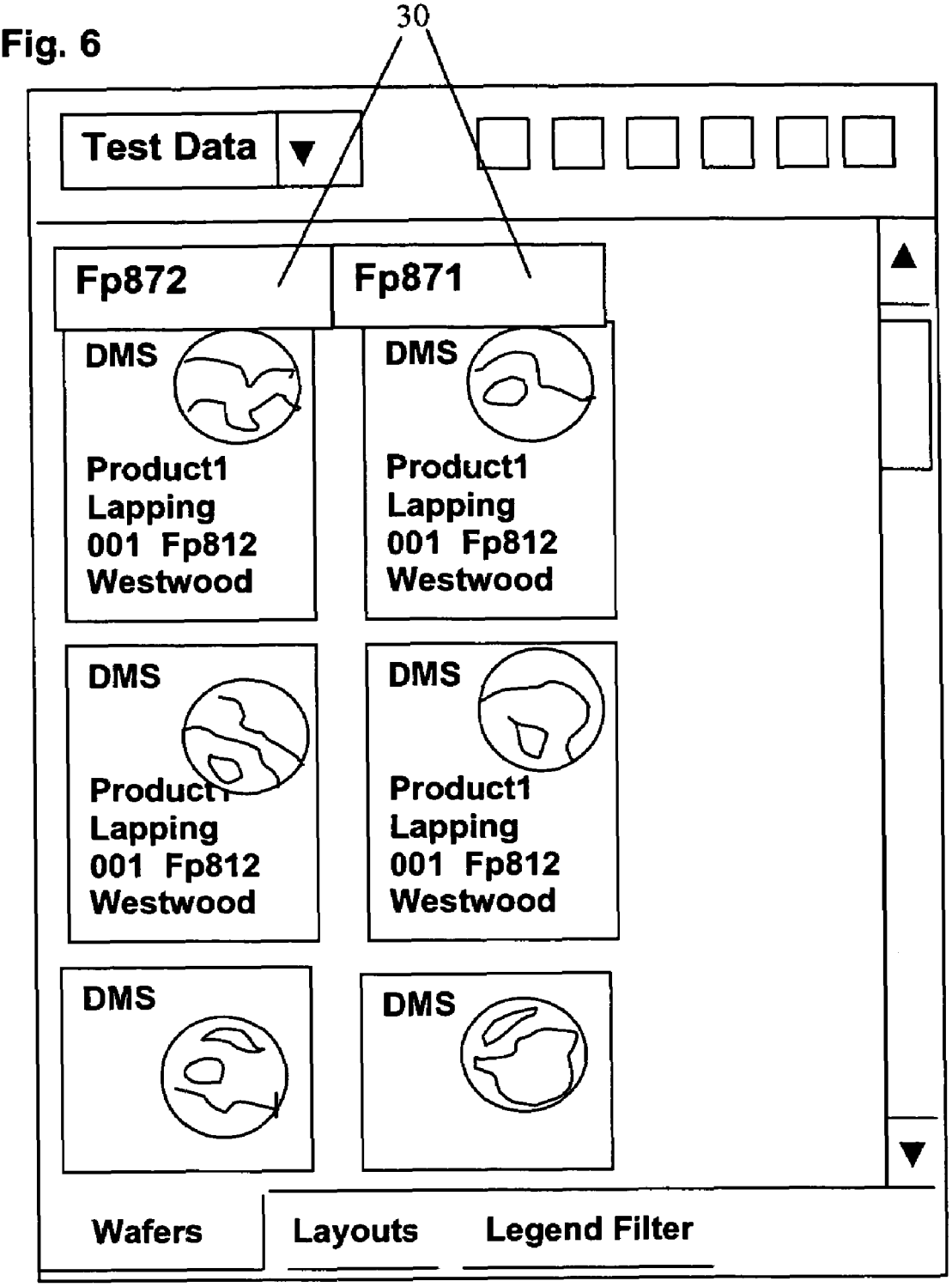
FIG. 6 is a block diagram of the Group Gallery Mode screen of the Wafers tab of the Utility Window shown in FIG. 4.

As seen in FIG. 6, Group Gallery Mode displays the dataset as a series of thumbnail images as in the Classic Gallery, but provides the additional capability of grouping wafers based on a key parameter. A column 30 is created for each unique value for the selected grouping parameter, and wafers are grouped with common values for the selected parameter into the same column.

Figure 7:
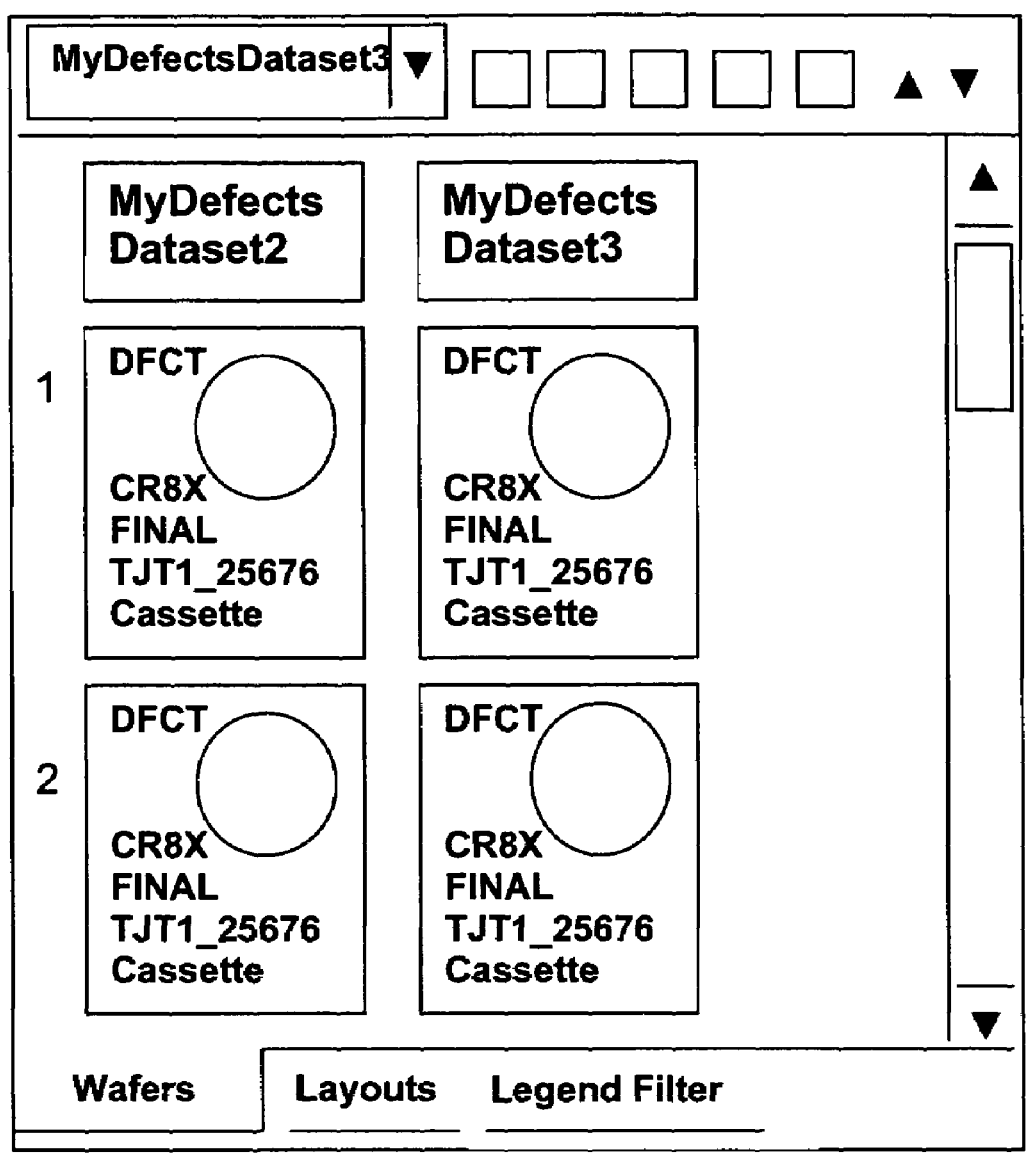
FIG. 7 is a block diagram of the Multi Dataset Gallery Mode screen of the Wafers tab of the Utility Window shown in FIG. 4.

With reference now to FIG. 7, Multi Dataset Gallery Mode displays two or more datasets simultaneously. This can be used as a convenient way of selecting wafers or for correlation between multiple scans using an optional Correlation toolbox.

Turning now to FIG. 8, Extended Data Mode (also called "List" Mode) provides the viewing of data associated with each wafer, in tabular form. This feature can be useful when a user is searching for specific information within a set of wafers. Extended Data Mode also allows sorting the entire dataset according to any included data field 32. In addition, multiple data fields 32 may be used to perform accumulative sorting.

In FIG. 9, The Layouts 34 tab displays lists of user-defined inputs (datasets) and outputs (wafer maps, charts, reports, activities) that are stored in the database. A user may select a layout type to view all of the layout names for that type (as well as who created each layout). From here, a user can view, edit or launch a selected layout.

Still in FIG. 9, The Legend Filter 36 tab displays bin counts and values to assist in interpretation of the currently displayed site, defect density or nanotopography wafer map.

Toolbars and Menus

The Toolbar

The Toolbar contains all of the icons necessary to perform data analysis functions. The toolbar is divided into groups, according to the type of information it will display. Icons are provided for accessing the following functions:

Function:

Create Dataset filters the wafer database according to user-specified date ranges, measurement values and other requirements.

Create Batch allows the building and running of a list of tasks, each pairing a selected dataset layout with a selected wafer map, chart or report layout.

Login/Logout User: Two icons allow a user to log into and out of the application. When a user is logged into the application, the first icon appears grayed out and vice versa.

Open Document displays a wafer map, chart, report or other image or data file generated by the system.

Save saves the layout for the currently displayed item (wafer map, chart, report or activity).

Print prints the currently displayed item.

Email attaches the currently selected item to an email message that a user can preface and distribute as needed.

Cut Cuts the current item.

Copy copies the current item (typically, a wafer map, chart or report) to allow pasting into another application.

Paste pastes a copied item into the selected area

Properties displays the layout settings for the selected wafer map, chart, report or activity.

Options configures which windows and tabs are visible in the user interface. Although most options configured here should generally remain at their factory settings, a user should specify the desired destination for output files in the Options dialog's Directories tab.

Export Document outputs and optionally displays the content of the current wafer map, chart or report as a PDF or CSV file.

Close Window closes the selected Analysis Window item.

Cascade Windows arranges all Analysis Window items such that they are overlapped and all titles display.

Tile Windows arranges all Analysis Window items such that all items are displayed in their entirety but scaled to fit the available Analysis Window size.

Activity Designer Zoom In Used: When editing a complex activity, this allows a user to zoom in to see more detail.

Activity Designer Zoom Out Used: When editing a complex activity, this allows a user to zoom out to see more of the activity's node objects.

Activity Designer Compile converts the activity designer elements to usable code, checking for errors.

Activity Designer Run compiles the current activity, and performs the current activity (if no compile errors are found).

Activity Designer Dataset Node adds a dataset node to the activity being edited. Editing the node properties allows a user to select the desired layout.

Activity Designer Decision Node adds a decision node to the activity being edited.

Activity Designer Report Node adds a report node to the activity being edited. Editing the node properties allows selection of a desired layout.

Activity Designer Chart Node adds a chart node to the activity being edited. Editing the node properties allows selection of a desired layout.

Activity Designer Wafer Node adds a wafer map node to the activity being edited. Editing the node properties allows selection of a desired layout.

Activity Designer Email Node adds an email node to the activity being edited. Editing the node properties allows a user to create a message, define attachments and select recipients.

Activity Designer Printer Node adds a printer node to the activity being edited. Editing the node properties allows selection of an available printer.

Activity Designer Status Node adds a status message node to the activity being edited. Editing the node properties allows a user to customize the popup message.

Menus

Most of the operations that can be performed using the Toolbar are also available from menus on the menu bar of the system screen. There are some operations that can only be accessed from the menus. A brief summary of the menu item functionality follows in the table below:

| File | |
|---|---|
| Create Batch | Builds and runs a list of tasks, each pairing a selected dataset layout with a selected wafer map, chart or report layout. |
| Create Dataset | Filters the wafer database according to user-specified date ranges, measurement values and other requirements. |
| Create Dataset | Displays a wafer map, chart, report or other generated image or data file. |
| Save | Saves the layout for the currently displayed item (wafer map, chart, report or activity). |
| Export | Outputs and optionally displays the content of the current wafer map, chart or report as a PDF or CSV file. |
| Print | Prints the currently displayed item. |
| Send To | Attaches the currently selected item to an email message that a user can preface and distribute as needed. |
| Edit | |
| Undo, Cut, Paste | |
| Copy | Copies the current item (typically, a wafer map, chart or report) to allow pasting into another application. |
| View | |
| Bars & Windows | Several options allow a user to customize the display. |
| Properties | Displays layout settings for the selected wafer map, chart, report or activity. |

-continued

| | |
|---|---|
| Tools | |
| Options | Configures which windows and tabs are visible in the user interface. Although most options configured here should generally remain at their factory settings, a user should specify the desired destination for output files in the Options dialog's Directories tab. |
| Window | |
| Close | Closes the selected Analysis Window item. |
| Close All | Closes all Analysis Window items. |
| Cascade | Arranges all Analysis Window items such that they are overlapped and all titles display. |
| Tile | Arranges all Analysis Window items such that all items are displayed in their entirety but scaled to fit the available Analysis Window size. |

The Analysis Window 22

Figure 10:
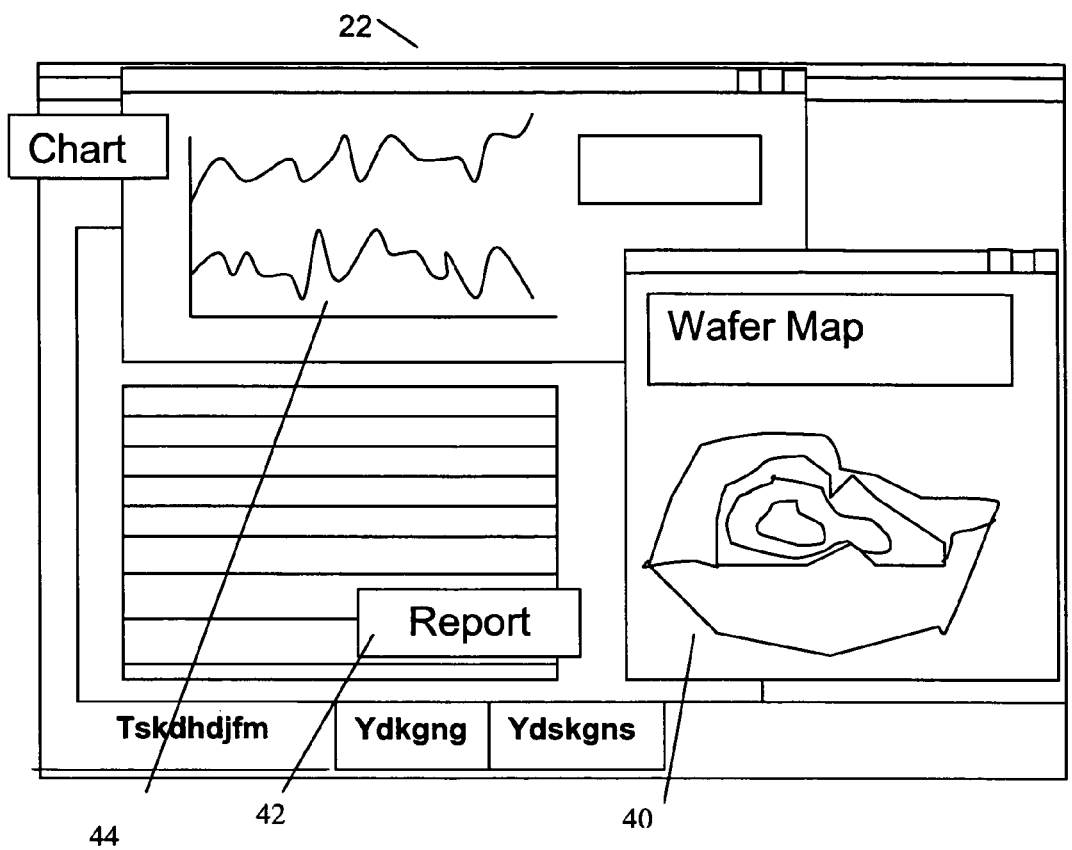
FIG. 10 is a block diagram of examples of screens for reports, charts and wafer map displays in the Analysis Window shown in FIG. 4.
Figure 11:
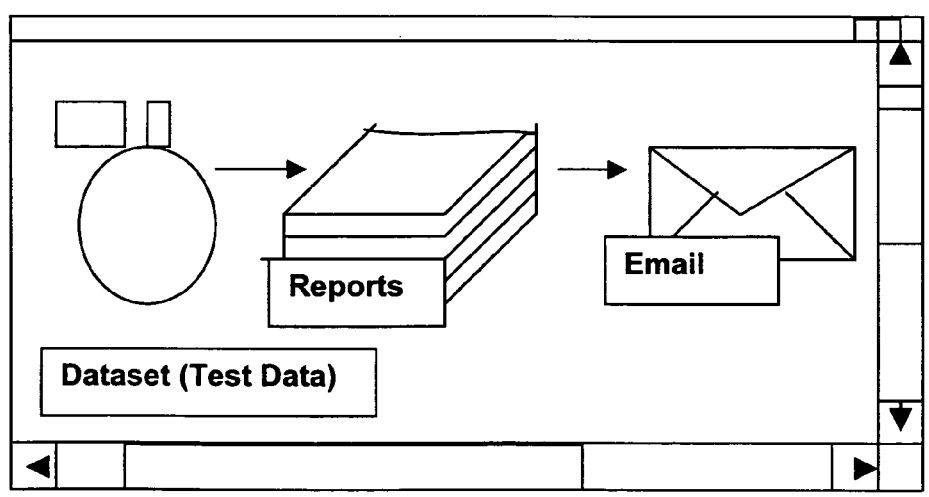
FIG. 11 is a block diagram of a Activities editing screen for the Analysis Window shown in FIG. 4.

Turning now to FIG. 10, the Analysis Window 22 displays the outputs that are generated from the dataset and other selected layouts. It can display wafer maps 40, reports 42 and charts 44 of single wafers, composite wafers, and site flatness distribution. This window is also where a user can edit Activities that automate the creation (and distribution) of datasets, wafer maps, reports and charts.

The Detail Window 24

The Detail Window 24, shown in FIG. 4, at the bottom of the display includes tabs that allow a user to look at specific information pertaining to the current dataset and modify the wafer map display.

Figure 12:
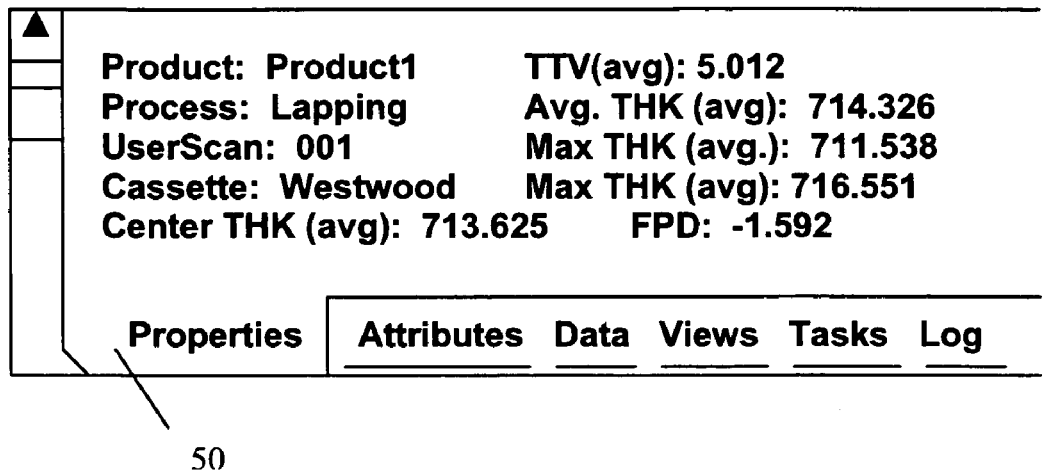
FIG. 12 is a block diagram of a Properties tab for the Analysis Window shown in FIG. 4.

Properties Tab:

The Properties 50 tab, shown in FIG. 12, displays the available information about the wafer currently selected in the Utility window 20 or the item (wafer map, report or chart) currently selected in the Analysis window 22, of FIG. 4.

Attributes Tab

Figure 13:
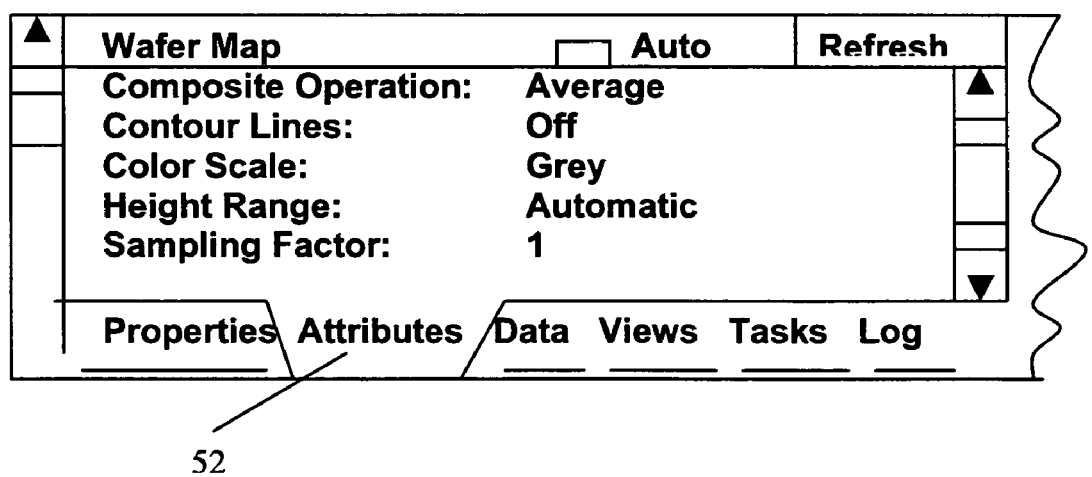
FIG. 13 is a block diagram of an Attributes tab for the Analysis Window shown in FIG. 4.

The Attributes 52 tab, shown in FIG. 13, provides controls allowing a user to change the display properties of the currently displayed wafer map, report or chart.

Data Tab

The Data 54 tab, shown in FIG. 14, provides additional layout information, measurement values or bin values to assist in the interpretation of the currently displayed chart.

Views Tab

The Views 56 tab, shown in FIG. 15, presents thumbnail buttons allowing a user to view the current wafer map using the selected wafer map mode and data selection. Click a button to change the current wafer map.

Tasks Tab

Depending on the number of data files in a database, the location of the files (local or network) and the speed of the computer, many of the system operations may take a while. The Tasks 58 tab of FIG. 15, reports the status of all system operations so that a user knows when actions are completed successfully.

Log Tab

The Log 60 tab of FIG. 15 displays error messages contained in the log file generated by System. Information contained here may be valuable when troubleshooting.

Querying

A Dataset is a collection of wafer data files that will be used to generate wafer maps (graphs), charts and reports. The graphic user interface "GUI" for creating a Dataset is on analysis system 06 in the embodiments shown. A Dataset is created using a query system in which criteria are specified to create a repository of saved wafer dataset layouts, each of which can be edited or used for wafer analysis work.

Dataset layouts, containing the query criteria and display parameters used to generate the datasets, may be saved as layouts, but the resulting dataset cannot be saved or persisted. Dataset layouts are exportable to other users. Query Search eliminates the need to remember where the data is stored.

The definition used to create a dataset includes criteria that specify the following:

when the wafers had to have been measured
required metrology values
various wafer- or process-related information Thus, queries may be based on keys, such as product, lot, tool, operator, cassette, wafer, or User Scan. They can specify a fixed date range (such as wafers created on a specific date, yesterday, last month, within the last n days) or they can specify a relative date range (such as wafers created between to specific dates). Data values (such as COP defect counts or scratch counts above or below a specified number or within a specified range) may be specified in Boolean expressions.

Dataset Dialog

The Create Wafer Dataset, Edit Dataset Layout and New Dataset Layout dialog boxes define criteria determining which wafers will be included in the dataset. This can be based on when the wafer was measured, acceptable wafer measurement thresholds, and/or other associated records in the data file.

The dataset layout can be specified using either a fixed or relative date range. The relative date range provides the flexibility of allowing the same criteria to produce different results at different times (the actual date range can vary; new wafers meeting the other criteria may have been added; older wafers may have been purged from the database).

Figure 16:
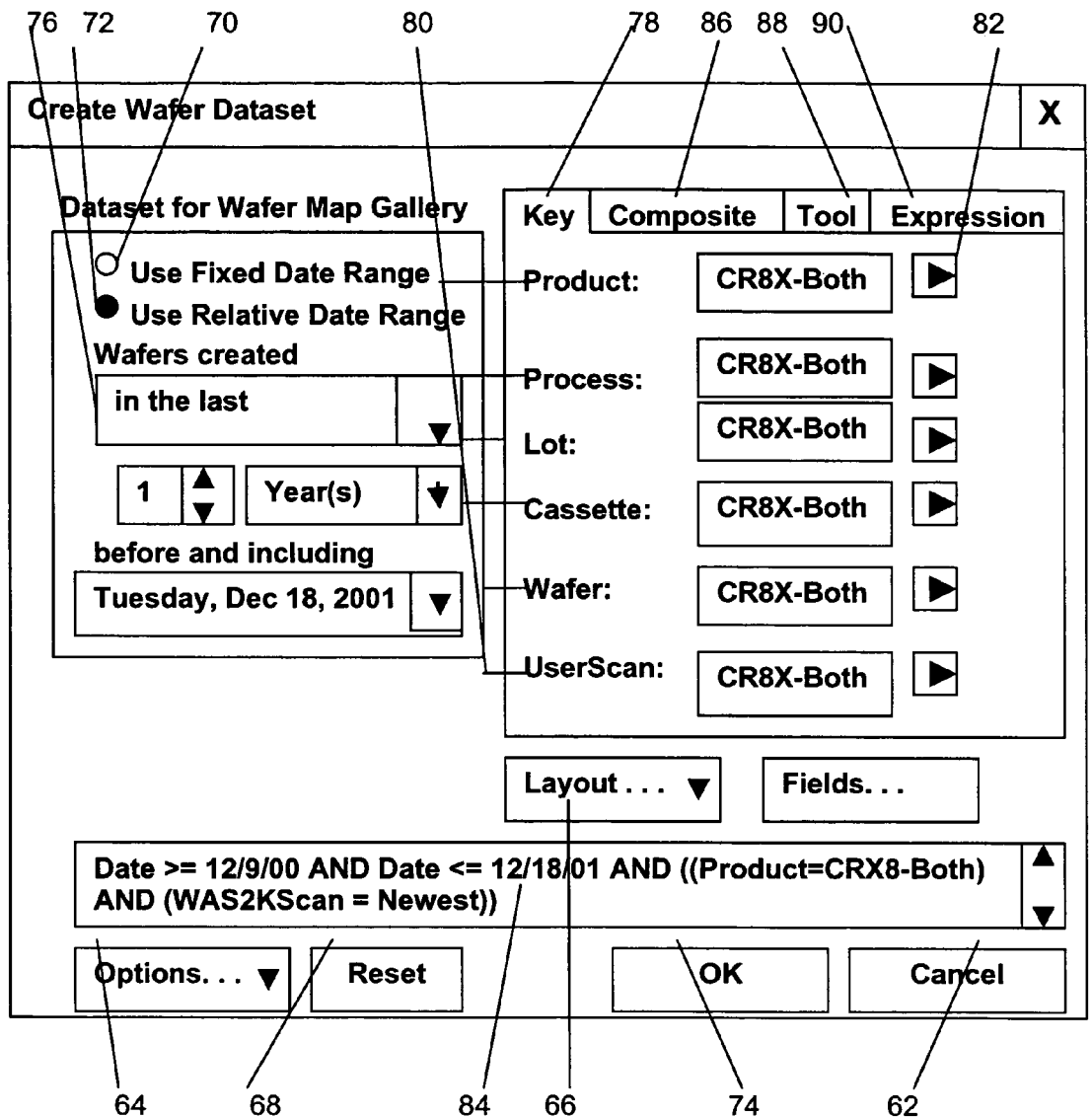
FIG. 16 is a block diagram of a screen for the Create Wafer Dataset dialog box for the Data Analysis System shown in FIG. 2.

With reference now to FIG. 16, the Create Wafer Dataset dialog box, available by using the Create Dataset icon or by selecting File>Create Dataset from the menu, is ideal for quickly creating a dataset for one-time use in FIG. 4's Utility Window 20's Wafers 26 tab galleries.

The Edit Dataset Layout and New Dataset Layout dialog boxes, available in the Utility Window 20's Layouts 26 tab (of FIG. 4), allow a user to also name and edit re-usable Dataset Layouts. Users can run an existing dataset layout, modify its criteria, or define new criteria to create a new dataset.

Returning to FIG. 16, the Dataset dialog, the name for which varies depending on how a user accesses it (Create Wafer Dataset, New Dataset Layout, or Edit Dataset Layout), lets a user specify criteria for creating datasets from the wafers in a database. The Dataset dialog is divided into areas for narrowing a search based on when the wafers had to have been measured and what the required measurement and other data values are. The Fields 62 button allows a user to specify which wafer data values will appear in the extended data after the search.

Settings available in the Options 64 and Layout 66 buttons allow the setting of defaults and save and import settings.

Layout 66 Button:
  Options in the Layout 66 button of FIG. 16 allow a user to save and recall query settings.
  Copy From
  When creating a new dataset layout, click this option to import the query settings from an existing dataset layout. In the Copy From dialog, click the desired layout and click OK. (A user can also right-click a layout and select Edit if he or she wants to inspect a particular layout's settings.) All of the query settings in the current query or layout are updated to match the selected layout.
  Save As
  This is an alternative method to simply clicking on OK to save a dataset layout. If a user is editing query criteria for a dataset that is not a named layout, this is the only way to save it as a named layout with re-usable settings.

Dataset Dialog's Options Button
  Still in FIG. 16, the Create Wafer Dataset, New Dataset Layout and Edit Dataset Layout dialogs used to create and edit dataset layouts have an Options 64 button allowing for the control of the wafers and data parameters that can appear in a dataset, and setting of default parameters that will be used whenever new datasets are created.
  Max Number of Rows
  A user may click this item to access another dialog box allowing setting limits on the number of wafers that can be included in a single dataset and the number of wafers that can be included in a composite. Increasing the default values allows the viewing of more data, but may adversely affect system performance and risks attempting to process more data than computer system resources allow.
  My Default Wafer Fields
  If a user finds that the Dataset dialog's Fields 62 button are used to request the same parameter set often, a user can specify a default setting that will be used for all future datasets. This is configured using the same method as Wafer Fields described above.
  Reset 68 Automatically
  This parameter determines whether the settings in all of the query dialogs are reset to include no filtering upon the start of a new query. Setting this to checked ensures that a user is starting fresh each time a new dataset is created. Setting this to unchecked keeps the settings that were in effect for the last dataset query that was used. This is helpful if several similar datasets need to be created.

Specifying Dataset Fields

Wafer Fields
  When editing query settings for a new dataset or an existing dataset layout, a user can specify which wafer fields are reported in Utility window 20's Wafers 26 tab, shown in FIG. 4, when Extended Data mode is selected. The Wafer Fields order also determines which fields are included in each of the thumbnails for Classic Gallery, Group Gallery and Multi Dataset Gallery.
1. Returning to FIG. 16 access the Dataset dialog for the dataset being created or the layout being edited.
2. Click the Fields 62 button to access the Wafer Fields dialog. The Available Fields column lists expandable categories of parameters that can be added to the list of reported fields. The Selected Fields column lists the currently selected Wafer Fields parameters. The included parameters and their order are based on either the last edit of Selected Fields for this dataset or the default setting for new datasets. (To change the default setting, select My Default Wafer Fields from the Options button.)
3. Edit the list as follows:
    To remove a Selected Fields parameter from the list, click the parameter, then click the Remove button or press the <Delete> key.
    To add a new parameter to the Selected Fields list, click the plus-sign for any Available Fields category, then click the desired parameter, then click the Add button.
    To change the order of appearance of items in the Selected Fields list, click a parameter to be moved, then click the up or down arrow above the list.

Creating a New Dataset
1. Click the Create Dataset icon or select File>Create Dataset. The Create Wafer Dataset dialog box shown in FIG. 16 will appear.
    Settings in the upper left portion of the dialog specify which wafers to include based on when they were characterized.
    Settings in the upper right portion of the dialog specify which wafers to include based on what measurement values or descriptive identification strings are in their records.
    The window at the bottom of the dialog displays a version of the criteria that will be converted to SQL code.
2. Select Use Fixed Date Range 70 or Use Relative Date Range 72 to specify a date range. This defines a range of specific dates during which the wafers had to be measured in order to be included in the dataset.
3. Click the Reset 68 button at the bottom of the dialog box. This ensures that all of the tabbed dialog boxes are restored to their initial state, with no "filtering" based on wafer parameters. (Depending on whether other datasets have already been created, some of these dialogs may already have settings that should be cleared.)
4. In the series of tabbed dialog boxes at the upper right area of the Create Wafer Dataset dialog box of FIG. 16, specify the equipment/process names and wafer measurement value requirements for inclusion into the dataset. If a user wants to be able to re-use or edit dataset definitions at a later date, click the Layout 66 button, then select Save As. In the Save As dialog, enter a name for the dataset and click OK. It is desirable to use descriptive names that can distinguish datasets from each other. In order to save all criteria, perform this step only after defining all of criteria.
5. Click the OK button at the bottom of the dialog.
    In the Detail Window 24, of FIG. 4, the Tasks 25 tab will add two new line items to indicate that the dataset was created and report the number of records (wafers) that were included. A user may need to click the Tasks 25 tab in order to view this.
    In the Utility Window 20 of FIG. 4, the Wafers 26 tab will display the wafers defined by this query, and show the Dataset name in the box above the wafer data. If the Layouts tab is currently displayed, click the Wafers 26 tab to view this.

Dataset Criteria Editing
  Returning again to FIG. 16, dataset criteria may be defined in a single dialog box that contains four main areas:
    Name
    Date Range
    Wafer Criteria
    Buttons for Layouts, Options and Fields Specifying a Dataset Date Range
  Still in FIG. 16, two options are available for specifying the range of dates during which the wafers had to be scanned in order to be included in the dataset:

Fixed Date Range 70:

Specific starting and ending dates may be specified. Any wafers measured during this range that also meet measurement criteria are accepted into the dataset. This method has the advantage of usually including the same wafers any time the saved dataset layout is run.

Relative Date Range 72

A date range that is relative to the current time (for example, the previous month) may be selected. Any wafers measured during this range that also meet measurement criteria are accepted into the dataset. This method has the advantage of being flexible to include the most recently acquired wafer data.

Specifying a Fixed Date Range
1. In the upper left area of the Create Wafer Dataset dialog box, of FIG. 16 click Use Fixed Date Range 70.
2. Set the Start Date to the desired setting using the following methods:
   Click the currently displayed month to highlight it, then press the up and down arrow keys to increment and decrement the month, respectively. Press the <End> key to set the month to December; press the <Home> key to set the month to January.
   Click the currently displayed day. Similarly, press the up and down arrow keys to increment and decrement the day, respectively. Press the <End> key to select the last day of the month; press the <Home> key to select the first day of the month. Additionally, a user can type a specific day value.
   Click the currently displayed year, by similarly pressing the up and down arrow keys to increment and decrement the year, respectively or by typing a specific year value.
   Click the arrow to the right of the End Date data entry box, and a calendar will display. Click the right and left arrow buttons (or press the <Page Up> and <Page Down> keys) to increment and decrement the month, respectively. Once a user has selected a month, use the arrow keys to change the date, or simply click a specific date. However, queries with relative date ranges will accept different wafers at different times, as older wafers will no longer be included in the range.
3. Similarly, set the End Date.
4. Edit the wafer measurement criteria, or click OK to immediately create a dataset with the current date range and wafer measurement criteria.

Specifying a Relative Date Range 72
1. In the upper left area of the Create Wafer Dataset dialog box of FIG. 16, click Use Relative Date Range 72.
2. In the Wafers Created 76 box, select one of the following methods:
   In the last: Select a certain number of days, weeks, months or years before and including a specific date (for example, in the last 3 months before Jan. 10, 2001). Use the arrows to the right of the boxes to determine the interval, then select the target date using the methods described below.
   In the following: Select a certain number of days, weeks, months or years after and including a specific date. Use the arrows to the right of the boxes to determine the interval, then select the target date using the methods described below.
   Today: Select wafers measured today.
   Yesterday: Select wafers measured yesterday
   This week: Select wafers measured from the most recent Saturday (which could be today) through the and including next Friday (which could be today). Refer to the code at the bottom of the dialog box for the exact dates.
   Last week: Select wafers measured during the 7-day period ending the previous Friday. Refer to the filter logic description at the bottom of the dialog box for the exact dates.
   This month: Select wafers measured between the first and last days of the current month. Note that saving and re-using this criterion will produce different results as new wafer records get created throughout the month.
   Last month: Select wafers measured between the first and last days of the previous month.
   This year: Select wafers measured between the first and last days of the current year. Note that saving and re-using this query will produce different results as new wafer records get created throughout the year.
   Last year: Select wafers measured between the first and last days of the previous year
3. Edit the wafer measurement criteria, or click OK to immediately create a dataset with the current date range and wafer measurement criteria.

Specifying Wafer Criteria

A user has complete control over determining which wafers will be included in the dataset. Acceptance can be limited to particular process names or recipes, cassette or other equipment values, and any combination of measurement value ranges among the available Individual Measurement Printouts (IMPs) and defect data values. The process of narrowing down the dataset of wafers for analysis is sometimes referred to as "filtering".

In the selection criteria, a user also has the option of creating "Composite" wafers, which average and combine the measurement data for several wafers having common values for one or more designated fields. This creates a smaller dataset allowing quick comparison of trends among wafers with various combinations of key attributes.

Specifying Key Criteria

The Key 78 tab of the Create Wafer Dataset dialog box of FIG. 16 allows a user to "filter" (restrict) the acceptable wafers to those measured from particular products, processes, ingots or cassettes. Users can also filter by specific operators, or sample subsets from many lots by selecting specific wafer numbers.
1. Click the Key 78 tab.
2. Select one of the available parameters 80, and click the arrow button 82 to the right of its text entry box.
3. From the popup context menu, select Browse. All available values from the database are displayed for the selected parameter based on the other criteria that have already been selected. (For example, if only wafers from last week are included, any operators used only prior to that time will not be included.)
4. From the list of available values, click any that are desired for the dataset. More than none may be selected.
5. Click OK 74. The criteria are automatically entered into the text entry box. If multiple entries were selected, they are separated by "OR". Note that the text (that will later be converted to SQL code) displayed in the large box 84 at the bottom of the Create Wafer Dataset dialog box of FIG. 16 is also modified.
6. If necessary, edit the text entry. For example, a user may wish to place parentheses around the entire entry and precede it with "NOT". This would cause all values within the parentheses to be excluded. If the user has an application where specific entries should always be excluded, this approach is preferable to simply listing the entries to be included, because it allows the same selection to be used even after new acceptable entries become available.

7. Repeat the process from step 2 for any other parameters to be used as filters. If multiple parameters are selected within this dialog box, only wafers satisfying all of the filters (as well as other criteria defined throughout the Create Wafer Dataset dialog box) will be included in the dataset.

Specifying Composite Wafers

Still in FIG. 16, the Composite 86 tab of the Create Wafer Dataset dialog box allows the creation of a dataset that includes "composite wafers". Each composite wafer combines the measurement results of several wafers, yet may be treated as a single wafer in the Utility Window 20's wafer gallery or list. This is a good way to take a very large dataset and reduce it to a smaller number of records based on a single variable or multiple variables (related to process, equipment, time, operator, recipe).

Composite analysis, which combines data from different scans and even different tools, allows for combining data in new ways, allowing trends and patterns not otherwise apparent.

Composite wafer analysis: Multiple wafers may be overlaid to provide composite wafers with which defect patterns may be identified. Hundred of wafers may be combined in order to identify systemic patterns. Wafer composites may be scheduled to run in the background of the Server and the Client.

Composite data analysis: With the ability to read not only CSV files but also ADM (binary) files, data such as defect data may be superimposed on a map such as a haze map.

Multi-wafer metrics and statistics: Average, Min, Max, and Standard Deviations, Totals, and others may be calculated for selected wafer characteristics.

Creating composites allows immediate assessment of trends related to any combination of variables. For example, wafer data for different shifts in a workday could be grouped and compared to see how each shift's data varies. Further, a user could investigate whether variances were due to the time of day or the difference in personnel by comparing data run by the same individuals in the different shifts.

1. Click the Composite 86 tab of FIG. 16.
2. Click inside the Composite Dataset box to place a checkmark and activate the composite keys.
3. Click the arrow button to the right of the Group By box, then select a parameter. If a user chooses not to select any of the remaining Then By boxes, one record will be created for each different value in the database for the selected parameter. If a user chooses Then By selections, one record will be created for each unique combination.
4. Because composite datasets are typically created to simplify the data for a very large number of wafers, the user has the option of deciding whether to include only statistical data or all of the required wafer data to create wafer maps. Unless a user needs to create wafer maps, set the Get Wafer Map Information box unchecked to greatly reduce the processing time to create the dataset. From the list of available values, click any to be included in the dataset.
5. Click OK. The criteria are automatically entered into the text entry box. Note that if multiple entries were selected, they are separated by "OR". Note that the text (that will later be converted to SQL code) displayed in the large box at the bottom of the Create Wafer Dataset dialog box will be modified.

Specifying Tool 88 and Recipe Criteria

The Tool 88 tab of the Create Wafer Dataset dialog box of FIG. 16 allows a user to restrict the acceptable wafers to those measured on specific metrology tools or using only a specific recipe.

1. Click the Tool 88 tab.
2. Select one of the available parameters, and click the arrow button to the right of its text entry box.
3. From the popup context menu, select Browse. All available values from the database for the selected parameter based on the other criteria that have already bee selected will be displayed. For example, if a user only included wafers from one Process, any Tools used only for other processes will not be included.
4. From the list of available values, click any to be included in the dataset.
5. Click OK 74. The criteria into the text entry box are automatically entered. If multiple entries were selected, they are separated by "OR". The text (that will later be converted to SQL code) displayed in the large box 84 at the bottom of the Create Wafer Dataset dialog box of FIG. 16 is also modified.
6. If necessary, edit the text entry. For example, a user may wish to place parentheses around the entire entry and precede it with "NOT". This would all values within the parentheses to be excluded. If the user has an application where specific entries should always be excluded, this approach is preferable to simply listing the entries to be included, because it allows the same selection to be used even after new acceptable entries become available.
7. Repeat from step 2 for any other parameters to be used as filters. If multiple parameters within this dialog box are accepted, only wafers satisfying all of the filters (as well as other criteria defined throughout the Create Wafer Dataset dialog box) will be included in the dataset.

Specifying Wafer Criteria Using Expression Editor

Still in FIG. 16, in the Expression 90 tab of the Create Wafer Dataset dialog box, a user may build one or more logical expressions to filter the dataset based on IMP values or apply more complex filtering techniques using the parameters that are also available on the other tabs.

1. At the upper right area of the Create Wafer Dataset dialog box, click the Expression 90 tab.
2. Click the Add button to add a new expression, launching the Build Expression dialog box.
3. In the Build Expression dialog box, click the arrow button to the right of the Field box to view the available field categories.
4. Double-click one of the categories (or click the plus sign to the left of it) to display all of the available fields within the category.
5. Use the scroll bar to view all of the available fields within the category, then click the field to be used in the expression. NOTE: Do NOT click the OK button yet.
6. Click the arrow button to the right of the Operator box to view the available operators, then click one.
7. Type the appropriate value in the Value box, then click OK. The expression appears in the window.
8. To add another expression, repeat steps 2 through 7. Note that this second expression appears in the window and that the operator "AND" appears to the right of the first expression. This means that both expressions must be true (as must all of the conditions defined in other tabs) in order for the wafer to be accepted into the dataset. To change the requirement such that only one of the two expressions must be true, click either expression, then click the AND button at the lower right of the dialog box to toggle the operator to "OR".
9. Click OK 74.

Loading an Existing Dataset

After creating and saving named datasets, a user can quickly load one for analysis at any time.
1. In the Utility Window 20 shown in FIG. 4, click the Layouts 26 tab.
2. Click the arrow button above the layout list to select Datasets layouts.
3. From the list of Datasets, right-click the desired Dataset, then select Run.

The number of wafers in the dataset and the processing time required to load them depend on the query's filtering criteria. In the Detail Window 24, click the Tasks 25 tab to monitor the dataset loading progress and see how many wafers were loaded. Note that the wafers included in the dataset may vary if the query includes a relative date range or if records were added to or removed from the wafer database.

Wafer Maps and Wafer Map Layouts

Wafer maps provide an immediate visual representation of wafer thickness, flatness, shape, defect particles, defect density and other wafer properties. A variety of display options allow viewing of wafers in color or greyscale, in numerical or graphical format, and from a top view or in three-dimensional space from any angle. In addition, "composite" wafer maps, combining several wafers into a single map, may be created.

For dimensional data composite wafer maps, the results are
  displayed in the map by taking the data points from the selected wafers and applying mathematical operation of a user's choosing, such as addition or averaging or standard deviation.
For defects composite wafer maps, compositing includes all of the defects from the wafers included. Mathematical compositing is performed only for user-defined rings, sectors and regions.

Creating and Editing Wafer Maps

Creating a New Wafer Map

Use either of these methods to start creating wafer map settings in a new wafer map layout.

To Create a New Wafer Map Layout for Future Use

1. In the Utility Window 20 of FIG. 4, click the Layouts 26 tab.
2. Using the arrow button, select Wafer Maps layouts.
3. Right-click anywhere in the Utility Window, then select New.
4. Edit the wafer map layout, as described in Editing Wafer Map Layout General Parameters and Editing Wafer Map Layout Parameters, described below.

To Create a New Wafer Map Layout for Immediate Use on Selected Wafer Items

1. In the Utility Window 20's Wafers tab, select the wafer or wafers to be included in the wafer map.
2. Right-click, then select Wafer Map>Run With Selected Layout from the context menu.
3. In the Run With Selected Layout dialog, click the Options button, then select New.
4. Edit the wafer map layout, as described in Editing Wafer Map Layout General Parameters and Editing Wafer Map Layout Parameters, described below.
5. After configuring a new layout's settings, a user would click the new layout name from Run Wafer Map With Selected Layout list, then click OK. The wafer map is displayed using the selected wafer records and wafer map layout settings.

Editing Wafer Map Layout Settings

Access to the dialog box that contains wafer map layout parameters may be accomplished three different ways. The best method to use depends on the situation:
creating or editing a wafer map layout for future use
creating or editing a wafer map layout for immediate use after selecting wafers
adjusting the currently displayed wafer map Create/Edit a Layout for Future Use This method, which creates a wafer map layout but does not create the map itself, is best when making offline changes to several layouts or when creating or editing layouts that will be used at a later time. By not producing the maps on screen each time the layout is created, a user avoids having to wait while data are processed.
1. In the Utility Window 20 of FIG. 4, click the Layouts 26 tab.
2. Click the arrow button above the layout list to select Wafer Maps layouts.
3. From the list of wafer map layouts, right-click the desired layout and select Edit. If creating a new wafer map layout, right-click somewhere below the list of layouts and select New.

Using the Edit Layout or New Layout dialog shown in FIG. 17, edit the wafer map layout settings, as described in Editing Wafer Map Layout Parameters, described below.

Create/Edit a Layout for Immediate Use

This method selects and edits an existing wafer map layout, then creates a wafer map using the currently selected wafers in the currently selected dataset. If individual wafers are not selected, the entire dataset will be used.
1. Create a new dataset or load an existing dataset.
2. In the Utility Window 20 of FIG. 4, click the Wafers tab 26 to display the dataset.
3. Highlight the wafer of interest. Multiple wafers may be selected by clicking on individual records in the extended data wafer list or by clicking on individual thumbnails in the gallery. Use the <Shift> and <Ctrl> keys to select multiple wafers. To include all of the wafers in the dataset, right-click and select Select All.
4. Make sure the cursor is on one of the selected wafers, then right-click and select Wafer Map.
5. If multiple wafers are selected, note the item Composite Selected Wafers, whose setting (indicated by the presence of a checkmark) can be changed the opposite setting by clicking on this item. Set this item to checked if combining all of the wafers into a single wafer map. Set this item to unchecked if a separate wafer map for each wafer selected is desired. If a large number of wafers are selected, there may not be enough system resources be able to process all of the maps.
6. Place the cursor on one of the selected wafer or wafers, then right-click and select Wafer Map>Run With Selected Layout.

7. From the list of wafer map layouts, right-click the desired layout and select Edit.
8. Using the Edit Layout dialog of FIG. 17, edit the wafer map layout settings, as described in Editing Wafer Map Layout Parameters, as described below.

Updating a Displayed Wafer Map

This method edits the currently displayed wafer map (but does not update the wafer map layout).
1. In the Analysis Window 22 of FIG. 4, click the wafer map to be edited.
2. Click the Properties icon or select View>Properties.
3. Using the Edit Layout dialog of FIG. 17, edit the wafer map layout settings, as described in Editing Wafer Map Layout Parameters, as described below. After updating a displayed wafer map, chart or report item, click the displayed item in the Analysis window, then select File>Save.

Figure 17:
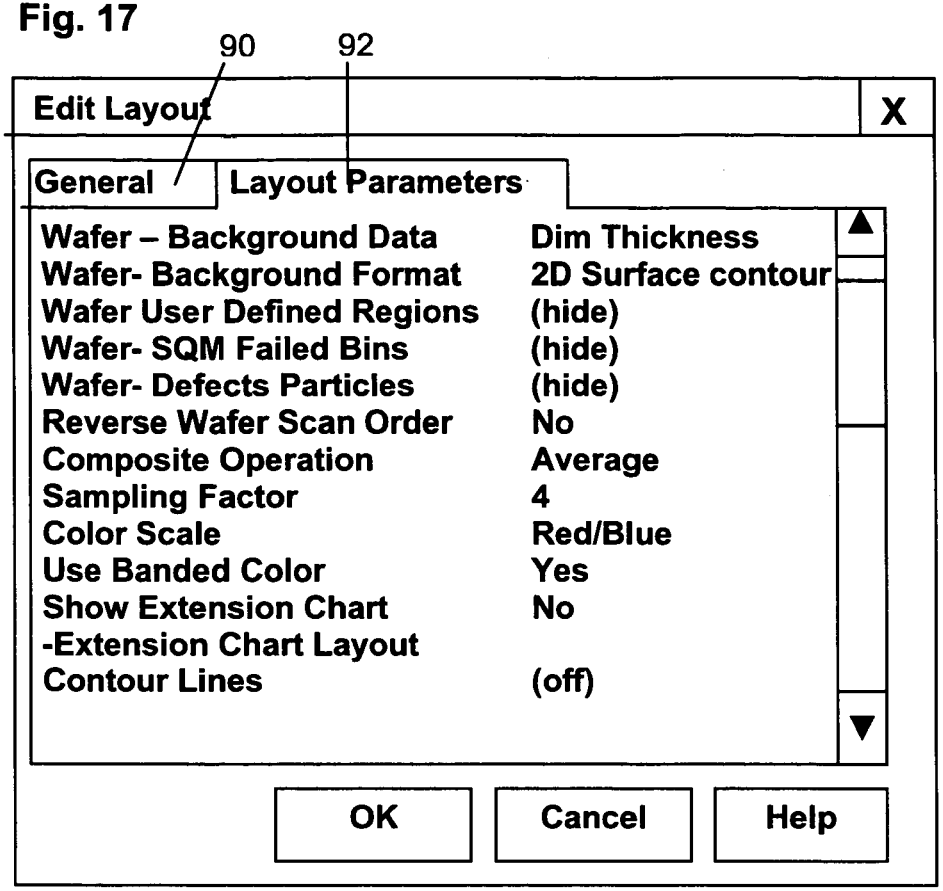
FIG. 17 is a block diagram of a screen for the Layout Parameters tab of the Edit Layout dialog for the Data Analysis System shown in FIG. 2.

Once the New Layout or Edit Layout dialog box of FIG. 17 is launched, a user can define all aspects of wafer map content and formatting. Note that a wafer map layout cannot select which wafers will be reported. The dialog box for editing wafer map layouts includes two tabbed dialogs: General 90 Tab and Layout Parameters 92 Tab, Editing Wafer Map Layout General Settings Still in FIG. 17, settings in a wafer map layout's General 90 tab specify the layout's name, title and a brief description. In the New Layout or Edit Layout dialog, click the General 90 tab.
Name: This field allows a layout descriptive name that is 30 characters or less.
Description: This field allows a description of the layout's purpose, detailed instructions for users, or any other helpful information. The notes and comments entered here are for personal use and will not be included in the actual wafer map display. This is a good place for a user to enter any notes that will other users to distinguish the layout from other available layouts, or which datasets are intended to be used with the layout.
Title: Specify a title that will appear at the top of all wafer maps created with this layout.

Editing Wafer Map Layout Parameters

Still in FIG. 17, a single dialog box in the wafer map layout's Layout Parameters 92 tab allows specification of all content and display details which define the wafer map.

Wafer—Background Data

Click inside the selection box, then use the arrow button to the right of the selection box to specify the dimensional measurement surface or property that will be displayed in the wafer map. Options include:

| | |
|---|---|
| [hide] | Displays no background data. Selecting this option is typically done only to display particle defects with no background. |
| Dim Thickness | To display thickness, the map reports the deviation of all points on the frontside surface from the ideal backside reference plane. Note that all points are adjusted mathematically to simulate a chucked state (i.e., applied vacuum makes the wafer backside perfectly flat). |
| Dim Flatness3PT | The map reports the deviation of all points on the frontside surface from the three-point global reference plane. All points are adjusted mathematically to simulate a chucked state (i.e., applied vacuum makes the wafer backside perfectly flat). |
| Dim FlatnessBF | The map reports the deviation of all points on the frontside surface from the best fit global reference plane. Points are adjusted mathematically to simulate a chucked state (i.e., applied vacuum makes the wafer backside perfectly flat). |
| Dim Warp3PT | The map reports the deviation of all points on the median surface from the three-point median reference plane. Values for this measurement are for the wafer in an unchucked state. |
| Dim WarpBF | The map reports the deviation of all points on the median surface from the best fit median reference plane. Values are for the wafer in an unchucked state. |
| Dim SORI | The map reports the deviation of all points on the frontside surface from a best fit reference plane fitted to the frontside surface with the wafer in an unchucked state. |
| Dim STIR, Dim SFPD | This map mode provides a gridded display of the individual sites on the wafer, with site flatness (STIR or SFPD) measurements and "go"/"no-go" status for each site. See Site Map below for more details. |
| Defect Density | The map displays the density of defects on the wafer surface within previously defined rings and sectors. |
| SQM Height | The map displays the wafer nanotopology. |

Wafer—Background Format

Figure 18:
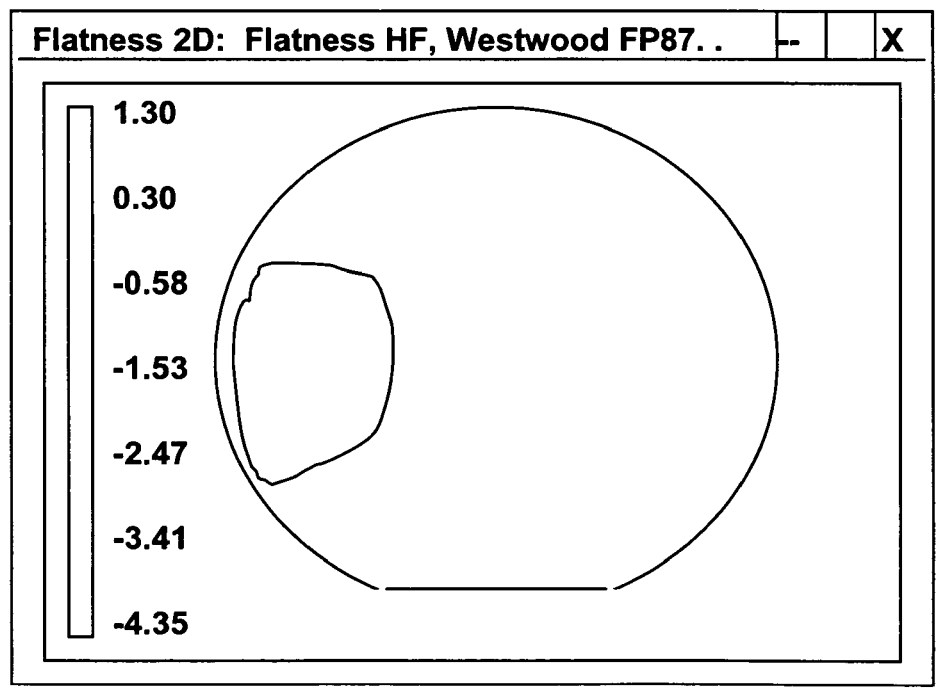
FIG. 18 is a block diagram of a screen showing the 2D Surface Contour display option for specifying Wafer-Background Format in the Layout Parameters tab shown in FIG. 17.

Click inside the selection box, then use the arrow button to the right of the selection box to specify the desired graph format. Available options include:

2D Surface Contour mode, as shown in FIG. 18, offers a two-dimensional view of the wafer's front side or median surface, depending on the selected Data. Optionally configured contour lines or bands of color connect points of equal values (for contour lines) or ranges (for color bands). Values in the map represent one of the following: thickness, deviation of the chucked wafer's top surface points from the selected focal plane (FPD, deviation of the chucked wafer's top surface points from the selected focal plane (Sori), variation from the median surface to the median reference plane (Warp) or SQM height.

Figure 19:
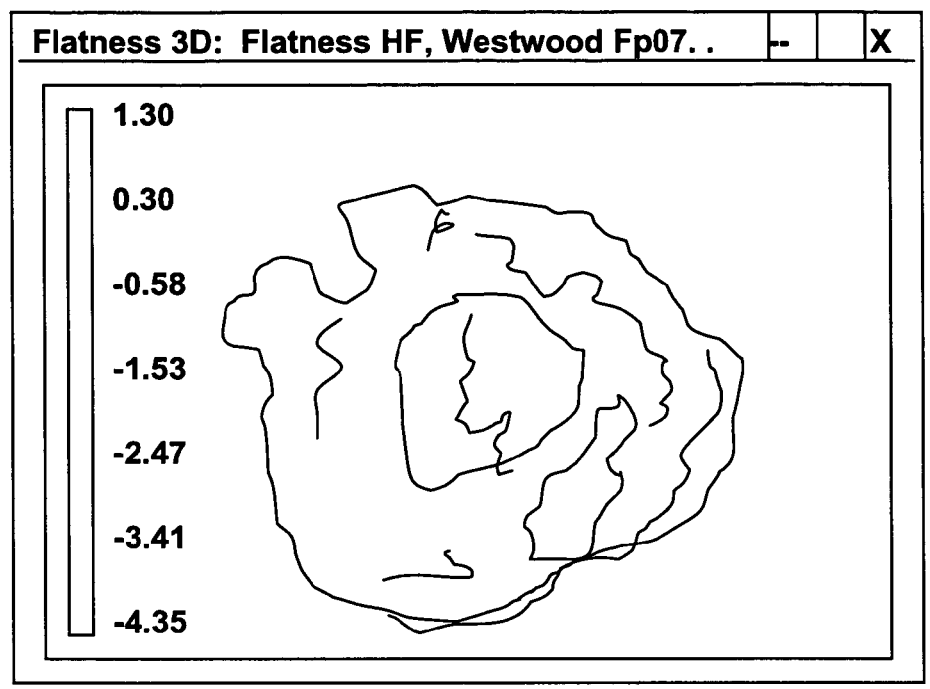
FIG. 19 is a block diagram of a screen showing the 3D Surface Contour display option for specifying the Wafer-Background Format in the Layout Parameters tab shown in FIG. 17.

3D Surface Contour mode, as shown in FIG. 19, offers a three-dimensional model of the wafer's front side or median surface, depending on the selected Data. Using the mouse pointer, a user can drag on the interactive display to change the angles of rotation, adjust the zoom, or cause the wafer to spin in 3D space.

Figure 20:
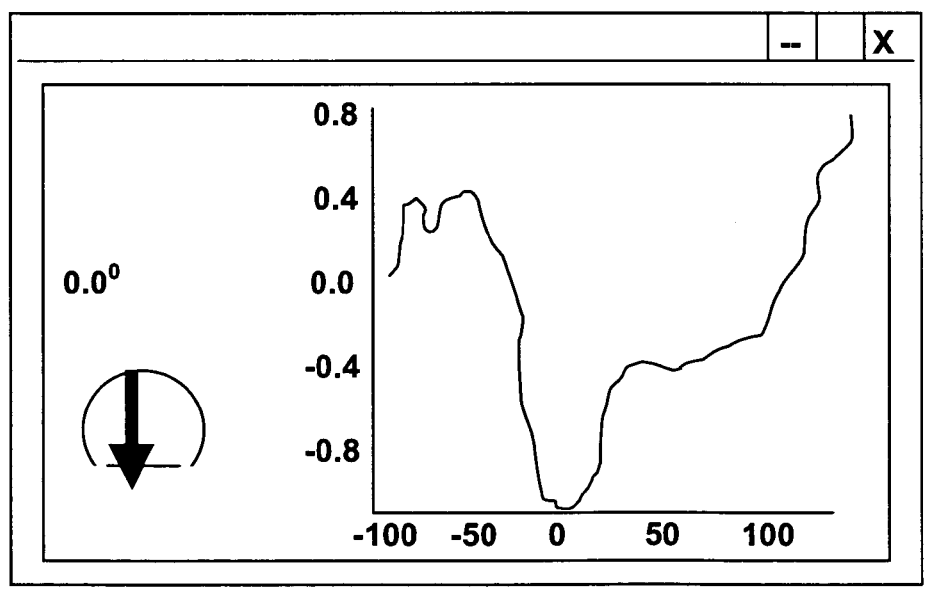
FIG. 20 is a block diagram of a screen showing the Cross Section display option for specifying the Wafer-Background Format in the Layout Parameters tab shown in FIG. 17.

Cross Section mode, as shown in FIG. 20, displays a plot of SQM height, wafer thickness, flatness (focal plane deviation from the selected best fit or three point reference plane), or shape (for Warp, median surface deviation from a best fit or three point median reference plane) (for Sori, unchucked front surface deviation from a best fit front side reference plane) along a user-specified cross-section. The angle for the cross section "slice" is set in the Layout Parameters 92 dialog's Cross Section—Angle item described below. After the map is displayed, a user can use the mouse pointer to drag on the arrow in the interactive display, continuously changing the slice angle.

Figure 21:
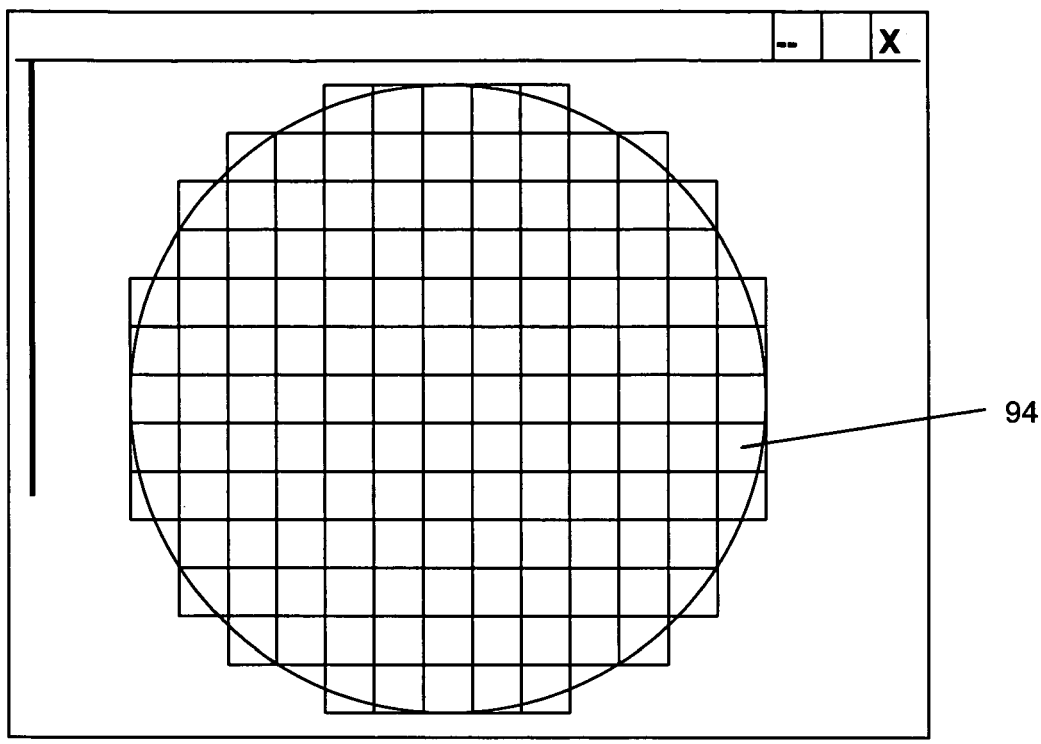
FIG. 21 is a block diagram of a screen showing the Site Map display option for specifying the Wafer-Background Format in the Layout Parameters tab shown in FIG. 17.

Site Map mode, as shown in FIG. 21, provides a gridded display of the individual sites 94 on the wafer, with site flatness (STIR or SFPD) measurements and "go"/"no-go" status for each site. All site measurement values are compared against a threshold value that was supplied in the data acquisition or reprocessing recipe. Sites whose values that are within tolerance are displayed in green; sites whose values that out of tolerance are displayed in red. The sites whose values are closest to the threshold value are shaded the lightest; sites whose values are furthest from the threshold value (either within or out of tolerance) are shaded the darkest. Note that all site configuration parameters (i.e., site size, grid and row offsets, whether partial sites are displayed) are as specified in the recipe that was used during data acquisition or reprocessing.

Figure 22:
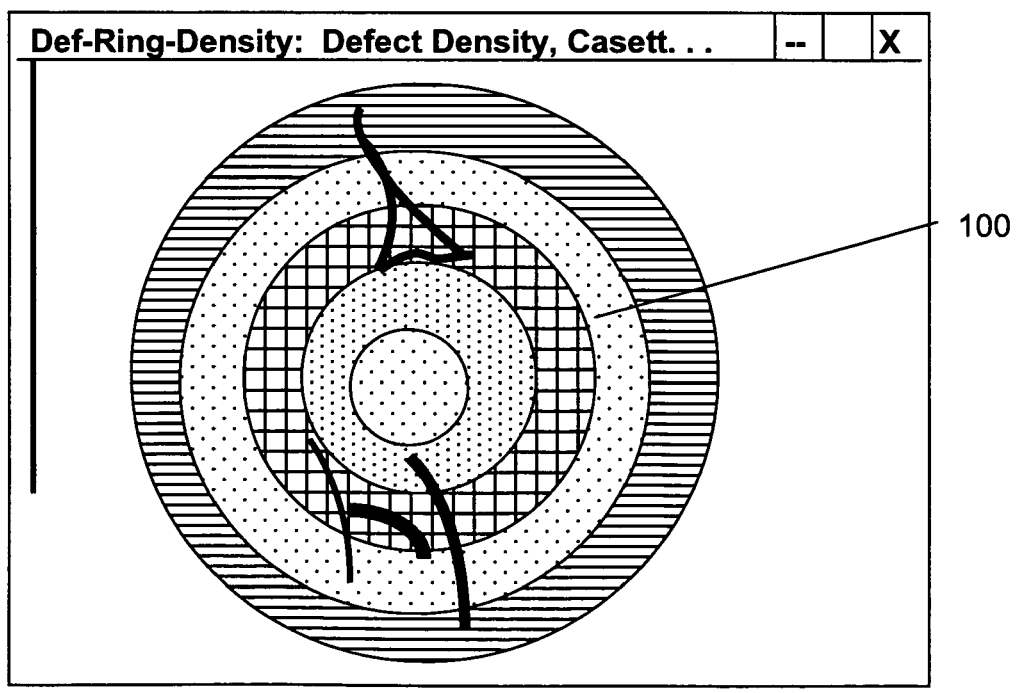
FIG. 22 is a block diagram of a screen showing the Defect Rings display option for specifying the Wafer-Background Format in the Layout Parameters tab shown in FIG. 17.

Defect Rings mode, as shown in FIG. 22, presents a series of previously defined concentric rings 100 which are colored according to the wafer's defect density. Ring definitions are specified in the configuration using Microsoft Management Console (MMC). Each ring is assigned a single color based on the density for the region. For composite wafer maps, each ring is colored according to the method selected in the layout's Composite Operation.

Figure 23:
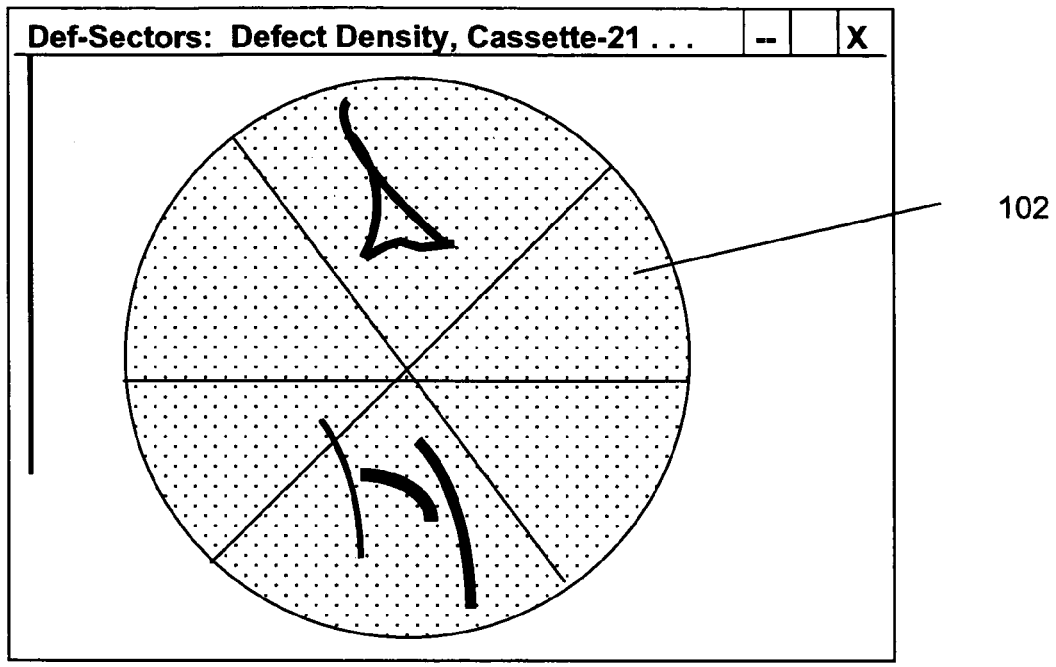
FIG. 23 is a block diagram of a screen showing the Defect Sectors display option for specifying the Wafer-Background Format in the Layout Parameters tab shown in FIG. 17.

Defect Sectors mode, as shown in FIG. 23, presents a series of "pie slices" which are colored according to the wafer's defect density. Each sector 102 is assigned a single color based on the density for the region. For composite wafer maps, each sector is colored according to the method selected in the layout's Composite Operation. Sectors definitions are specified in the configuration using Microsoft Management Console (MMC).

Figure 24:
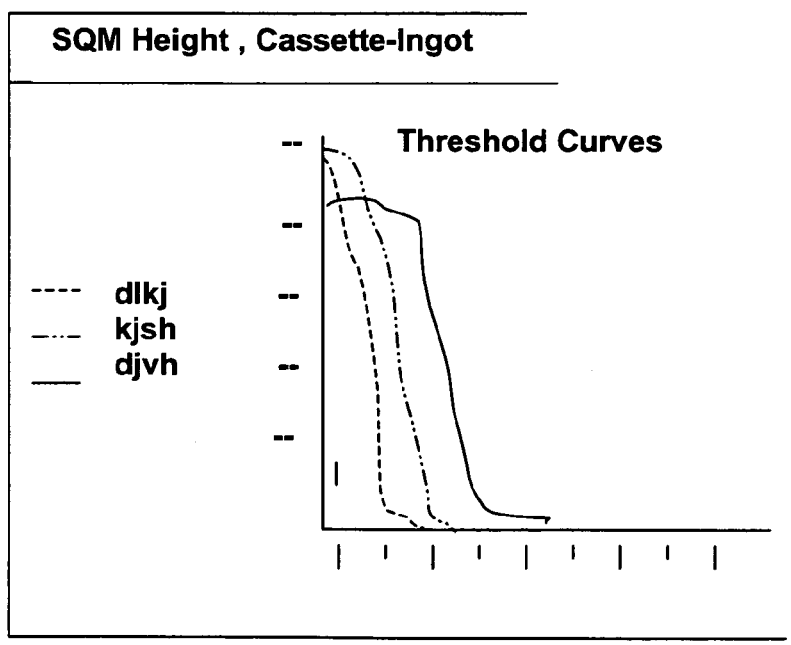
FIG. 24 is a block diagram of a screen showing the SQM Height Threshold display option for specifying the Wafer-Background Format in the Layout Parameters tab shown in FIG. 17.

SQM Height Threshold mode, as shown in FIG. 24, presents SQM threshold curves for each defined bin, showing all of the corresponding percentage area failed values for varying height change threshold values.

Figure 25:
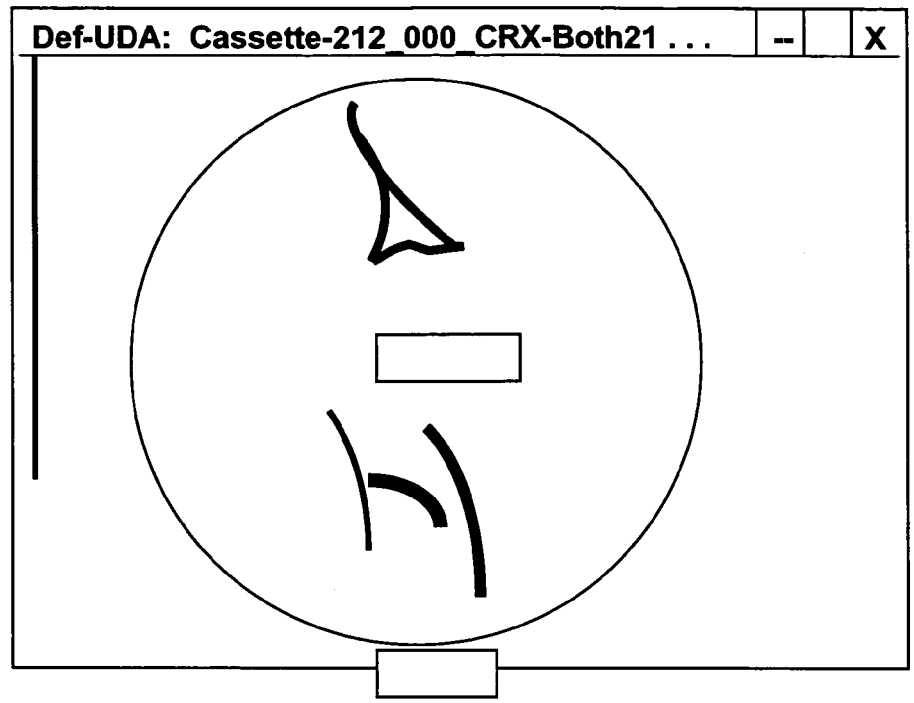
FIG. 25 is a block diagram of a screen showing the Wafers-Region display option for specifying the Wafer-Background Format in the Layout Parameters tab shown in FIG. 17.

Wafer—Regions mode, as shown in FIG. 25, displays wafer defects in user-created regions that are defined previously in the configuration using Microsoft Management Console (MMC). Click inside the selection box, then use the dropdown menu arrow button to the right of the selection box to specify the desired setting. Available options include:

[hide]
Density with Black Outline
Density with Highlighted Outline
Outlined with Black
Outlined with Density Color
Outlined with Highlight Color Wafer—SQM Failed Bins: When set to [show], this parameter colors pixels in the wafer map red if the SQM height variation exceeds one or more "bins" of user-selectable distance and threshold values. All unaffected pixels will remain as specified by the Wafer—Background Data and Wafer—Background Format settings. Click on the displayed current setting inside the selection box to toggle it to the opposite setting. A user should set this parameter to [hide] unless wafer data includes SQM failed bin data.

Wafer—Defects Particles: Setting this parameter to a selection other than [hide] allows a view of defects particles, colored according to a variety of options to enhance interpretation of the defect data. Note that the displayed particles appear over whichever wafer data is displayed according to the Wafer—Background Data and Wafer—Background Format settings. A user would click inside the selection box, then use the arrow button to the right of the selection box to specify the desired setting. Available options include:

| | |
|---|---|
| [hide] | Does not display defects. |
| Bin | Colors each defect according to which user-defined bin it was sorted into. Bins are defined in the configuration using Microsoft Management Console (MMC). |
| Bin (True Size) | Colors each defect according to the size as determined by the True Size Algorithm, part of the optional Toolboxes: ThinFilms and Correlation. |
| Channel | Colors each defect according to the gage channel on which it was detected: Back, Front, Center, Extinction, Radial, Tangential or Other. |
| Defect Type | Colors each defect according to its type: Point, Line, Area, or Other. Note that scratch defects are classified as Line. |
| Lost Common Adder | Intended for 2-wafer composite wafer maps, this option colors each defect according to whether it was present only on the first wafer (Lost), present on both wafers (Common), or present on only the second wafer (Adder). If more than two wafers are selected, only uses the first two wafers. |
| Material ID | Color each defect according to the Material ID as determined by the True Size Algorithm, part of the optional Toolboxes: ThinFilms and Correlation. |
| Monochrome | Displays all defects using the same color. |
| Wafer Scan | Intended for composite wafer maps, this option colors each defect according to the wafer on which it was present. |

Reverse Wafer Scan Order: This parameter selects the order and layering for wafer map display when multiple wafers are selected and compositing is not selected. A user would click the displayed current setting inside the selection box to toggle it to the opposite setting.

No causes the first of the wafers selected in the Wafers tab to be drawn first and the last (bottom-most) wafer to be drawn last. This results in the last wafer at the top of the "stack" of wafer maps.

Yes causes the last of the wafers selected in the Wafers tab to be drawn first and the first (top-most) wafer to be drawn last. This results in the first wafer at the top of the "stack" of wafer maps.

Composite Operation: A user would click inside the selection box, then use the arrow button to the right of the selection box to specify one of the following compositing methods to be used when multiple wafers are selected and compositing is selected. Available options include:

| | |
|---|---|
| Average | Each point on the displayed surface is the average for that point among all of the wafers in the composite. |
| Minimum | Each point on the displayed surface reports the lowest value for that point among all of the wafers in the composite. |
| Maximum | Each point on the displayed surface reports the highest value for that point among all of the wafers in the composite. |
| Standard Deviation | Each point on the displayed surface reports the calculated standard deviation for that point among all of the wafers in the composite. |
| Subtraction | Each point on the displayed surface reports the difference of values between the first two wafers in the composite. |
| Total | Each point on the displayed surface reports the sum of all values for that point among all of the wafers in the composite. |

Sampling Factor: Intended for contour maps only, this parameter determines the percentage of available data points used when drawing wafer maps, allowing a user to balance processing speed and data map resolution. Click inside the selection box and type a value between 1 and 10. A value of 1 uses all available data values and provides the best display, but requires the most processing time. A value of 10 uses the least number of data values and provides the lowest resolution display, but requires the least processing time. Higher values (i.e., lower resolution) should be selected when the layout is intended to be used with large data sets and/or 300 mm wafers. For SQM wafer maps, 4 is the recommended value.

Figure 26:
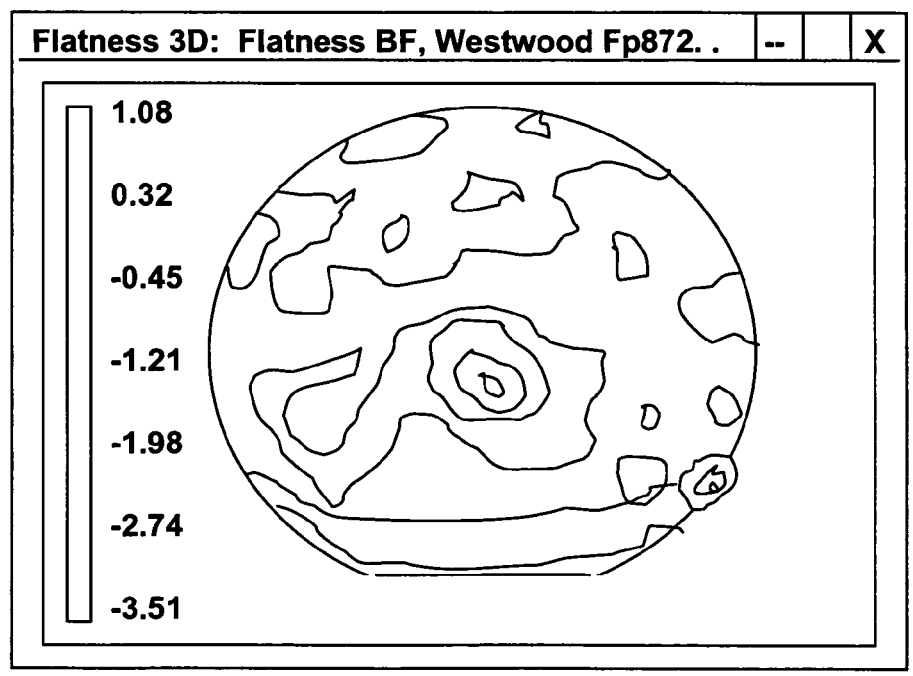
FIG. 26 is a block diagram of a screen showing the Use Banded Color display option for the Layout Parameters tab shown in FIG. 17.

Color Scale mode, as shown in FIG. 26: A user would click inside the selection box, then use the dropdown menu arrow button to the right of the selection box to specify a color scale for contour maps. If Wafer—Background Format is not 2D Surface Contour or 3D Surface Contour, this setting is ignored.

| | |
|---|---|
| Red/Blue | Applies full color to the map, with red representing the highest values and blue representing the lowest values. Note that the range of color is mapped to the Height Range. Any values higher than the Height Range high value are displayed as red; any values lower than the Height Range low value are displayed as blue. See Height Range later in this chapter for more details. |
| Grey (Light, Medium, Dark) | Draws the map in greyscale. Three choices allow a variety of darkness options. |

Use Banded Color: This item, when activated, displays the selected color range as a small set of color values in contour maps. In some cases, this helps a user see the data values in the wafer map more clearly. Click the displayed current setting inside the selection box to toggle it to the opposite setting. If Wafer—Background Format is not 2D Surface Contour or 3D Surface Contour, this setting is ignored.

Yes: Only a subset of the color range is used; wafer measurement values within specific ranges are assigned specific colors.

No: The full color range is used; the color for each display point is based on the relationship between its measurement value and the selected Height Range.

Figure 27:
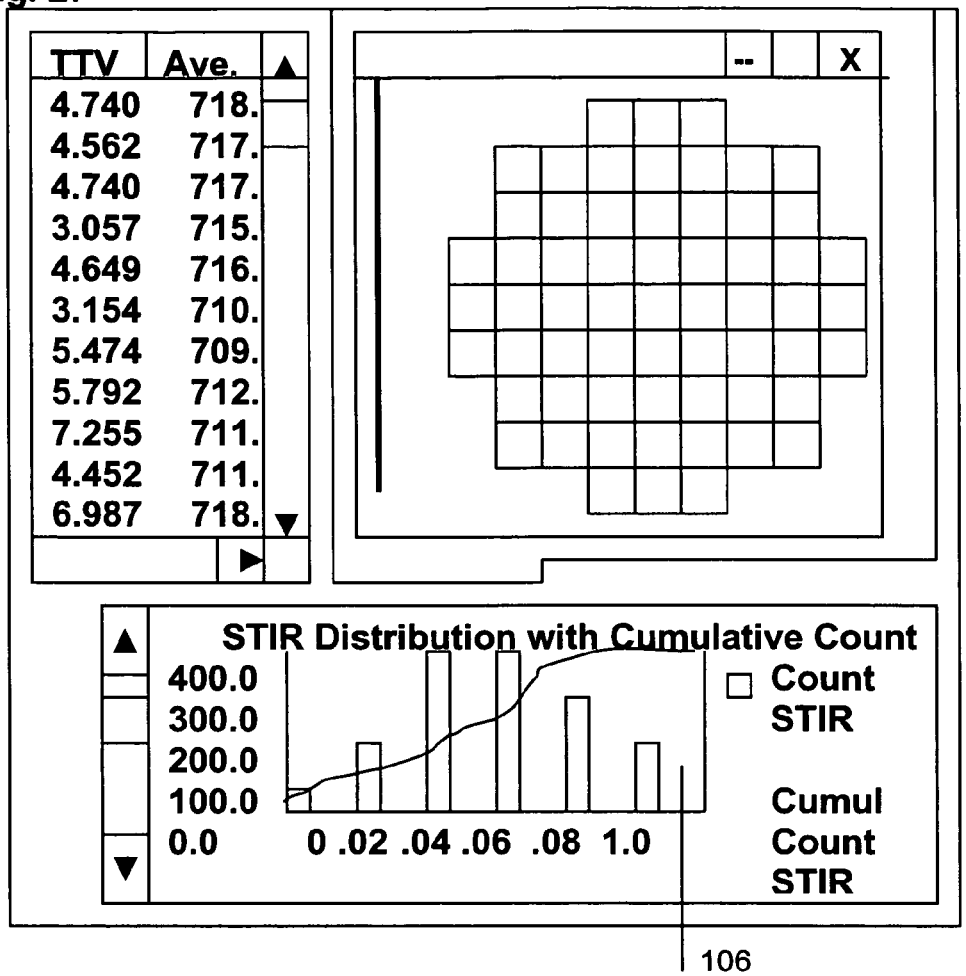
FIG. 27 is a block diagram of a screen showing the Extension Chart Layout display option for the Layout Parameters tab shown in FIG. 17.

Show Extension Chart mode, as seen in FIG. 27: This item, when set to Yes, attaches a chart 106 to the wafer map, displaying the chart in a separate window at the lower right of the screen. The chart uses the same dataset and wafers as the wafer map, and requires a named chart layout. Click the displayed current setting inside the selection box to toggle it to the opposite setting.

Extension Chart Layout: If a user activated the Show Extension Chart option above, click inside the selection box, then use the button to select one of the existing chart layouts. If a user needs to create a new chart layout, a user can click the Select Chart Layout dialog's Options button and select New, then select the new layout from the list after a user edits the settings.

Figure 28:
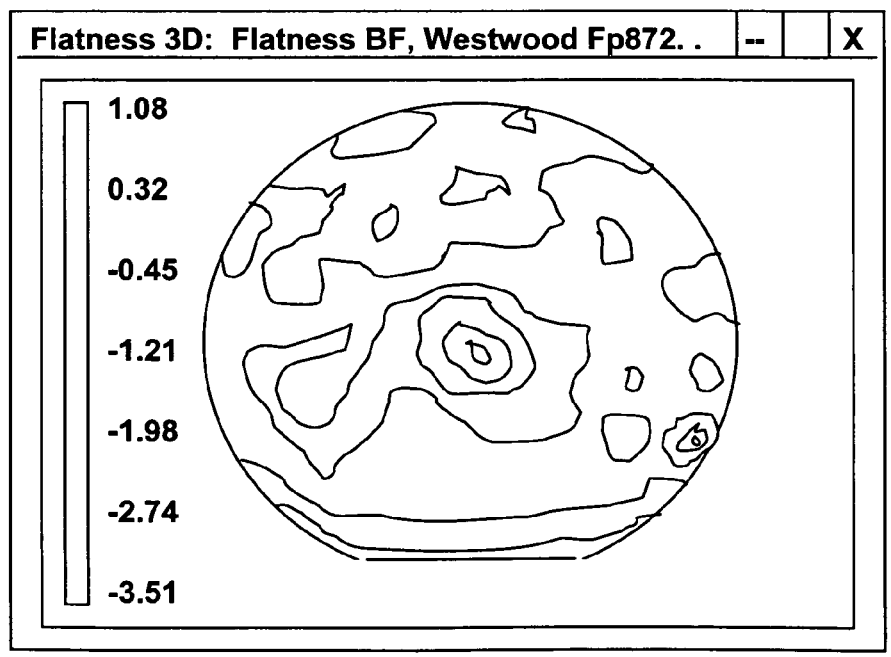
FIG. 28 is a block diagram of a screen showing the Contour Lines display option for the Layout Parameters tab shown in FIG. 17.

Contour Lines, as shown in FIG. 28: This item, intended for 2D and 3D contour wafer maps only, adds lines to the displayed surface connecting points of equal deviation from the appropriate reference plane. A user would click inside the selection box, then use the arrow button to the right of the selection box to select one of the following options:

| | |
|---|---|
| Off | Specifies no contour lines. |
| Interval | Specifies the spacing of the deviation values represented by the contour lines. |
| Method | |
| Count Method | Specifies the number of contour lines displayed in the wafer map. |

Num Contour Lines: This parameter is used for 2D and 3D contour wafer maps when Contour Lines is set to the count method. Click inside the selection box and type a value between 1 and 100.

Contour Interval: This parameter, used for 2D and 3D contour wafer maps when Contour Lines is set to the interval method, specifies the difference in wafer thickness or deviation values between points along adjacent contour lines. A user would click inside the selection box and type the desired value. Lower interval settings cause a greater number of contour lines to be drawn. With extremely low contour interval values, the number of contour lines requested may exceed the capability allowed by computer system resources.

Height Range: This parameter selects a range of measurement values that will be "mapped" to the selected range of color for 2D and 3D contour maps. Each wafer point whose measurement value equals or exceeds the high value of this range will be drawn red (or the lightest available greyscale color). Each wafer point whose measurement value is equal to or less than the high value of this range will be drawn blue (or the darkest available greyscale color). Any wafer values between this range are drawn in a color whose relationship to the color range is the same as the wafer value's relationship to the Height Range. A user would click inside the selection box, then use the arrow button to the right of the selection box to specify the following height ranges:

Automatic: Wafer map coloring is scaled automatically according to the data reported in the map (a user does not need to specify user defined low and high values below). The point with the highest measurement value is assigned to red (or the lightest available greyscale color); the point with the lowest measurement value is assigned to blue (or the darkest available greyscale color). Note that this method always ensures that every wafer map will use the full range of color or greyscale. However, points having equal measurement values may be colored completely differently in different maps if the range of all measurement values varies from map to map.

User Defined: A user selects a custom measurement range to be applied to the selected color range. Specify the range limits using the User Defined Low Value and User Defined High Value below.

±25, ±50, ±100, ±150, ±200: Choose one of the available ranges to apply to the selected color range (a user does not need to specify user defined low and high values below). Note that this method may produce wafer maps that are uniformly colored if all of the measurement values in the wafer map are outside the selected range.

User Defined Low Value: A user would click inside the selection box and type the desired value. Any values in the map that are equal to or lower than this value will be colored blue (or the darkest available greyscale color).

User Defined High Value: A user would click inside the selection box and type the desired value. Any values in the map that are equal to or greater than this value will be colored red (or the lightest available greyscale color).

Cross Section—Angle: Intended for cross section wafer maps only, this value determines the initial cross-sectional "cut" which bisects the wafer. A user would click inside the selection box and type the desired value. Once the wafer map is displayed, a user can adjust this angle interactively in the Analysis window. An initial setting of 0 degrees specifies a cut that starts 180 degrees from the primary fiducial and ends at the primary fiducial. The cross section angle increases as a user moves clockwise.

Cross Section—Point to Point: This parameter and the four coordinates parameters below it allow a user to create a wafer map layout that displays cross section data for a user-configurable cut which does not have to bisect the wafer or start and end at the wafer edge. A user would click the displayed current setting inside the selection box to toggle it to the opposite setting.

No: Specifies a cross section slice that bisects the wafer, starting and ending at a wafer edge, with the angle as set by the Cross Section—Angle parameter.

Yes: Specifies a cross section slice with starting and ending points defined by the X From Point, Y From Point, X To Point and Y To Point coordinate parameters below. The slice's start ("from") and end ("to") points are defined using a Cartesian coordinate system centered at the wafer center, with the primary fiducial facing downward. X has a 0 value at the wafer center, with negative values to the left and positive values to the right. Y has a 0 value at the wafer center, with negative values below it and positive values above it.

X From Point: With a cross section wafer map is selected with Cross Section—Point to Point active, this specifies the horizontal coordinate of the starting point for a Cross Section—Point to Point slice. A user would click inside the selection box and type the desired value, in millimeters from the wafer center.

Y From Point: With a cross section wafer map selected with Cross Section—Point to Point active, this specifies the vertical coordinate of the starting point for a Cross Section—Point to Point slice. A user would click inside the selection box and type the desired value, in millimeters from the wafer center.

X To Point: With a cross section wafer map selected with Cross Section—Point to Point active, this specifies the horizontal coordinate of the ending point for a Cross Section—Point to Point slice. A user would click inside the selection box and type the desired value, in millimeters from the wafer center.

Y To Point: With a cross section wafer map selected with Cross Section—Point to Point active, this specifies the vertical coordinate of the ending point for a Cross Section—Point to Point slice. A user would click inside the selection box and type the desired value, in millimeters from the wafer center.

Cross Section Autoscale: When the selected Wafer—Background Data is set to Cross Section and Cross Section Autoscale is set active, the four axis range parameters below Chart Autoscale allow a user to set custom X and Y axis minimum and maximum values in the displayed wafer map. A user would click the displayed current setting inside the selection box to toggle it to the opposite setting.

X Min, X Max: A user would click inside the selection boxes and type the desired X axis minimum and maximum values.

Y Min Y Max: A user would click inside the selection boxes and type the desired Y axis minimum and maximum values.

Threshold Autoscale: When the selected Wafer—Background Data is set to SQM Height and Threshold Autoscale is set active, the four axis range parameters below Chart Autoscale allow a user to set custom X and Y axis minimum and maximum values in the displayed wafer map. A user would click the displayed current setting inside the selection box to toggle it to the opposite setting.

Figure 29:
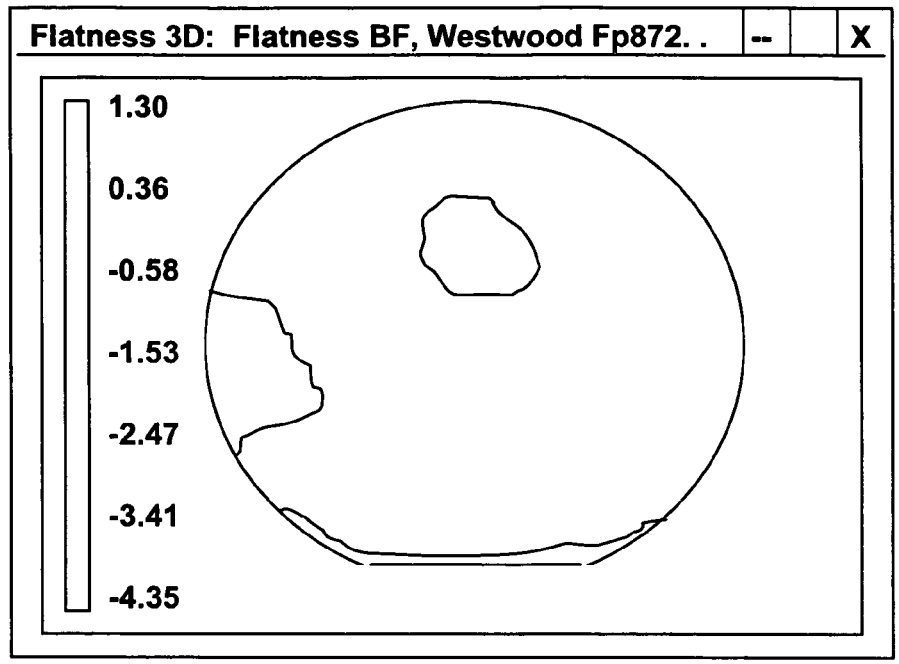
FIG. 29 is a block diagram of a screen showing the 3D Z-Scale option (set to 0.200) for the Layout Parameters tab shown in FIG. 17.
Figure 30:
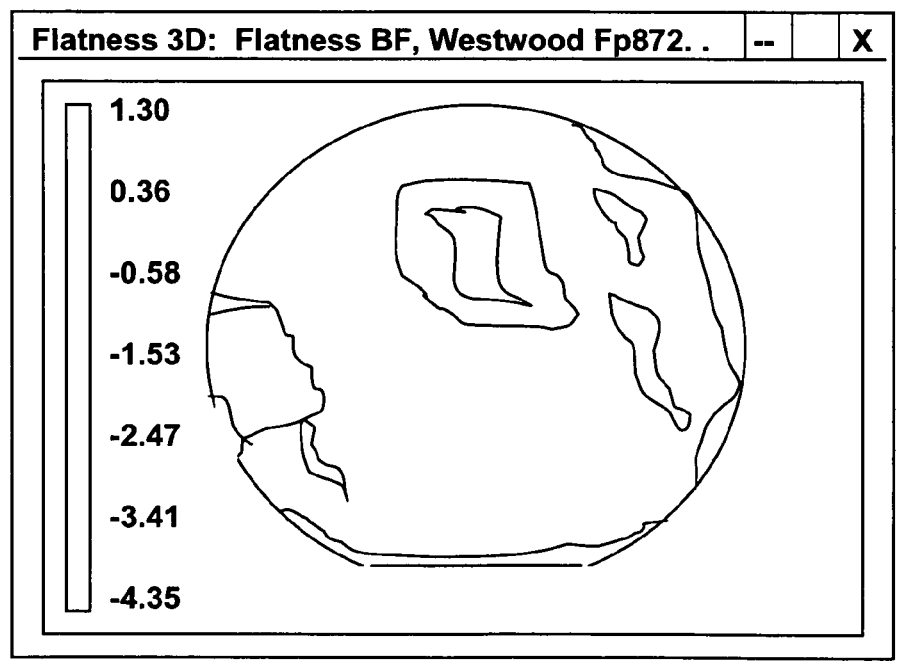
FIG. 30 is a block diagram of a screen showing the 3D Z-Scale option (set to 0.200) for the Layout Parameters tab shown in FIG. 17.

3D Z-Scale: Intended for 3D contour maps only, this parameter applies a scale factor to the surface point values to exaggerate the modeled surface as needed for improved readability. A user would click inside the selection box and type a value greater than 0 and less than or equal to 1. Higher values increase the exaggeration of the Z axis data. FIG. 29 shows a 3D Z-Scale set to 0.200, while FIG. 30 shows a 3D Z-Scale set to 1.000.

Defect Dot Size: This parameter controls the size of the displayed defects when Wafer—Defects Particles is set active. A user would double-click inside the selection box and select the desired size between 1 (Tiny) to 6 (Very Large).

Draw Defects To Size: This parameter controls whether the displayed defects are drawn relative to their actual size (Yes) or all drawn the same size (No). A user would click the displayed current setting inside the selection box to toggle it to the opposite setting.

Filter Defect Bins: This parameter allows the user to control the initial display of Defect Bins on the WaferMap. Any bin listed here will be filtered from the display, i.e. it will not be displayed. This is equivalent to unchecking the box next to the bin in the Legend Filter.

Filter Defect Bins (True Size): This parameter allows the user to control the initial display of Defect Bins (True Size) on the WaferMap. Any bin listed here will be filtered from the display, i.e. it will not be displayed. This is equivalent to unchecking the box next to the bin (true size) in the Legend Filter.

LCA—X Tolerance, LCA—Y Tolerance: These parameters are used for Lost Common Adder maps and counts, to determine how close a defect on the first wafer must be to a defect on the second wafer to be considered the same defect.

Defect Particle Limit: This parameter specifies the maximum particle count to use for composite defect wafer maps. Processing will stop if the total number of defects exceeds this value, avoiding lengthy delays and unnecessary resource consumption. Processing will stop if the wafer Scan Limit is reached first.

Scan Limit for Composites: This parameter specifies the maximum number of scans to use for composite wafer maps. Processing will stop if the total number of scans exceeds this value, avoiding lengthy delays and unnecessary resource consumption. For Defects, Processing will stop if the Defect Particle Limit is reached first.

Server System

Server system 04, which may comprise one or more servers, provides data storage and retrieval infrastructure (database and files), generic data storage code, data-type- and tool-specific data processing (converting the tools' data from the tools' formats to the format used by analysis system 06), data management (storage, purge, backup, restore), task execution (including scheduling and triggering), server executables, and server Configuration.

In the embodiments shown, server system 04 has a relational database management to facilitate the combination of metrology and inspection tools and the Configuration Application software, which operates as a unified interface to a set of largely independent server applications. In one embodiment, the server is a computer running Microsoft SQL Server, providing and maintaining a relational database using the SQL language, and the Configuration Application is a set of snap-ins to the Microsoft Management Console (MMC).

Server Executables

The two primary server executables are EventApp and TaskApp. These should be running at all times on an active server.

EventApp: The EventApp software implements the front-end of the server's data processing chain. As such, it runs the Tool Connects (which identifies incoming data and generates, but does not execute, tasks to process it), checks trigger conditions, and runs the Server's Scheduler. EventApp defers most of the processor-intensive work to the Server's Task Queue.

TaskApp: The TaskApp software implements that backend of the server's data processing chain, executing tasks from the Task Queue. Each instance of TaskApp can run 0 or more managed threads and 0 or more unmanaged threads. Managed threads run only managed tasks, which are tasks that are expected to run within a "reasonable" time. If a managed task takes too long, the system will notify any configured administrators via email. Unmanaged threads run only unmanaged tasks, which can take as long as they want to execute. Typically, only unusual activities will run unmanaged.

The most basic configuration is to run one instance of TaskApp running one managed and one unmanaged thread. This can run on the database server machine, or any other machine. Adding threads and instances of TaskApp (on additional machines) may increase system throughput, depending on the server machine(s) configuration(s).

Server Configuration

The Server Configuration is defined by the Server configuration Application software. Installing the Configuration Application is as follows: A Configuration Icon appears on the desktop screen of the display of the server system 04. This icon is a shortcut to the Config.msc file (ClientConfig.msc for client only install) located in the server system 04 file directory. The .msc file contains the snap-ins for the MMC. A user can double-click on the icon to start up the Configuration Application. If a client install is selected, the file may need to be associated with the application mmc.exe.

If the icon does not appear, a user should check the file directory to see if the file exists. If it is not found, the user will need to set-up the Configuration. To do this, the user brings up an MMC console by going to the Start menu, choosing Run, and running mmc.exe. In the MMC window, the user should go to the "Console" menu and choose "Add/Remove Snap-in . . . " This will pop up a dialog box. Choosing "Add . . . " will pop up another dialog box. On the new dialog, the user should select ServerConfig from the list of available snap-ins, click the "Add" button and then the "Close" button, and then click "OK" in the "Add/Remove Snap-in" dialog.

Figure 31:
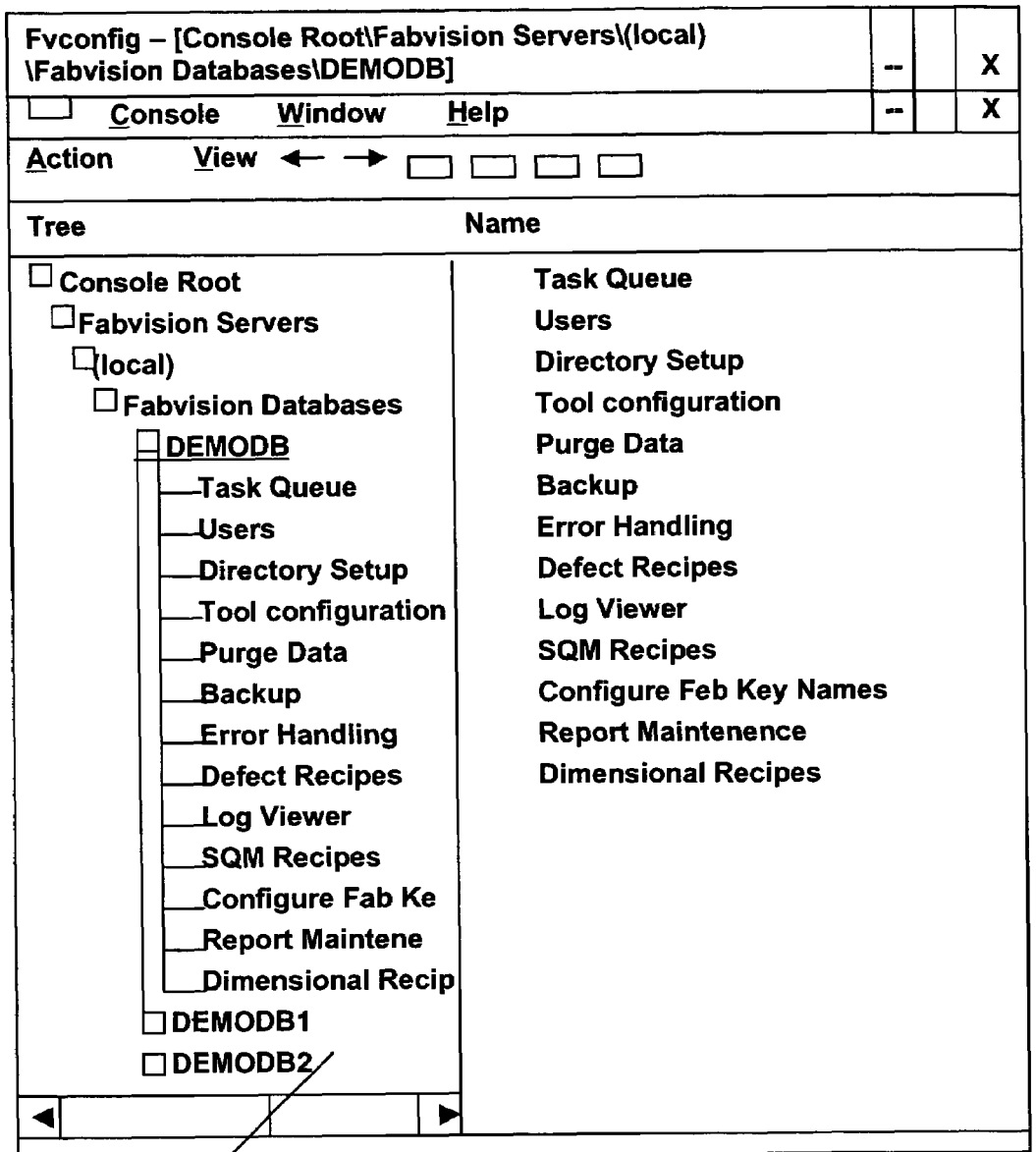
FIG. 31 is a block diagram of a screen showing the tree-view pane of a server configuration for the present invention.

With reference now to FIG. 31, at this point, the tree-view pane 110 of the MMC window (the left window pane), should show a node called "System Servers" below the node "Console Root". The user should right-click on the "System Servers" folder and choose the "Add Server . . . " option, and then enter the name of the desired server, along with a login and password. If MMC is being run on the server to be configured, a user should enter its name as "(local)").

To be sure that the configuration modules have all been installed properly, the user should expand the "System Servers" node, which should reveal a node for the server that was just added. Expanding the server node shows a node called "System Databases". If any databases have been created on the chosen server, expanding this node should list them by name. Expanding a database should show the following list of nodes: Directory Setup, Log Viewer, Configure Fab Key Names, Purge Data, Report Maintenance, Tool Configuration, Users, Task Queue, Backup, Error Handling, Dimensional Recipes. In addition, users of the Defect and/or SQM features will see nodes for Defect Recipes and/or SQM Recipes.

Once the server console has been set up, the configuration may be saved by the following procedure:

Maximize the console root window by clicking on the box in the upper right hand corner of the window.

Go to Console menu and select options.

Under console mode, select User mode-full access.

Check the box that says "Do not save changes to this console." Click "ok."

Go to the Console menu again and select "Save as . . . " Save the file in the directory called \System, with the name Config.msc.

Create a shortcut to this file on the desktop for quick access.

The process detailed above creates a configuration application that permanently stores the login information entered during the "Add Server . . . " step. Thus, the user will not need to reenter login information each time the application is run. If this raises security concerns at the facility where the configuration application is installed, a user may skip the step adding the server before saving the application. Doing so will require that the user perform the add server step each time he/she runs the application.

If an installation has multiple servers, they can all be supported by one configuration application. Users should simply perform the steps listed above for adding a server for each server. Users can also change the login used to access each server—right click on the name of the server in the tree view and choose "Properties . . . ", which will bring up a dialog asking for the login and password to use when accessing that server.

Configuration Application Features

The Configuration Application is a unified interface to a set of largely independent applications. The user navigates in the tree control of the MMC console to the desired server and database, and then chooses the desired task. This brings up a GUI in the right MMC panel that can be used to perform that task. The following sections describe how to perform each task using the associated GUI.

Figure 32:
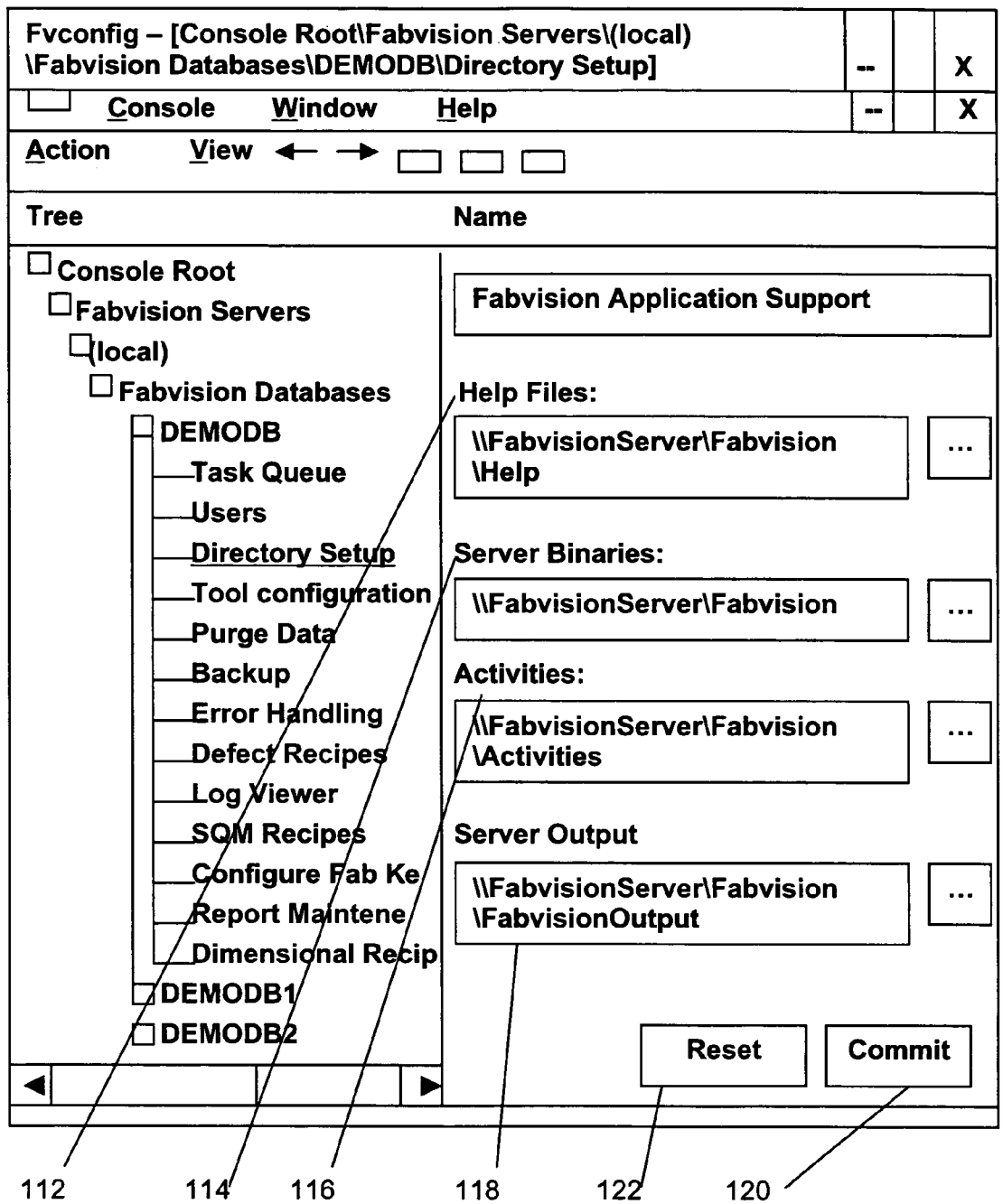
FIG. 32 is a block diagram of the Directory Setup screen for the server configuration of the present invention.

Directory Setup—As Shown in FIG. 32

The Directory Setup screen of FIG. 32 allows a user to configure the values of the following directories:

Help Directory 112 ("Help Files"): The directory containing help files.

Server Binaries Directory 114 ("Server Binaries"): The directory in which the server binaries are installed.

Activities Directory 116 ("Activities"): The directory used for storing activities created by Activity Manager.

Server Output Directory 118 ("Server Output "): The directory in which the server will store generated files that must be retained over a period of time. For example, reports generated by activities run on the server are retained for a configurable period of time in this directory. (To configure the lifetime of these files, "Purge Data" screen, described later in this document, is used).

Hitting the "Commit" 120 button seen in FIG. 32 will save changes, while hitting the "Reset" 122 button will discard them and reset the parameters to their previous setting.

Tool Configuration

Figure 33:
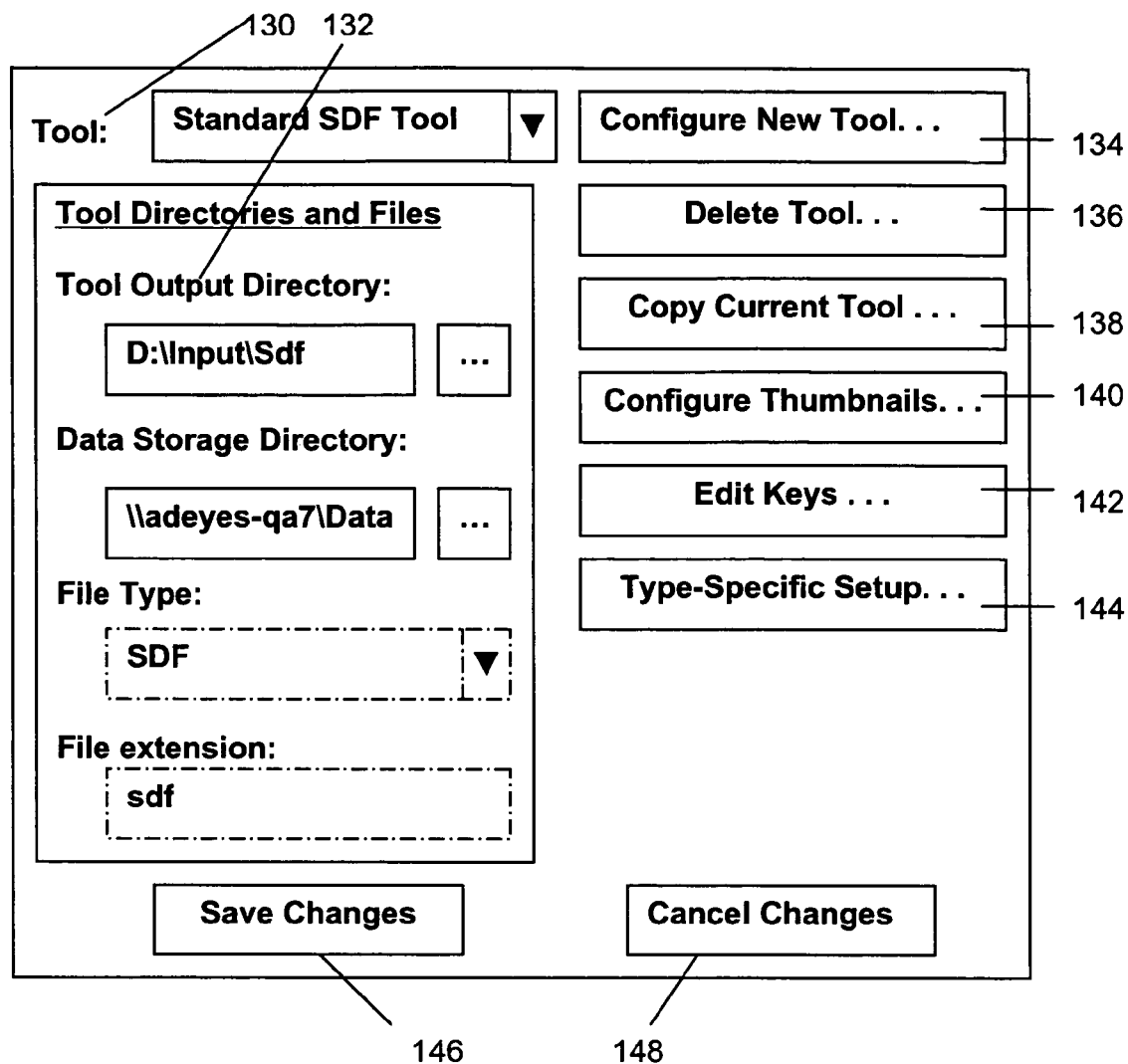
FIG. 33 is a block diagram of the Tool Configuration screen for the Configuration Application system of the present invention.

The Tool Configuration feature of the Configuration Application allows a user to edit, create, delete and setup Tool Connects, which define how data files are ingested into the Server system 04. The main Tool Configuration GUI, shown in FIG. 33, shows information about the currently selected tool, which be changed by choosing a different tool in the "Tool" 130 combo box at the top. Below this box is a set of edit boxes for Tool Directories and Files. In "Tool Output Directory" 132 box a user can select the directory in which data files is or will be written from the tool. The path to the directory may be local or remote.

In the Data Storage Directory box displays the directory into which data for this scan will be stored. The path for the Data Storage Directory will be stored in the database. It should be a UNC path so that users on client PCs can access the data on the server.

The lower two boxes indicate the "File Type" and "File Extension" of the data generated by the tool. These are set by default. Still in FIG. 33, to the right of the Tool Directories and Files are six buttons used for managing and setting up tools: "Configure New Tool" 134, "Delete Tool" 136, "Copy Current Tool" 138, "Configure Thumbnails" 140, "Edit Keys . . . " 142, and "Type-Specific Setup" 144. Each brings up a new dialog box. They will be discussed in turn below.

The two remaining buttons are "Save Changes" 146 and "Cancel Changes" 148. Note that any changes made in the Tool Configuration dialog, or any dialog within, will not be saved until "Save Changes" 146 is hit. Changes may be discarded by hitting the "Cancel Changes" 148 button. In the present embodiment, changes to a Tool Connect's configuration will not affect the server's data collection process until the EventApp application, described above, has been shutdown and restarted.

The following file types are supported:
Dimensional "THK/MEA/BW", which is for tools that generate .thk, .bw, mea, and text files, and "SDF", which is for tools that generate .sdf files.
Defect: CR8X tools (.SAI) and AWIS (.csv)
Nanatopography: AWIS (.SQM), CR8X (.PRN and HFP) and Nanomapper (.MAP).

Configure New Tool: Still in FIG. 33, to add a new tool connect, choose "Configure New Tool" 134 from the main GUI screen. This will bring up a wizard dialog for setting up a new tool connect. It will request the tool directory and file type information normally displayed on the main GUI, as well as key configuration information for each key, thumbnail configuration and the type-specific setup. All of the data entered with the Tool Configuration wizard can be modified after the Tool Connect has been created, with the exception of the Tool name and file type. When finished, a user would hit "Finish" and the new tool configuration will be saved or "Cancel" to cancel the wizard.

Deleting Tool: Still in FIG. 33, to delete a tool connect, simply select the tool to be deleted on the main GUI, and hit the "Delete Tool" 136 button. Once a tool has been deleted, it cannot be undeleted (except by re-entering all of its information from scratch).

Copy Current Tool: To make a new tool that has only minor differences from an existing tool, use the "Copy Current Tool" 138 option. A dialog box will appear showing the name of the tool to be copied (Source Tool) and asking for a new tool name and a new tool output directory. Enter these values and click ok to save the new tool. This new tool will retain the configurations of the source tool until it is chosen in the main GUI and edited. This option is useful for setting up multiple tools of the same type.

Figure 34:
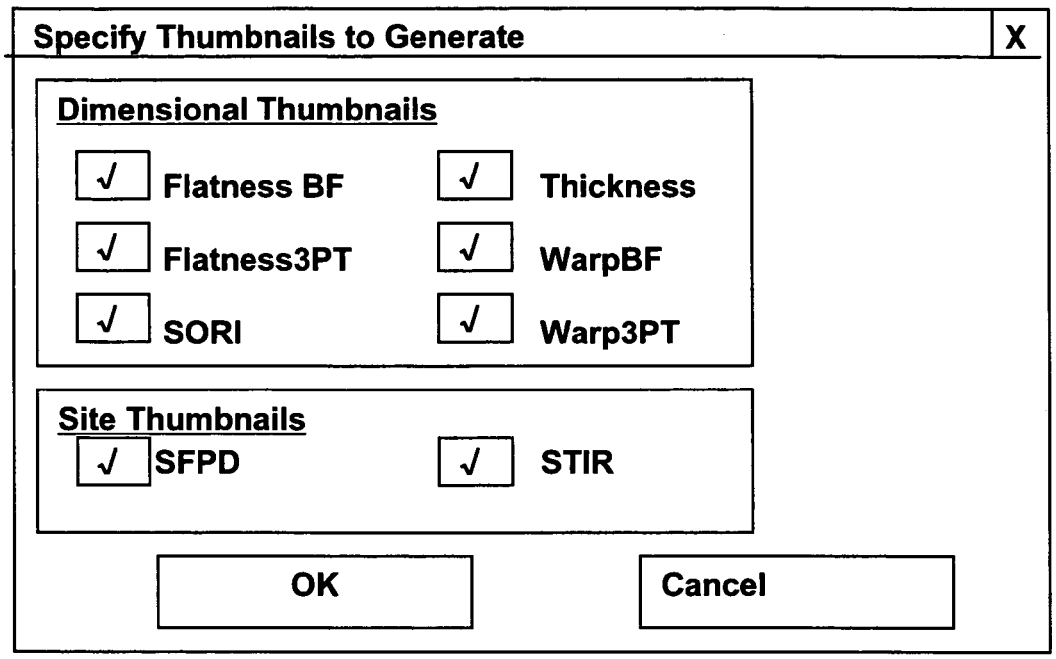
FIG. 34 is a block diagram of a screen for specifying thumbnail displays for dimensional files for the Configuration Application system of the present invention.
Figure 35:
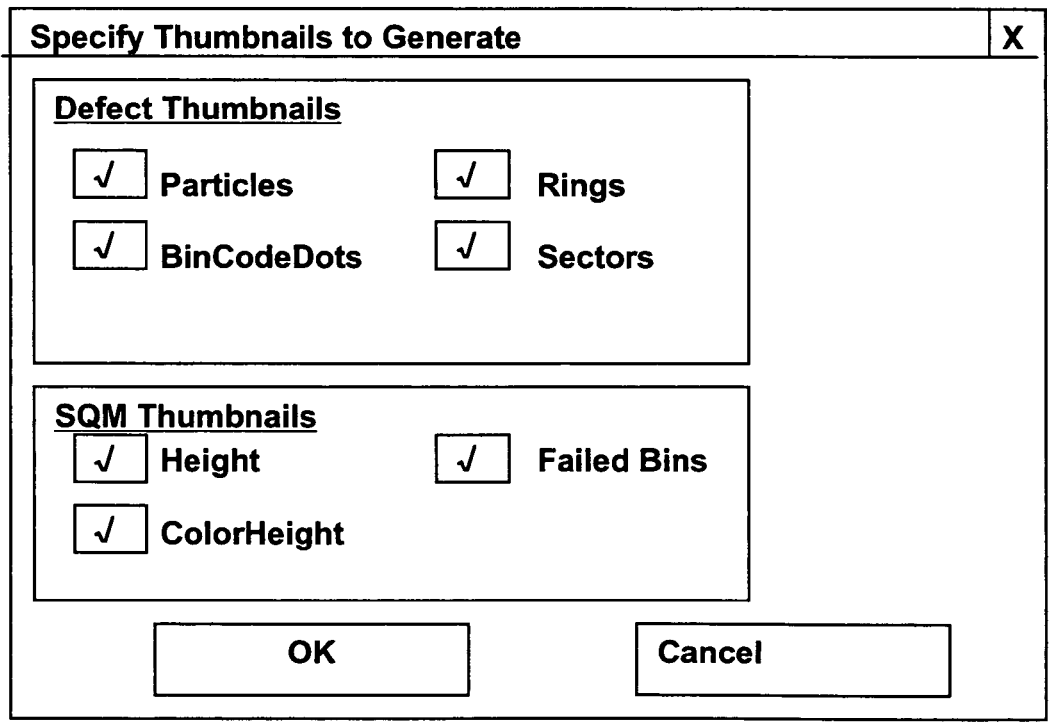
FIG. 35 is a block diagram of a screen for specifying thumbnail displays for defect files for the Configuration Application system of the present invention.

Configure Thumbnails: A set of thumbnails can be generated for each wafer scan. These thumbnails can be selected with the "Configure Thumbnails . . . " 140 button. Click on the button and a dialog box as shown in FIGS. 34 and 35 will appear with the available options for the given tool type. A user would check the box next to the thumbnails to be generated, or uncheck the box for those that are not required. Once a data file is ingested the chosen thumbnails will be generated. Each thumbnail is about 4-5 Kb in size so it is prudent to choose only the thumbnails that are required. However, note that if additional thumbnails are needed at a later time, the file must be re-ingested.

In the embodiments shown there are six dimensional and two site thumbnails available for Dimensional Files, three thumbnails are available for SQM files and four thumbnails are available for CR8X defect data. Other combinations can be created without deviating from the spirit of the present invention.

Figure 36:
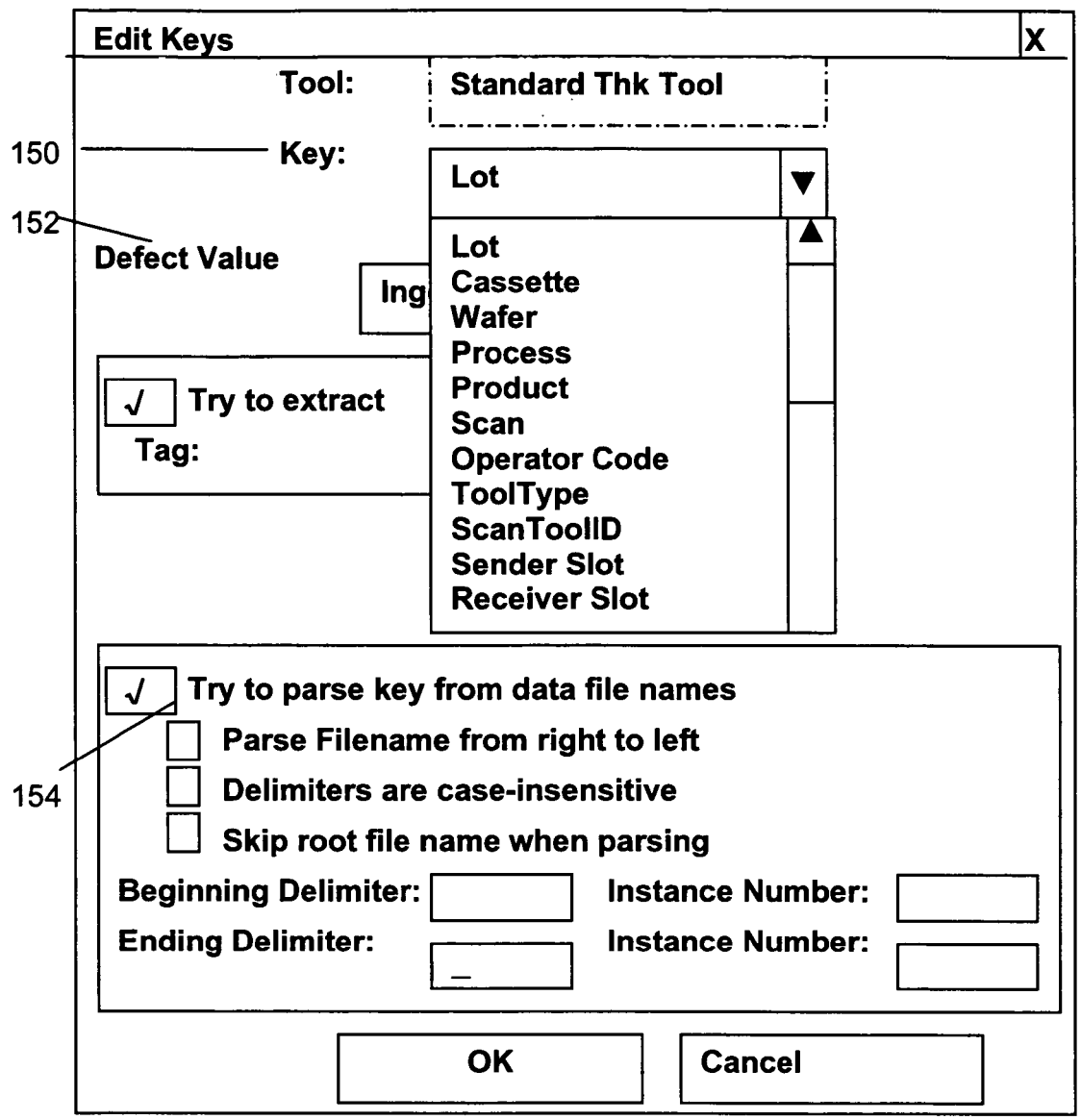
FIG. 36 is a block diagram of a screen for the Edit Keys capability for the Configuration Application system.

Editing Keys, as Shown in FIG. 36.

To edit the key configurations for the current tool, a user may hit the "Edit Keys" button, which will bring up another dialog. The key configurations are a way of specifying how certain information ("keys") about each scan that is loaded should be determined. This information (the wafer id, lot id, tool id, operator name, etc.) tends to be stored in a different place at every customer facility, so how to extract each key from the data files produced by each tool may be custom-configured.

The options on the edit keys dialog of FIG. 36 are dependent on the type of files generated by the tool. Regardless of the file types, there is always a combo box near the top for selecting which key 150 to configure, and an entry field to specify a default value 152 for that key for the specified tool. The default value is required, and will be used as the value for the current key on the current tool whenever a better value cannot be found. For the THK/BW/MEA, the SDF, .CSV (AWIS) and the SAI file type, a user may specify how to extract the key from the scan file and/or parse from the file name of the .thk, .sdf or .sai file as it comes off the tool. For the AWIS (.SQM) and Nanomapper file types, the key values can be parsed from the files, but the option to extract a key value from the scan file is not available for these file types.

Edit Keys for Dimensional Tools

To specify how to extract the key from the scan file, check the "Try to extract from scan file" box, and fill in the "Tag" field. For dimensional data files, the tag is the value of the tag in the text file that precedes the value to be extracted. For example, specifying a text tag of "Plant Order" indicates that the value of the current key should be determined by finding the tag "Plant Order" in the text file, and extracting the value stored there: if the line in the .text file that starts with "Plant Order" looks like "Plant Order foo", then the key value will be set to "foo". Key values for the .SAI and .CSV file type must be entered by hand; there is no pull-down menu. In this case it is a keyword (not a tag) that is found in the comment fields of the file. The keyword can be anything; It is setup on the tool. The value for each keyword, with the exception of date/time in SAI files, is entered by the tool operator on a lot-by-lot basis. Date/time is always one of the SAI keywords and its value is entered automatically.

Still in FIG. 36, as mentioned above, a user may also specify that a key's value may be extracted from the name of the file generated by the tool. A user does so by checking "Try to parse key from data file names" 154 and filling in the "Beginning Delimiter", "Ending Delimiter", and their associated instance numbers, and selecting any of the three check box options (Parse filename from right to left, Delimiters are case-insensitive, and Skip root filename when parsing) that are required.

The beginning delimiter specifies a string that immediately precedes the key in the file name, and the beginning delimiter instance number specifies which instance of the beginning delimiter indicates the beginning of the key.

When the "Parse filename from right to left" option is not selected, delimiter instances are counted from the left, meaning that the instance'th instance of the delimiter, counting from the left, indicates the beginning of the key value. For example, if the beginning delimiter is "_" and the instance number is 2, then the key value starts immediately after the second "_" in the file name.

Similarly, the ending delimiter specifies the string that occurs immediately after the key in the file name. When parsing from left to right, the ending delimiter instance number specifies which instance of the ending delimiter, counting from the beginning of the key, not the file name, indicates the end of the key. Both the beginning delimiter and the ending delimiter may be empty strings (""). An empty beginning delimiter indicates that the key starts at the beginning of the file name. An empty ending delimiter indicates that the key ends at the end of the file name.

instance'th instance of the end delimiter. This indicates where the key ends. Parsing then proceeds to the left until reaching the begin delimiter instance'th instance of the begin delimiter, which indicates the beginning of the key. (Analogous to forward parsing, the begin delimiter instance number counts from the end of key in this case, not from the end of the file name).

By default, delimiter names are case sensitive. Thus, a delimiter specified as "p" will not match the character "P" in the actual filename. To change this behavior, simply select the "Delimiters are case-insensitive" check box.

Finally, for left-to-right parsing only, a user may select the "Skip root filename when parsing" option. In this case, the initial part of the file name equal to root file name for the current batch of .thk/.mea/.bw files (as indicated in the text file) is ignored, and then the file name is parsed as it normally would, using <delim> as the beginning delimiter. Consider the file name TEST18__002__00003.thk, where the root file name, as given in TEST18.text, is TEST18. The following table lists some possible configuration values and the resulting key values:

| Beginning Delimiter | Instance # | Ending Delimiter | Instance # | Parse Right To Left | Case Insensitive | Skip root file name | Key Value |
|---|---|---|---|---|---|---|---|
| _ | 1 | _ | 1 | False | False | False | 002 |
| _ | 1 | . | 1 | False | False | False | 002__00003 |
| _ | 2 | . | 1 | False | False | False | 00003 |
| _ | 1 | _ | 1 | False | False | True | 002 |
| (blank) | 1 | _ | 1 | False | false | False | TEST18 |
| _ | 1 | . | 1 | True | False | False | 00003 |
| _ | 2 | . | 1 | True | False | False | 002__00003 |
| (blank) | 1 | _ | 2 | True | False | False | TEST18 |

Now consider the file name MyLotWithwsAndpsAndPsW5p2.sdf. The following table lists possible configurations and resulting key values:

| Beginning Delimiter | Instance # | Ending Delimiter | Instance # | Parse Right To Left | Case Insensitive | Skip root file name | Key Value |
|---|---|---|---|---|---|---|---|
| W | 1 | P | 1 | False | False | False | ithwsAndpsAnd |
| W | 1 | P | 1 | False | True | False | ithwsAnd |
| w | 1 | p | 1 | False | False | False | sAnd |
| W | 2 | P | 2 | False | True | False | sAndpsAnd |
| w | 1 | p | 1 | True | True | False | 5 |
| W | 2 | P | 1 | True | True | False | sAndpsAndPsW5 |
| P | 1 | . | 1 | True | True | False | 2 |
| (blank) | 1 | W | 2 | True | False | False | MyLot |

The three check box options are used to modify the basic behavior of the parser. If the "Parse filename from right to left" option is selected, then parsing proceeds right to left rather than left to right. The beginning delimiter still indicates the delimiter to the left of the key, and the ending delimiter the delimiter to the right of the key. However, the key is discovered as follows: parsing starts at the right of the filename, moving left until hitting the end delimiter As one final example, consider the file name 823L1_EP6B__003__00004.thk, with a root file name of 823L1_EP6B. If the beginning delimiter is "_", the beginning delimiter instance #1, the ending delimiter "_", the ending delimiter instance #1, and "Skip root filename when parsing" is true, then the key is "003".

Note that any changes made in the "Edit Keys" dialog will not be saved until "Save Changes" is hit on the main dialog. Hitting "Cancel Changes" on the main dialog discards changes.

Type-specific Setup

Different tools require unique parameter settings. These are contained in the Type-Specific Setup. For dimensional tools using either THK/BW/MEA or SDF files, click on this button to choose recipe(s). For AWIS and Nanomapper tools, use the Type-Specific Setup to set the parameters for SQM. For CR8X tools, the Type-Specific Setup is used to set the parameters for both SQM and Defect file processing.

Figure 37:
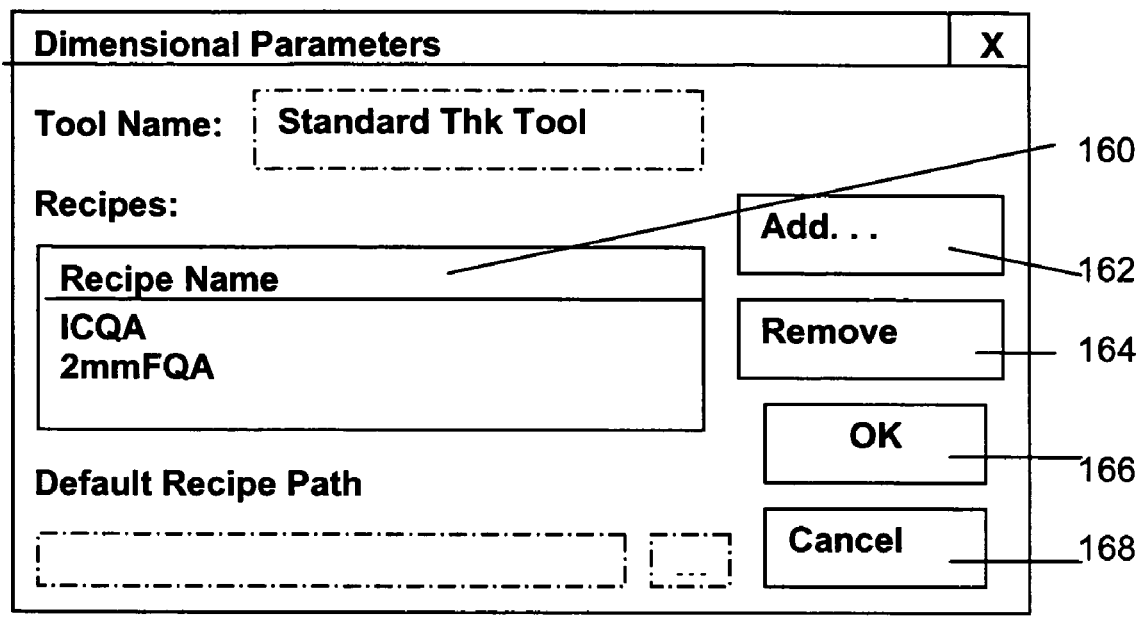
FIG. 37 is a block diagram of a Dimensional Parameters screen for setting up dimensional tools using the Configuration Application system.

Dimensional Type-Specific Setup: Choose a dimensional tool from the tool pulldown menu and click on Type-Specific Setup. A dialog box, such as the one shown in FIG. 37, will appear with a list of available Recipe Names 160. Click on Add 162 to choose a new recipe. To add recipes to the list of available Recipe Names, go to the Dimensional Recipes node. To remove a recipe from the main list, select it by highlighting the name and clicking on the "Remove" 164 button. The number of recipes added is user-specified, but each recipe is like performing an additional scan of the wafer, i.e. summary data and thumbnails will be generated for each recipe, and each requires additional processing time and disk space. A special case is when Default is chosen as a recipe; the recipe that the tool was scanned with is used, but, in order to know where the recipe is the path must be specified in the "Default Recipe Path" field.

NanoMapper Type-Specific Setup.: Choose a NanoMapper tool from the tool pull-down menu and click on Type-Specific Setup to set the nanotopography parameters for the tool. A dialog box will appear for setting the following: Staging Directory, Archive Directory (if the Archive Incoming Raw Data Files box is checked) and the wafer diameter. Finally, there is a selection box for the recipe. A list of recipes that are currently selected will appear and can be added by clicking on the "Add . . . " button. A box will appear with available recipes. Use the pull-down menu to select a recipe and click ok to add it to the list. (To add new recipes to the pull-down menu of available recipes, use the nanotopography Recipes node which is described below). To remove a recipe from the list, select it by highlighting the name and clicking on the "Remove" button.

Figure 38:
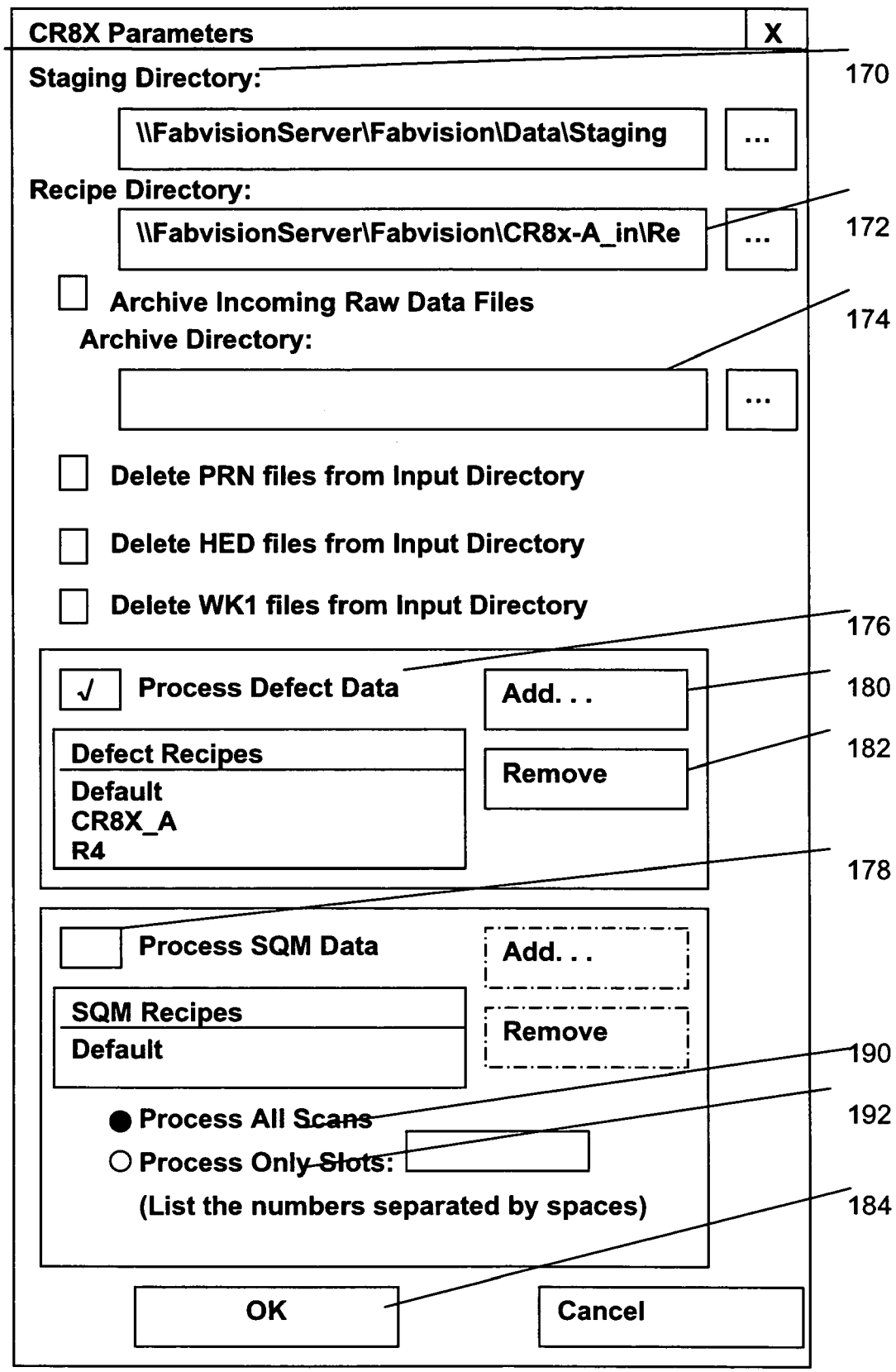
FIG. 38 is a block diagram of a Nanotopography Parameters screen for setting up nanotopography tools using the Configuration Application system.

CR8X Type-Specific Setup: As shown in FIG. 38, a user would choose a CR8X tool from the tool pull-down menu and click on Type-Specific Setup to set the nanotopography and Defect parameters for the tool. A dialog box such as that shown in FIG. 38 will appear for setting the following: Staging Directory 170, Recipe Directory 172 and Archive Directory 173 (if the Archive Incoming Raw Data Files box is checked). Below this there are two check boxes, one to select Defect file 176 processing, the other to select SQM file processing 178. Turn either of these on or off for the current tool. Select a recipe for each box that is checked and turned on. Click on the "Add . . . " 180 button and select a recipe from the pull-down menu. Click "Ok" 184 and the recipe will be added to the list.

To add new recipes to the pull-down menu of available recipes, a user would use the Defect Recipes node and/or the nanotopography Recipes node, both of which are described in below. To remove a recipe from the list, select it by highlighting the name and clicking on the "Remove" 182 button. The recipe directory indicates the location of the recipe file that comes from the tool. To process files using this recipe, choose default under Defect and/or nanotopography recipes. Finally, select either "Process all scans" 190 or "Process only from slots:" 192. If "Process only from slots:" 192 is chosen, the slot numbers of the files to be processed must be entered. The format is a list of slot numbers separated by spaces. The value for the slot number comes from the edit key value for "sender slot".

Figure 39:
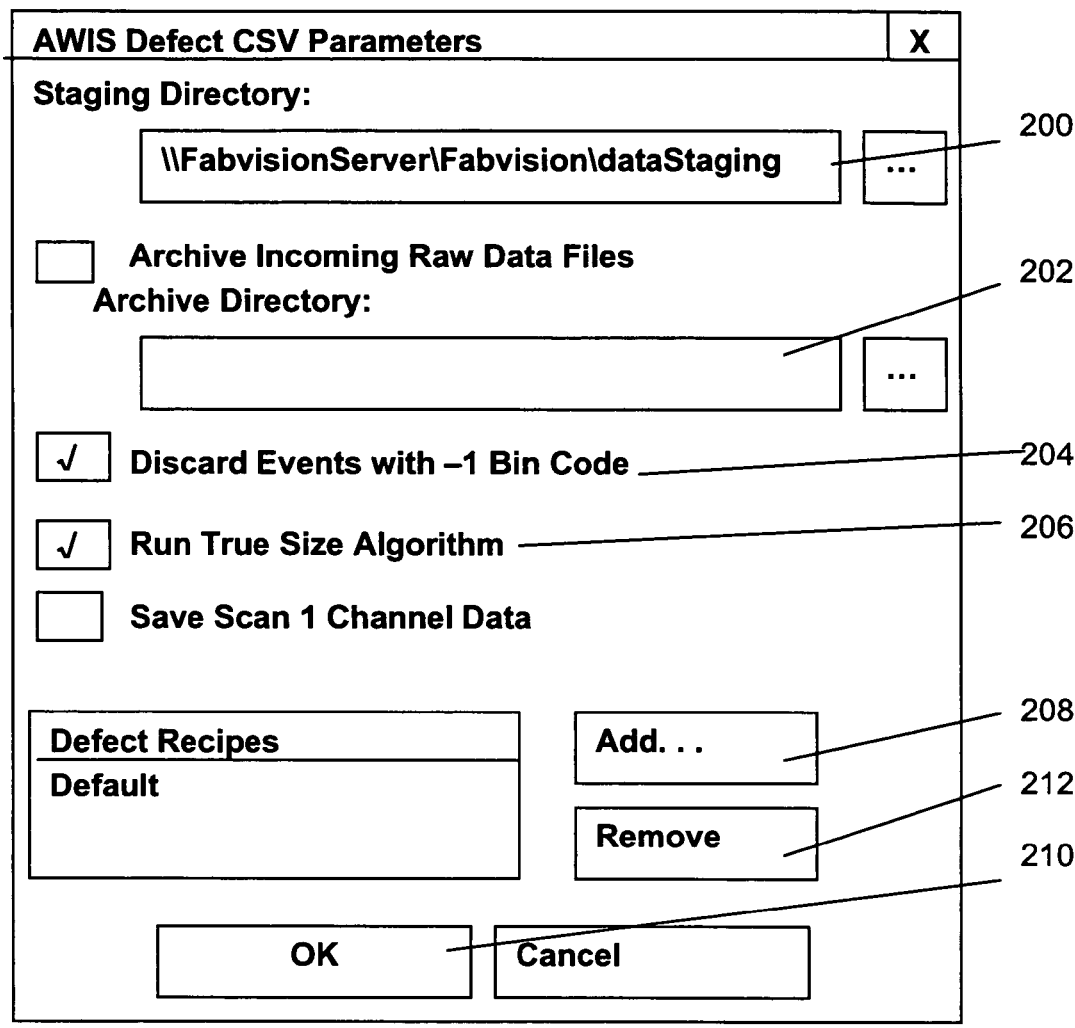
FIG. 39 is a block diagram of a Defects Parameters screen for setting up defect inspection tools using the Configuration Application system.

AWIS Defect CSV Type-Specific Setup: The AWIS system is available from ADE Corporation of Westwood, Mass. A user would choose an AWIS Defect—CSV tool from the tool pull-down menu and click on Type-Specific Setup to set the Defect parameters for the tool. The dialog box of FIG. 39 will appear for setting the following: Staging Directory 200, and Archive Directory 202 (if the Archive Incoming Raw Data Files box is checked). Below this there are two check boxes, one to discard events with −1 bin code 204, the other to run the True Size Algorithm 206 (for Thin Films Tools). Click on the "Add . . . " 208 button and select a recipe from the pull-down menu. Click "Ok" 210 and the recipe will be added to the list. (To add new recipes to the pull-down menu of available recipes, use the Defect Recipes node, described below). To remove a recipe from the list, select it by highlighting the name and clicking on the "Remove" 212 button. Choosing the True Size Algorithm 206 may require setting up a True Size Bin Set in the Defect Recipes node.

Defect Recipes

Recipes for processing Defect data files are created and edited using the Defect node of the server system 04 GUI. The node is divided into two sections:.General and Configuration Sets. Changes to the recipe are saved by clicking on the "Commit" button. A user would use the "Reset" button to discard any changes made since the last time "Commit" was hit.

General

Figure 40:
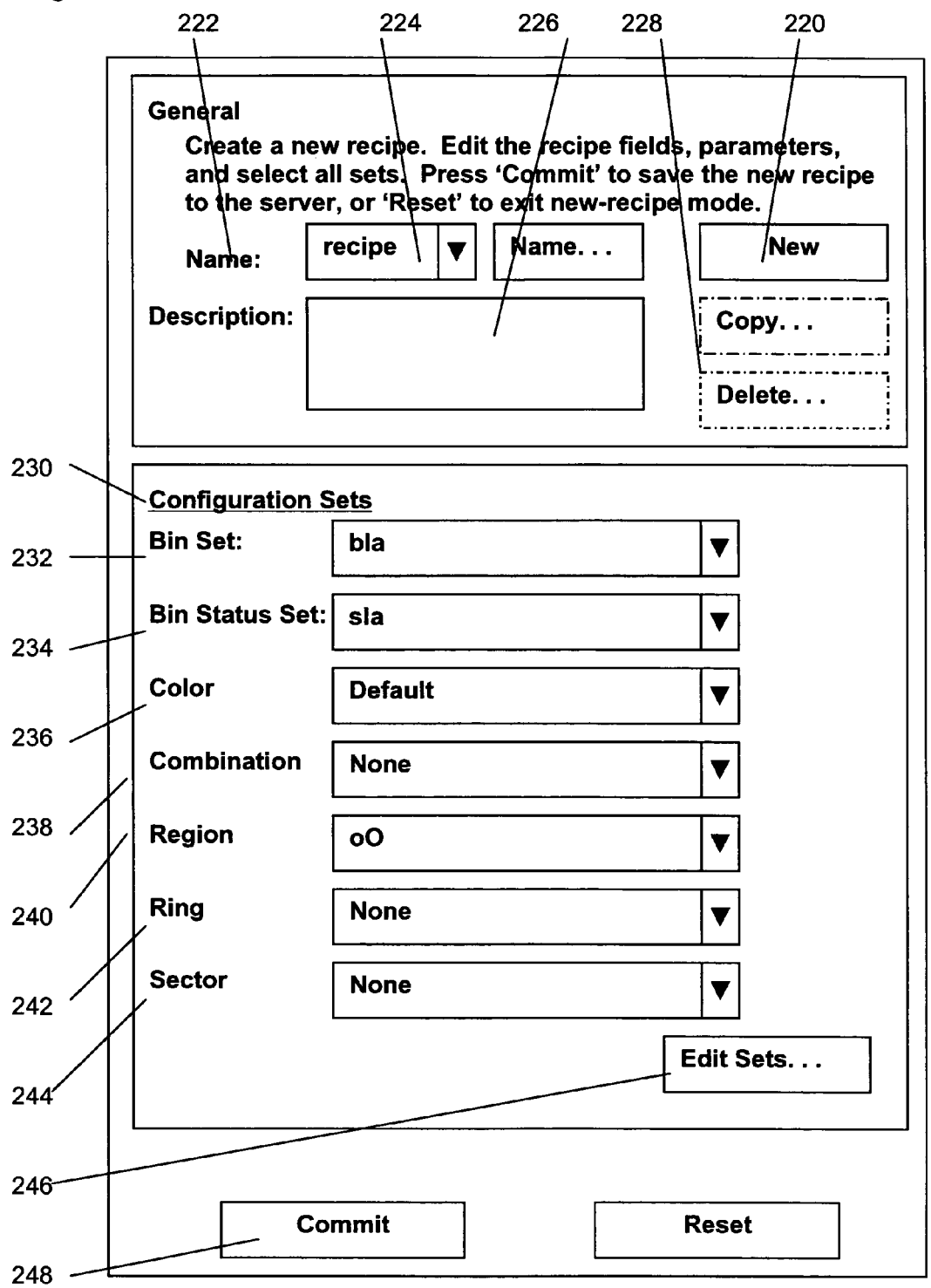
FIG. 40 is a block diagram of a Defects Recipe screen for creating new defect recipes using the Configuration Application system.

Defect recipes are stored in the database of server system 04. Recipes are created and edited in draft mode as shown in FIG. 40. They can be left in draft mode, where they are available for use in analysis system 06 during recalculation. However, recipes in draft mode are not available for tool connects, i.e. for the ingest of data. Recipes need to be taken out of draft mode (by un-checking the draft box) for use in ingesting. Here, they are effectively "read only". Non-draft recipes are available for use in both the client and the tool connects.

Still in FIG. 40, to create a new recipe, either click on "New" 220 or choose a recipe from the pull-down menu and select "Copy . . . ". In both cases a dialog box will appear asking the user to input the name of the new recipe.

New or copied recipes are automatically placed into draft mode so they can be edited. Once a recipe is taken out of draft mode and the "Commit" button has been hit, it cannot be placed back into draft mode.

The name of a recipe is changed by hitting the "Name . . . " 222 button. Enter a new name in the dialog box and hit "Ok. The name of ANY recipe can be changed, even one that has been taken out of draft mode. Enter a description for each new recipe in the "Description" 226 box. Note, in the embodiments shown, the server system 04 will not check for duplicate recipes or sets in this node of the MMC. Before creating a new recipe, check the properties of the existing recipes.

Still in FIG. 40, recipes can be deleted by using the "Delete" 228 button. Note: Recipes that are currently being used in a tool configuration cannot be deleted. Recipes that are referenced by any scan currently stored in the database also cannot be deleted.

Recipes labeled "Empty" and "Default" are available in the "Type-specific setup" for tool configurations and in the client via the recipes menu. These recipes are not true recipes since they cannot be edited in the Defect Recipes node. Rather, these recipes indicate whether certain processing algorithms should be executed. The "Empty" setting indicates that no recipe algorithms should be processed. The "Default" setting indicates that recipe with which the wafer was scanned on the tool should be used. That tool recipe should be located in the recipes directory at the time the files are ingested into the database. The tool recipe is read and a recipe, renamed with a database recipe name, is stored in the database to save the configuration information. When files are ingested using the "Default" recipe, server system 04 checks to see if a copy of the tool recipe has already been saved in the database and lists the database recipe name as the Defect Recipe for this scan.

Configurations Sets

Still in FIG. 40, the "Configuration Sets" 230 section of the GUI is used to set up the recipe parameters. The "Bin Set" 232 and "Bin Status Set" 234 are typically set to default. These two sets can then be created from the bin set definition in the recipe and raw data files at ingest. The Bin 232 and Bin Status 234 Sets can be predefined by the user and selected in the recipe from the pulldown menus next to each set listing. Each Bin Status 234 set must be associated with a Bin Set. User may also choose the "none" option for both the Bin 232 and Bin Status 234 sets and the files will be ingested without any binning. The remaining sets, Color 236, Combination 238, Region 240, Ring 242 and Sector 244 can be set to none or default (currently these function identically) or they may be pre-defined by the user. To create new sets or view existing sets, use the "Edit Sets" button. Note: If a pre-defined Region 240, Ring 242 or Sector 244 set for a given recipe is chosen, a Color 236 Set for that recipe should also be defined and selected so that the defect density can be properly displayed on the wafer map.

Click on the "Edit Sets" 246 button and a dialog box will appear. Select the type of set the user wishes to edit from the pull-down menu adjacent to "Set:", i.e. Bin Set 232, Ring 242 Set, etc. For each set type, a list of available sets and a description of each set will be shown in the box below. Bin 232, Bin Status, 234 Color 236, Combination 238, Region 240, Ring 242 and Sector 244 Sets can be created, edited and/or viewed by selecting from pull-down menu in the Configuration Sets dialog box of FIG. 40. Selecting new or edit will bring up the edit dialog box for that set. See below for details on creating and editing these sets. Each set should be edited in draft mode and taken out of draft mode once all changes have been made. As with the recipe itself, once the set is taken out of draft mode, the set becomes read-only and no further changes can be made.

Once the general and configuration sets have been configured, click on "Commit" 248 to save the recipe.

Nanotopography Recipes

Recipes for processing and reprocessing of nanotopography data files are created and edited using the Nanotopography Recipes node of the server system 04 GUI. The node is divided into two sections: General and Configuration Sets. To save changes to a recipe, click on the "Commit" button. Use the "Reset" button to discard any changes e made since the last time "Commit" was hit.

General

Nanotopography recipes are stored in the main database 08 of the Server system 04. Recipes are created and edited in draft mode. They can be left in draft mode, where they are available for use in the client during recalculation. However, recipes in draft mode are not available for tool connects, i.e. for ingesting data. Recipes need to be taken out of draft mode (by un-checking the draft box) for use in ingesting.

Here they are effectively "read only". Non-draft recipes are available for use in both the client and the tool connects.

Nanotopography Recipes are illustrated in FIG. 41. To create a new recipe, a user would either click on "New" 250 or choose a recipe from the pull-down menu and select "Copy . . . " 252. In both cases a dialog box will appear asking for inputting of the name of the new recipe. New or copied recipes are automatically placed into draft mode so they can be edited. Once a recipe is taken out of draft mode and the "Commit" button has been hit, it cannot be placed back into draft mode. The name of a recipe may be changed by hitting the "Name . . . " 254 button. A user would enter a new name in the dialog box and hit "Ok". The name of ANY recipe can be changed, even one that has been taken out of draft mode. A user would enter a description for each new recipe in the "Description" 256 box.

Recipes can be deleted by using the "Delete" 258 button. Recipes that are currently being used in a tool configuration cannot be deleted. Recipes that are referenced by any scan currently stored in the database also cannot be deleted.

For Nanotopography Recipes there are two parameters that must be set for data processing. Click on the "Parameters . . . " 260 button and a dialog box will appear. Currently, there are two parameters that can be set here: CR8X emulation and Laser Mark Exclusion. Check the Yes/No box to set these two parameters: "Should CR8X emulation mode be used when processing scan data?" "Should laser mark exclusion be used when processing scan data?"

Configuration Sets

The "Configuration Sets" 260 section of the GUI is used to set up the recipe parameters. The "Bin Set" 262, "Bin Status Set", 264 "Calibration Set" 268 and "Exclusion Zone Set" 270 can be selected from the adjacent pull-down menus that contain all the sets currently available. To edit existing sets or create new sets, use the "Edit Sets" 272 button.

Still in FIG. 41, lick on the "Edit Sets" 272 button and a dialog box will appear. Select the type of set to edit from the pull-down menu adjacent to "Set:", i.e. Bin Set, Bin Status Set, Calibration Set or Exclusion Zone Set. For each set type, a list of available sets and a description of each set will be shown in the box below. A user can either create a new set, or select a current set and edit, delete or copy it. Selecting new or edit will bring up the edit dialog box for that set. See below for details on creating and editing these sets. Each set should be edited in draft mode and taken out of draft mode once all changes have been made. As with the recipe itself, once the set is taken out of draft mode, the set becomes read-only and no further changes can be made.

Once the general and configuration sets have been configured, click on "Commit" 274 to save the recipe.

Dimensional Recipes are shown in FIG. 42. Recipes for processing Dimensional recipes are created and edited using the Dimensional node of the Server system 04 GUI This node consists of a main dialog box listing the recipe name and the path to the recipe, as seen in FIG. 42.

In FIG. 42, click on New 280 to specify a new recipe name and path, or select a recipe and chose Edit 282 to modify the recipe name and/or path. The dialog shown in FIG. 43 will appear.

Enter the recipe name 272 and the path 276 for a recipe the user wishes to create and/or modify. Note: the recipe name must be included in the path. To Delete a recipe, highlight the recipe and chose "Delete". A recipe cannot be deleted if it is referenced by an existing scan in the database or if it is specified in the type-specific setup of a tool connect.

Purge Data

The Purge Data GUI shown in FIG. 44 allows the user to control the automatic, selective removal ("purging") of old data from the data store. The strategy may be input manually at any time or it may occur automatically at selected intervals of times, using a purge mask and an automated scheduling system. By defining one or more "purge masks", a user can specify what types of files are purged at what age. A user can specify how long to keep selected type of data for a selected tool by Customer, Product, Process, Lot, Wafer, and User Scan. Users may specify keeping certain data in a record or associated with it, and purging other data, such as temporary files. As an example, certain data in a record could be kept for 30 days, while associated thumbnails and scan files could be deleted after 10 days.

The main purge screen of FIG. 44 will display all active masks. By selecting the "New Mask" 280 or "Edit Mask" 282 buttons, the Edit/New Purge Mask screen shown in FIG. 45 will be displayed. Here a user can define what values for the keys (lot, process, etc) are to used for this mask, and a purge age for the different types of data (database, scan data, thumbnails). After a mask is defined, any scan data that matches the key definitions will be purged based on the age definitions of the different data types.

The data types of "Temp Data" and "Archived Data" are special cases. These do NOT use the key fields in the mask definition, only the file age parameter. The unused fields are grayed out whenever a Temp or Archived file age is defined. Each time purge is run (either by using the "Purge Now" 284 button shown in FIG. 44 or through the scheduler option), each purge mask in the list is evaluated and the appropriate files and records are deleted.

Purge also provides the option of monitoring disks to insure that they do not get too full. A user may select the drive letter to be monitored, in the "Max % Threshold" enter the maximum percentage of that drive that can be full before there is a problem, and optionally enter an email address to be sent a notification when a drive has exceeded its allowed threshold.

Still in FIG. 44, if a user wishes to have the system automatically purge all data meeting specified criteria, selecting the "Automatically perform purge" 288 check box and entering how often the user wishes this to occur (in days) and the desired time of day for the purge (ideally, the time of day should be when other system activities, both server and client, are at a minimum) provides an automatic purge.

Preferably, setting up automatic purge operations should be done on the server. Remotely setting up automatic purge operations is not recommended. Further, automatic purging cannot be configured remotely unless a periodic purge task has already been set up in the Windows NT scheduler.

In addition, manually executed purge operations may be performed by hitting the "Purge Now" 286 button. However, purge operations can be very time consuming (up to several hours when purging large amounts of data), and the configuration application will be unusable throughout the duration of a manually executed purge. Once a purge has begun, purge operations may be cancelled by "killing" the configuration application in the Windows NT Task Manager, which is not recommended.

The Purge Main GUI is shown in FIG. 47. The Purge Mask Definition GUI is illustrated in FIG. 45.

Archive/Restore

Figure 46:
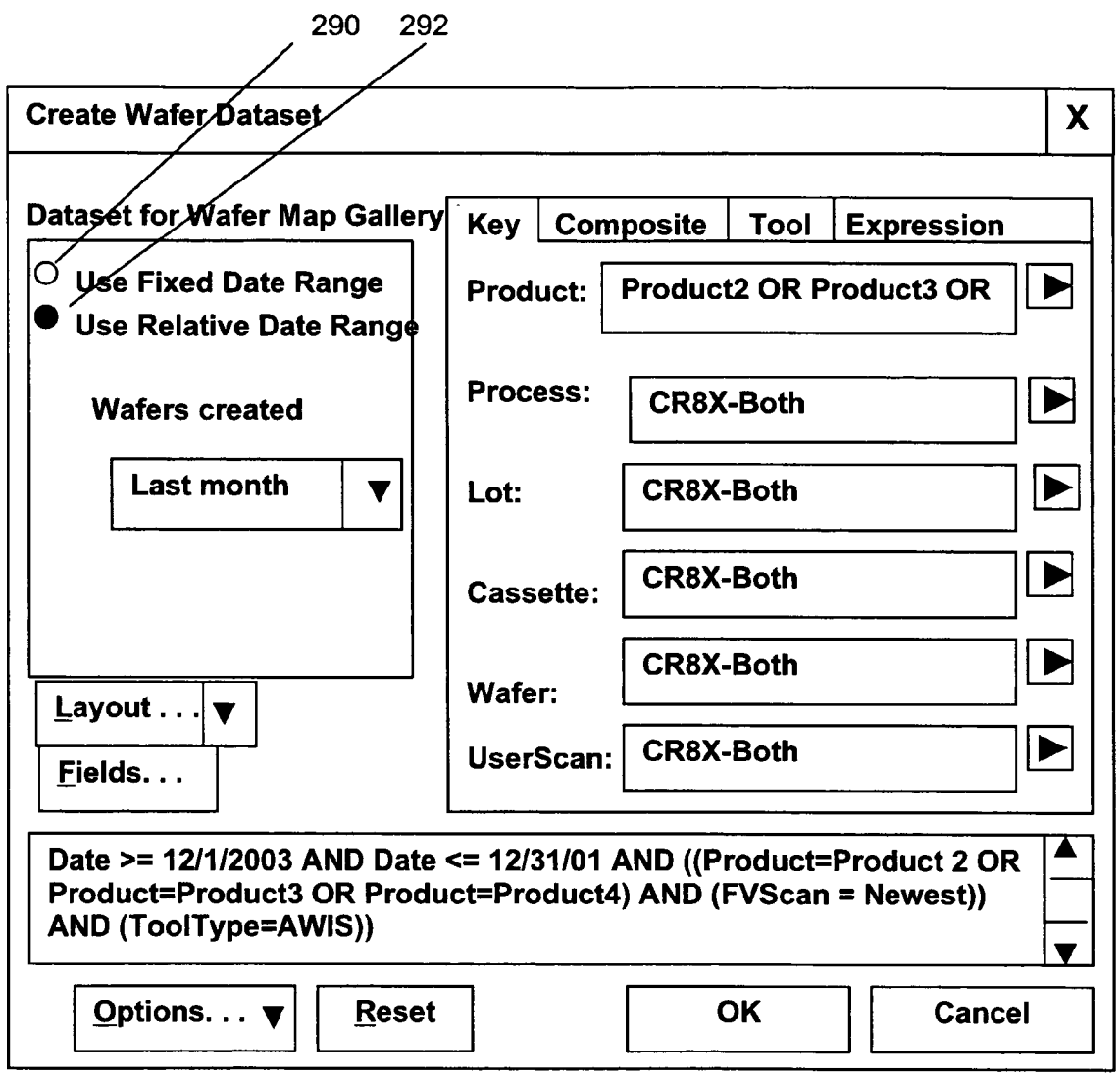
FIG. 46 is a block diagram of the Create Wafer Dataset screen for use in the Archive/Restore capability of the present invention.

Turning now to FIG. 46, with Local Archive, a user may archive selected type of data for a selected tool by Customer, Product, Process, Lot, Wafer, and User Scan, using a fixed date range or a relative date range, as shown in FIG. 46. Data so selected (Scan Files, dimensional or defect data, database records) may be backed up to DVD at any Data Analysis System by use of a DataTool Connect operating as an input to a DVD, or it may be transmitted to another integrated management system for additional review.

The following description of the archiving procedure will focus on archiving scan data, but it can equally apply to setup data, tool configurations, and layout definitions. Two categories of archiving are provided. The first is a manual archive where the user selects items in the gallery and is given the choice of an archive database name and path location. The second category is an automatic archive that will be an extension of the purge utility. Both of them archive the selected data to a zip file.

Manual Archiving

A dataset is loaded and displayed in the gallery using a query as described above. Selecting one or a group of items in the gallery, the user right clicks and chooses the "Archive" function.

Automatic Archiving

Figure 48:
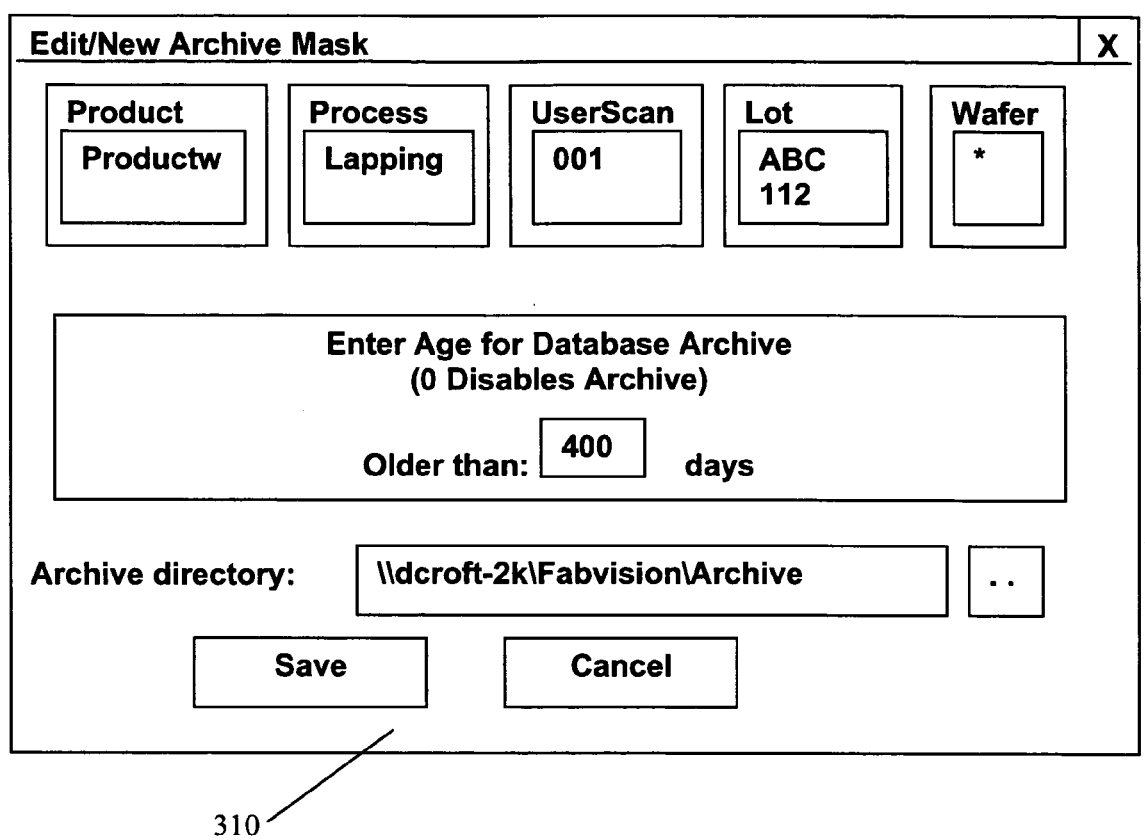
FIG. 48 is a block diagram of the Edit/New Archive Mask screen for editing or creating new Archive Masks.

Automatic archiving is defined with an archive mask, such as the one depicted in FIG. 48. A user opens the mask through the Purge/Archive screen of the Configuration application (shown in FIG. 47 as the New Archive Mask 302 button). A new archive mask, shown in FIG. 48, is created to capture all scans for the process desired.

The archive mask will be processed along with purge masks during scheduled automatic purge/archive activities. The next scheduled auto-purge/archive will process this new archive mask resulting in copying database information of the desired scans to an archive database.

Restoration of Archived Data

A tool configuration is used to restore archive files into a database. Configuration of this tool consists of designating a tool output directory that an event application monitors for archived .zip files. The Configuration Application has two software applications, EventApp and TaskApp, described below, that may be used to incorporate the archive data into the main database 08.

Archive/Restore Architecture

Archiving Data

The architecture for archiving is based on archiving scan data from the SQL server main database 08 to a Microsoft Access database. As noted above, archiving will be initiated either manually from the client by the user selecting items in the gallery or automatically by setting up archive masks.

If the archive is initiated manually from the client, the user supplies the name and path of the archive database. If initiated from the server using a mask, the name will be automatically generated from the mask keys while the path is part of the mask setup.

However initiated, the archive database is put into a temp directory along with associated scan files and thumbnail files and a copy of the dimensional recipes, if any. The entire contents of this temp directory are then zipped into one file; a filename is generated from the name of the archive database and placed in the path designated for the archive. The temp directory is then deleted.

The major components of archiving are: 1) creating a database using the Microsoft Access database system, 2) creating tables in the new database, and 3) copying all data associated with the scan, including associated scan and thumbnail files, into an archive.

Create the Database

Creation of the database will use a "Catalog" object that contains a "Create" method. A CreateArchiveDatabase method requires a database name and directory as inputs, defined by the user when archiving is performed manually or defined by the Server system 04 when archiving is performed automatically. A CreateArchiveDatabase is found in the IDBUtil interface. With manual archive, a dialog box opens, and the user enters an archive database name and path. When the user clicks "OK", an archive database is created of the database records associated with the selected scan. With automatic archive, the Server system 04 defines a database name and archive directory.

Create the Tables

All scan data archive databases will contain the same tables (see below). These tables will be created by a generic routine that, when provided with the SQL Server table name as an input, will generate a corresponding table in the database.

A SQL Server stored procedure "sp_columns" returns the column headings, column datatypes, and column data length. This information is used to generate the corresponding database tables. This approach will remove the requirement of keeping the table creation software in sync with version updates that might alter table definition.

It will be noted that tables are created in the archive database that mirror the corresponding tables in the main database 08. The table properties of column heading, datatype and data length are obtained using a SQL Server stored procedure "sp_help".

The archiving of Defect, Dimensional, and nanotopography scans require the creation and archiving of disparate table types. Creation of the archive database will add these three lists together and generate all the tables even though many will not be populated.

The following tables are required to archive Defect, Dimensional, and nanotopography scans:

Defect Scans: ProcessScan, DefectData, WaferClassification, WaferClassificationNames, ConsolidatedSummaries, DefectCodeSummary, DefectRecipes, BinSets, Bins, BinStatusSets, BinStatuses, TSBinSets, TSBins, RingSets, Rings, SectorSets, Sectors, UserDefRegionSets. UserDefinedRegions ClassificationCodeSets, ClassificationCodes, ClusterSets, Clusters, ColorSets, Colors, CombinationSets, Combinations, COPParams, and DefectRecipeProperties.

Dimensional Scans: ProcessScan, IMPData, Recipes, SiteMapParams

SQM Scans: ProcessScan, SQMData, SQMCodeSummary, SQM BinSets, SQM Bins, SQM StatusSets, SQM Statuses, SQMCalibrationSets, SQMCalibrations, ExclusionZoneSets, ExclusionZones, SQM RecipeProperties.

Copying the Data

Scan records to be archived all have a unique 'id': DefectDataID for defect scans, SQMDataID for nanotopography scans, and the combination of ProcessScanID and RecipeID for dimensional scans. IDBUtil has a procedure for accepting the unique ID's as defined by scan type, and then copying all associated data to the archived database. Associated scan files and thumbnail files are copied to an archive file directory in a temporary work area, using the same sub-directory structure and file names that the task manager created when the scan was ingested.

In the case of dimensional scans, each of which has a recipe associated therewith, the database record, as created above, or the recipe table, as created above, contains the path to the recipe being used. This path may be local or somewhere on the network. A copy of the recipe is copied into the temporary work area, and the path is updated to point to the location of the copied recipe.

Once the data is archived into the new database and associated file structure, it may be placed into a zip file. If the archiving is performed manually, a pop-up screen will be displayed requesting a location for storing the archive .zip file, which may be local or somewhere on the network. If the archiving is performed automatically, the location of the archive .zip file will be pre-defined, again local or somewhere on the network.

Restoration Of Archived Data

Restoration of archived data involves treating the archived scans as though they are scans from another tool in the analysis system 06. The "tool" in this case is an "Archive/Restore" tool having its own tool configuration, described in more detail below. The archived database (.zip) to be restored will be copied to the tool output directory to be processed by the EventApp software, which accesses the database in the tool output directory, and the TaskApp software, which works with the copy in the staging directory.

Instead of merely copying archive records back to corresponding tables in the main database 08, the Archive Restoration procedure actually pulls information from the archived database just as it does from other tool output files. Archived data is then added to the database as a new scan. Thus, the restoration is independent of the database version. Alternatively, instead of having to parse through an input file for the key values, EventApp obtains the values directly from ProcessScan table.

EventApp processes Defect and SQM Recipes by loading the required variables from the archive database and through existing software, and determining if the recipe already exists or a new one needs to be created. Dimensional recipes are restored from the archived copy; and the path to the recipe altered in the database.

For every archived scan, EventApp adds a task to the Task Queue of the Server system 04 and places a copy of the archive database in the staging directory.

The DoTask handler in the Task Queue activates TaskApp processing. The DoTask handler task processes data contained in the archive database in the same manner as it processes data in any input file, running algorithms on the acquired data, loading algorithm results into the various tables, and creating XML and thumbnail files.

A new field "RestoredDateTime" is added to the IMPData, DefectData, and SQMData tables. This field serves two purposes, 1) If the field is 'not NULL', then it will be known that the associated scan is a restored scan. 2) Purge masks can use this field to determine whether or not to purge the scan (n days after restored date).

Archive/Restore User Interface

There are two main components of the Archive/Restore user interface. The first component is setting up an archive mask while the second is configuring an archive/restore tool for restoring archived information.

Archive Mask

The purge mask utility of the Configuration application includes both purge masks and archive masks as shown in FIG. 47. In FIG. 47, the mask type 304 indicates either "Archive" or "Purge". The last column 306 indicates where the archive file will be stored. A new control, "Restored Records Age" 308 allows the user to control how long restored files are kept. Clicking on the "New Archive Mask" 300 button creates a new archive mask. The dialog box shown in FIG. 48 is displayed. Clicking on "Save" will add the specified mask to the database, close the dialog box, and display the new mask in the "Purge/Archive Data" screen of FIG. 47.

Archive/Restore Tool Config

Figure 49:
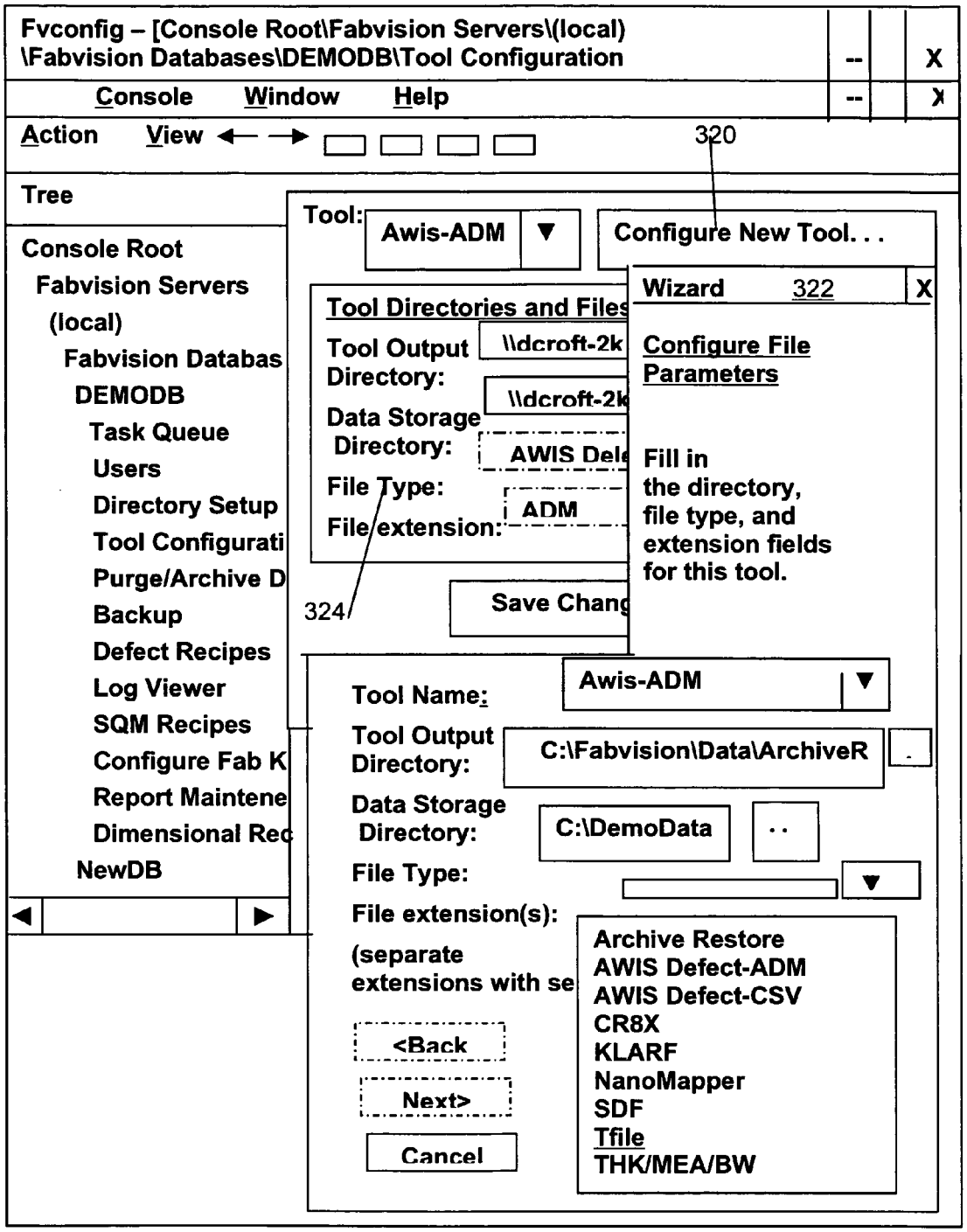
FIG. 49 is a block diagram of a screen showing the tree-view pane of a server configuration, exploded to show the details a tool configuration for archive data restoration, along with a screen for a wizard for use in setting up the tool configuration for archive data restoration.
Figure 50:
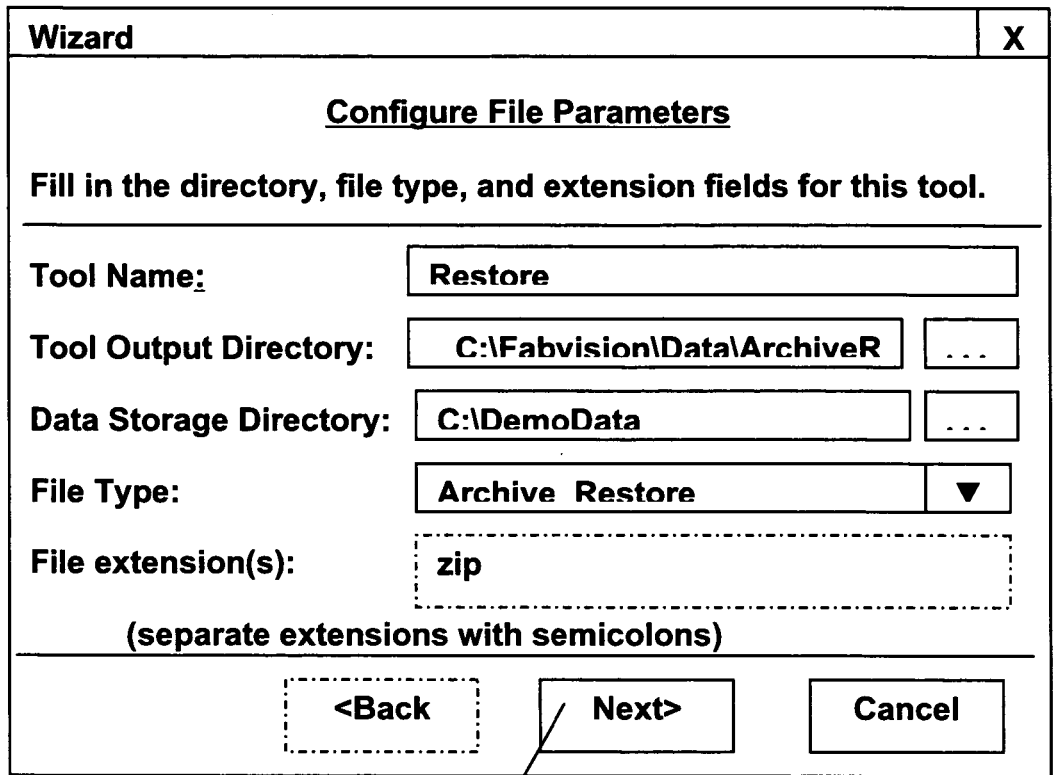
FIG. 50 is a block diagram for another screen for the wizard for use in setting up a tool configuration for archive data restoration.
Figure 51:
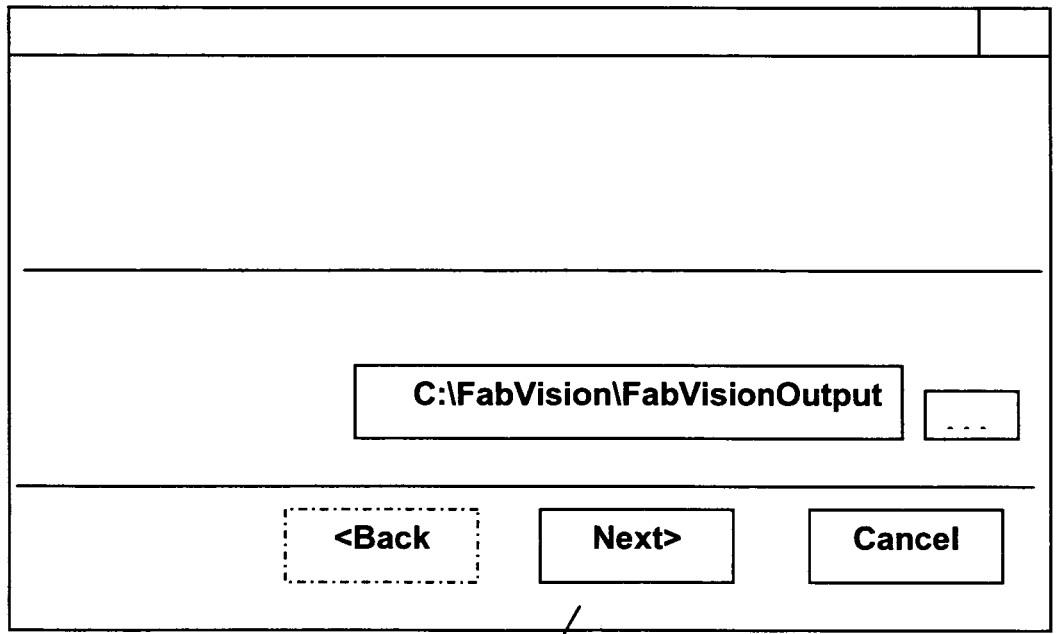
FIG. 51 is a block diagram of a screen for the wizard for use in setting up a tool configuration for archive data restoration.
Figure 52:
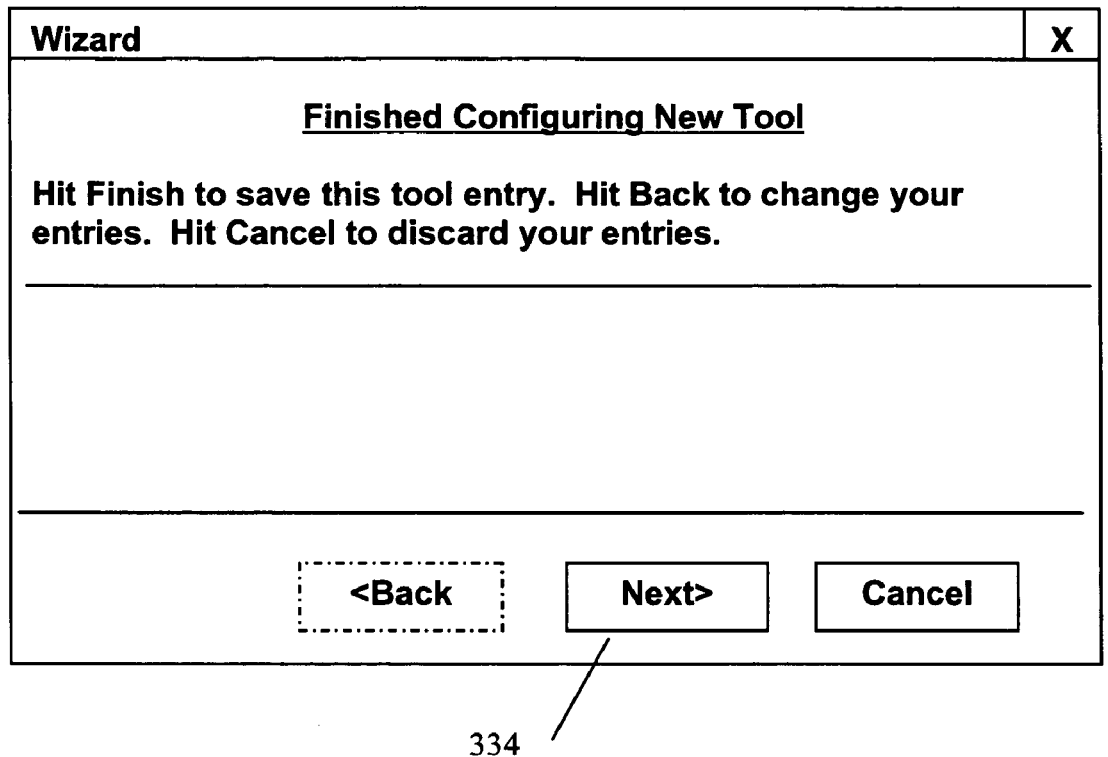
FIG. 52 is a block diagram of the final screen for the wizard for use in setting up a tool configuration for archive data restoration.

The restore operation is designed to treat the archive data as a special tool. Instead of just moving records to the main database 08, the archive database is queried for ingest data similar to parsing a tool's output file. As shown in FIG. 49, setting up a tool Config for archive data restoration is done via the tool Config screen of the Configuration Application. Clicking on "Configure New Tool" 320 activates the tool Config wizard 322. The "File Type" 324 list control includes an "Archive_Restore" selection. Selecting this type will set the extension to "zip" as shown in FIG. 50. Now in FIG. 50, clicking on "Next" 332 displays the dialog box to configure tool specific parameters. The only parameter that needs setting in the "Configure Archive/Restore Parameters" dialog box, which is displayed in FIG. 51, is the staging directory. Clicking on "Next" 332 of FIG. 51 displays the last dialog box of the wizard, shown in FIG. 52. Clicking "Finish" 334 in FIG. 52 configures the new "Archive/Restore" tool.

Multi-plant Data Management

The Data Management system of the present invention provides a capability to transfer data to another selected Integrated Data Management system, whether local or remote, in order that data from multiple sites can be compared and overall process optimized. Transmitted data may be reviewed off-line either individually or with data from other systems in order to make comparisons of production systems.

The Archive/Restore functionality described above may be used to make system data available to other sites, such as a central site. As described above, users may specify, manually or automatically a location in which to store the archived data; the location may be local or remote. Using the Archive Restoration procedure described above, the system that archived the data (or any other system having access to the location where the data are stored) may retrieve the data for additional analysis. Data for multiple production lots, multiple processes, or multiple sites may thus be combined.

Providing transfer of selected data, especially in connection with providing automatic transmission of such data, to other systems allows users easy access to data for corporate-wide quality control of multiple fabrication facilities and for efficient transfer of selected information to customers.

Figure 53:
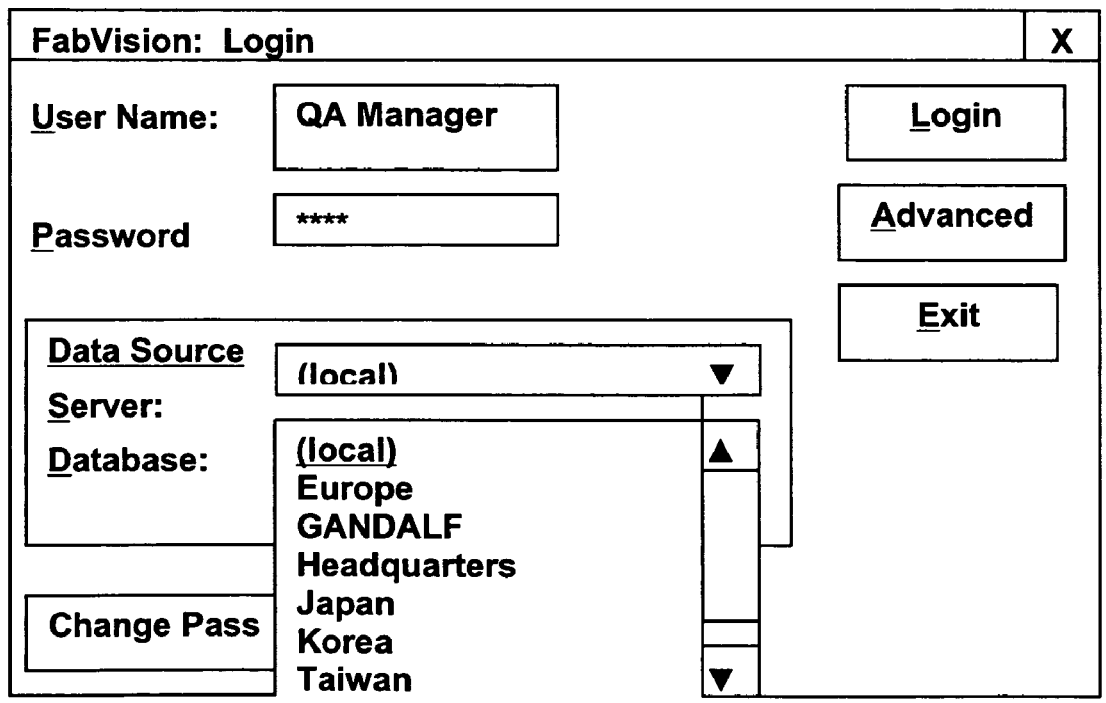
FIG. 53 is a block diagram of a screen for logging into the integrated semiconductor wafer data management, process monitoring, data analysis, and data automation system of the present invention.

Log-in: A user would log in to the integrated system in the same way as described above and shown in FIG. 53.

Figure 54:
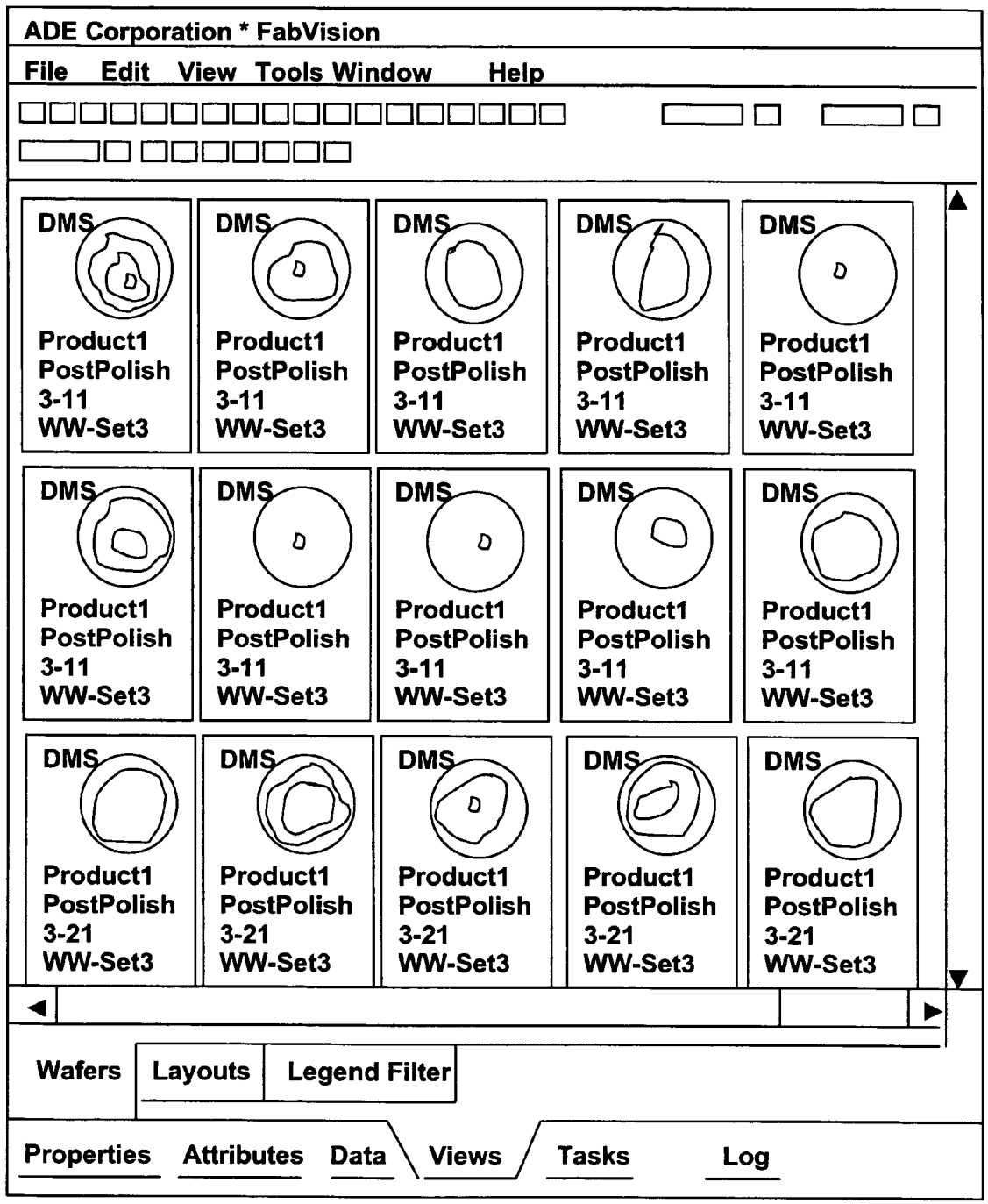
FIG. 54 is a block diagram of a screen for displaying a wafer map gallery.

Review data: Data would be reviewed either individually, such as the wafer map gallery shown in FIG. 54.

Figure 55:
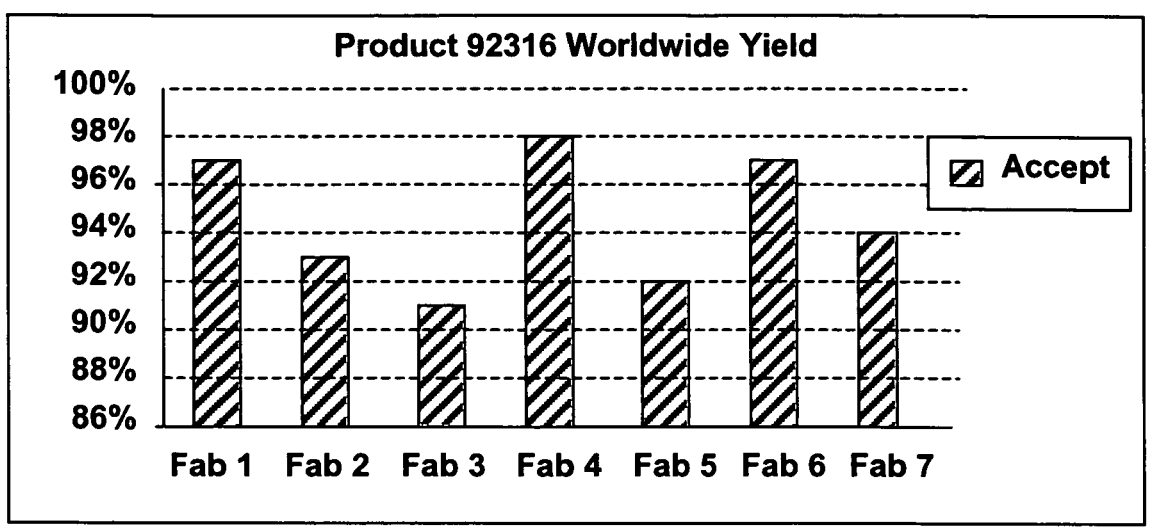
FIG. 55 is a block diagram of a screen for displaying data across fabrication sites.
Figure 56:
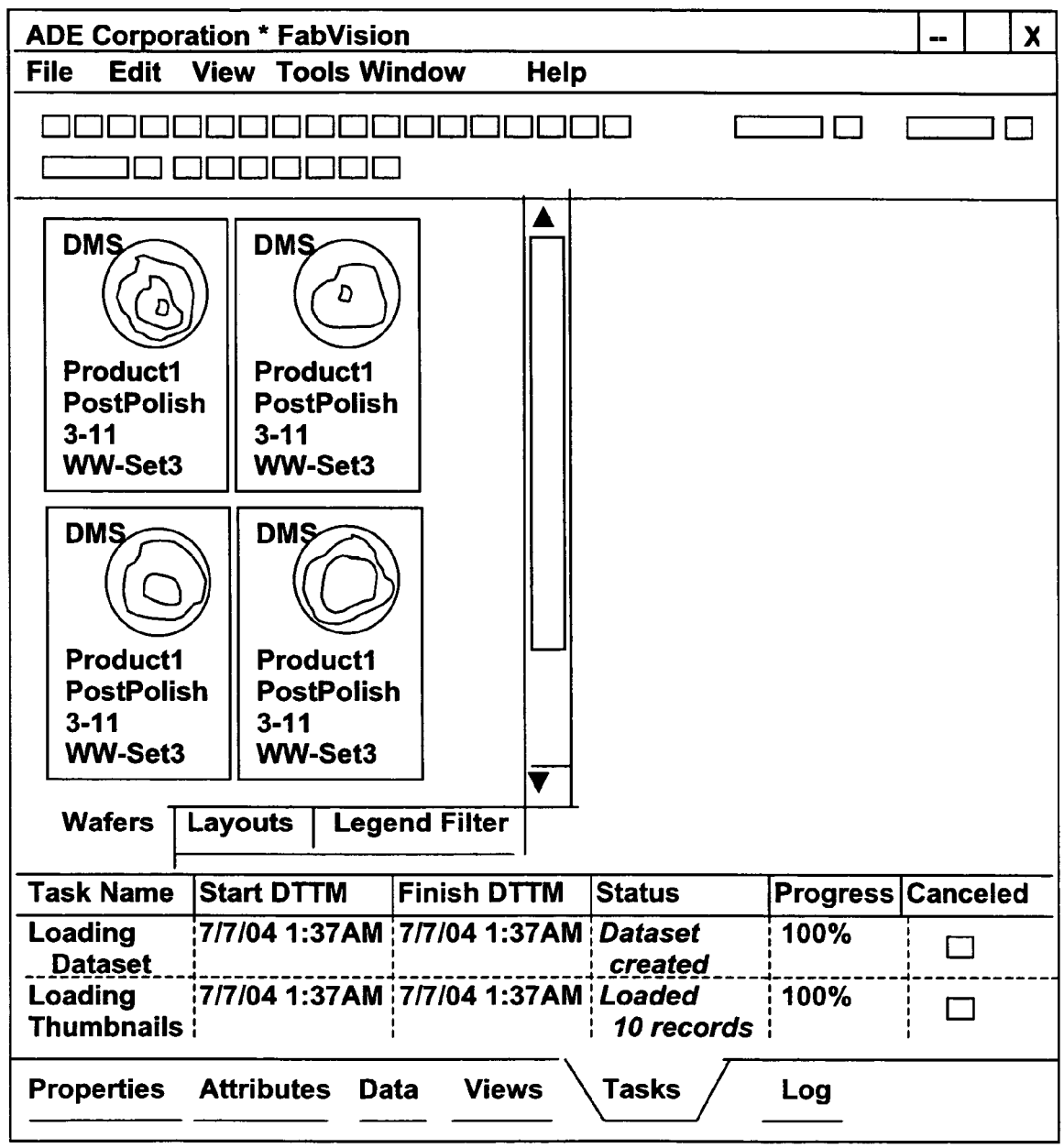
FIG. 56 is a block diagram of a first screen for displaying wafers in a wafer gallery.

Alternatively, data could be compared across fabrication sites, as shown in FIG. 55.

Autonomous Updating

Figure 57:
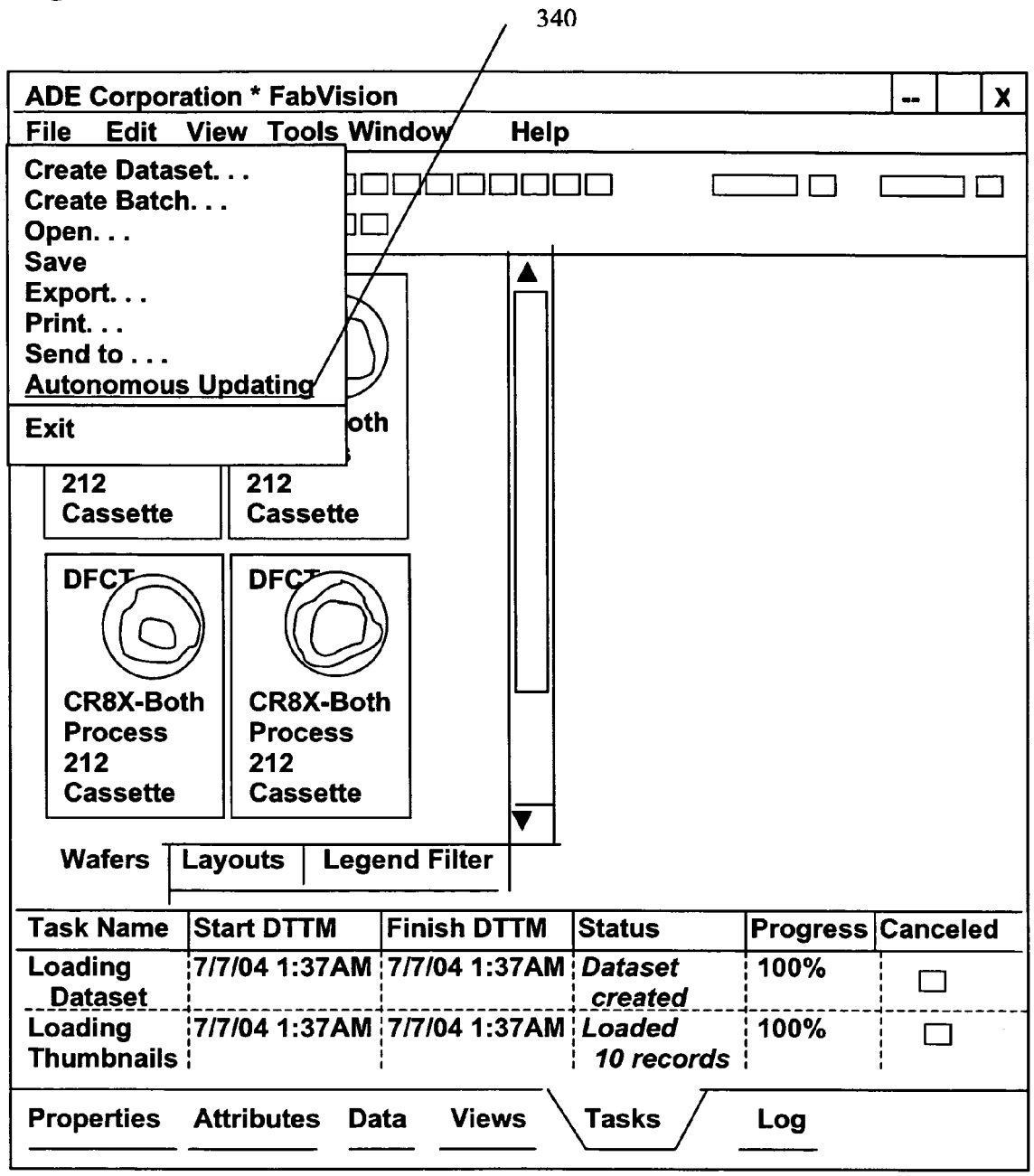
FIG. 57 is a block diagram of another screen for displaying wafers using the Autonomous Updating feature, in which Autonomous Updating feature is being invoked.

The Autonomous Updating feature allows users to configure their client station to automatically refresh at selected intervals the gallery using the last query issued. The results from the query will be displayed in the gallery (in either list or thumbnail view), sorted by date with the most recent scan at the top. The purpose of this feature is to provide the user with an automated way of seeing new scans as they come into the system. The procedure for Autonomous Updating follows:

User issues query manually and populates the gallery as shown in FIG. 57.

User Selects Autonomous Update 340 from the menu in FIG. 57.

Figure 58:
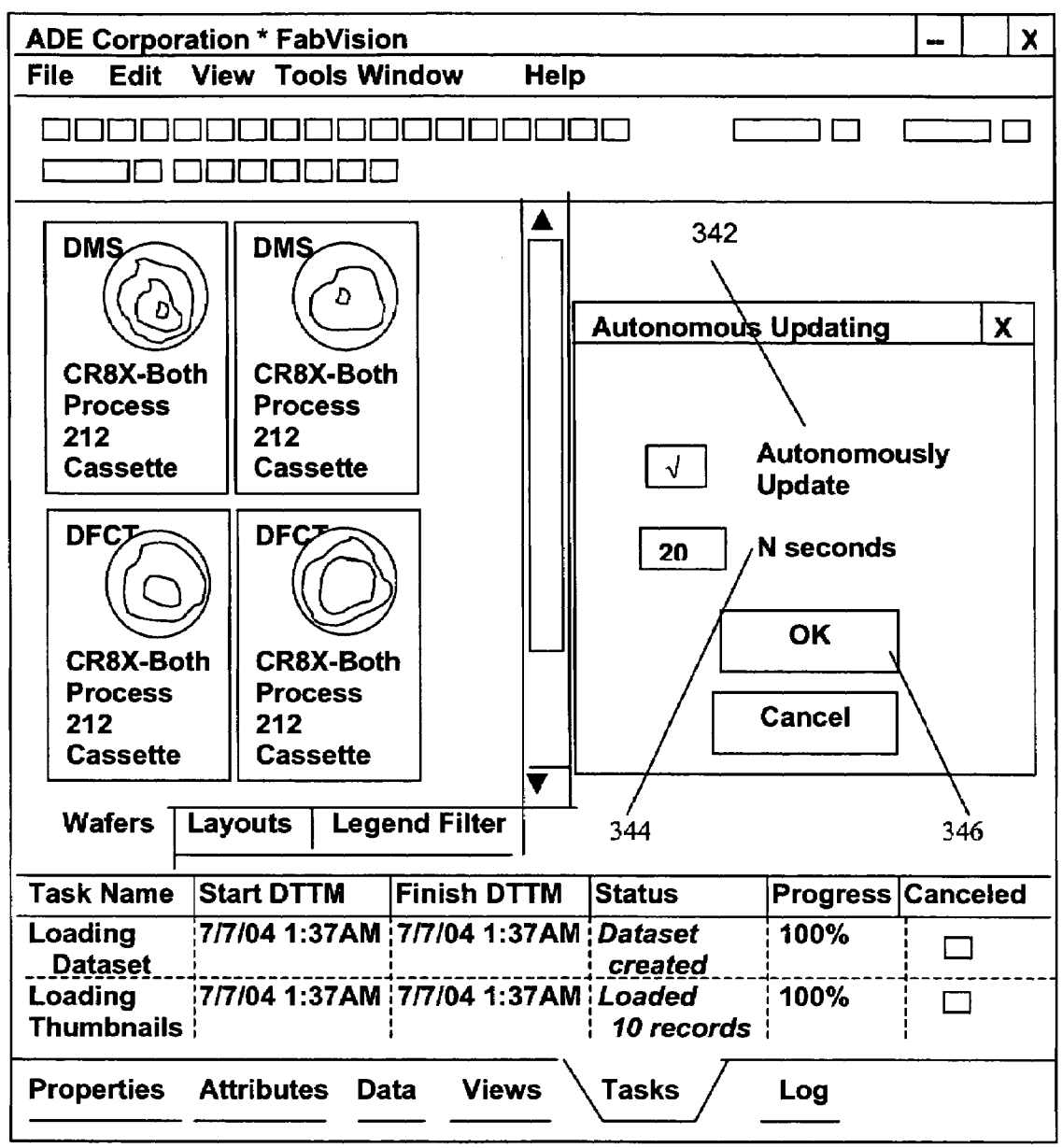
FIG. 58 is a block diagram of a screen for selecting the Autonomous Updating period of Autonomous Updating feature.

The user enables the option, as shown in FIG. 58, by checking on the box 342 and entering how many seconds 344 between updates (such as N seconds) are desired, and clicking on "OK" 346.

After OK is clicked the last query will be reissued every N seconds, allowing the user to see a constantly updating gallery.

Multiple Wafer Default Map Layout

The differences between defect and dimensional data require viewing by different layouts. Commingling defect and dimensional data in the same wafer gallery, as is done in the present invention, requires switching between the layouts. Manually selecting a layout to use each time that a user switches between defect and dimensional data can be burdensome.

The system of the present invention provides a multiple default wafer map layout feature, in which multiple wafer map layouts (at least a default dimensional and a default defect layout) may be saved as defaults so that maps of different data types may be displayed. Users may simply double click on a map in the gallery to display an alternative layout. The system keeps track of which layouts (defect or dimensional) are designated as defaults. When a user double clicks on a map in the gallery, the system determines its map type (for example, whether it is a defect or dimensional map) and assigns the appropriate layout for the map given its type. The system GUI supports multiple default wafer map functionality using the following features:

Creating a Wafer Map Layout

Figure 59:
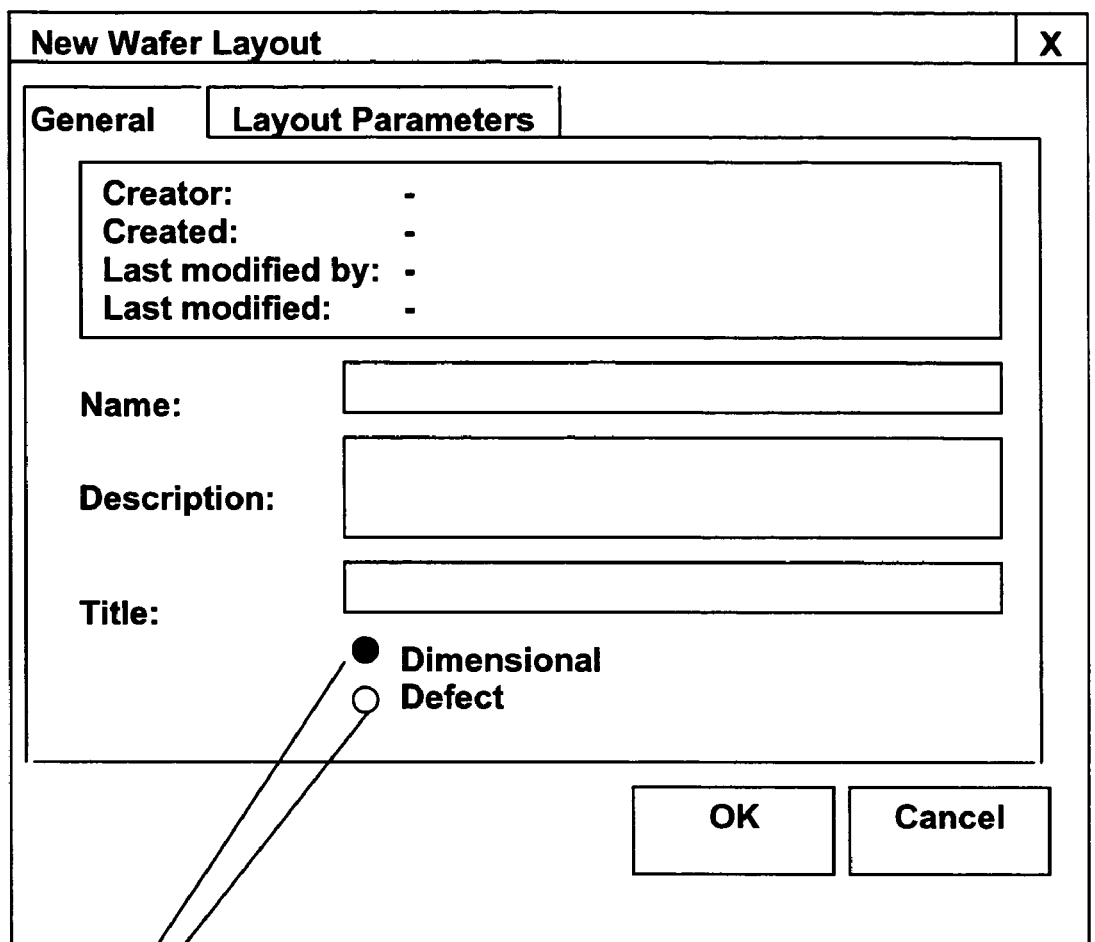
FIG. 59 is a block diagram of a New Wafer Map Layout screen for creating a new wafer map layout.

The wafer map layout creation screen shown in FIG. 59, has a field 350 to indicate the type of data for which the layout is intended. In the embodiment shown, the types are defect or dimensional data. When the user chooses the data type, thus defining the layout type, the layout parameters that apply to the selected data type are displayed in the layout definition screen.

Default Wafermap Icon

Figure 60:
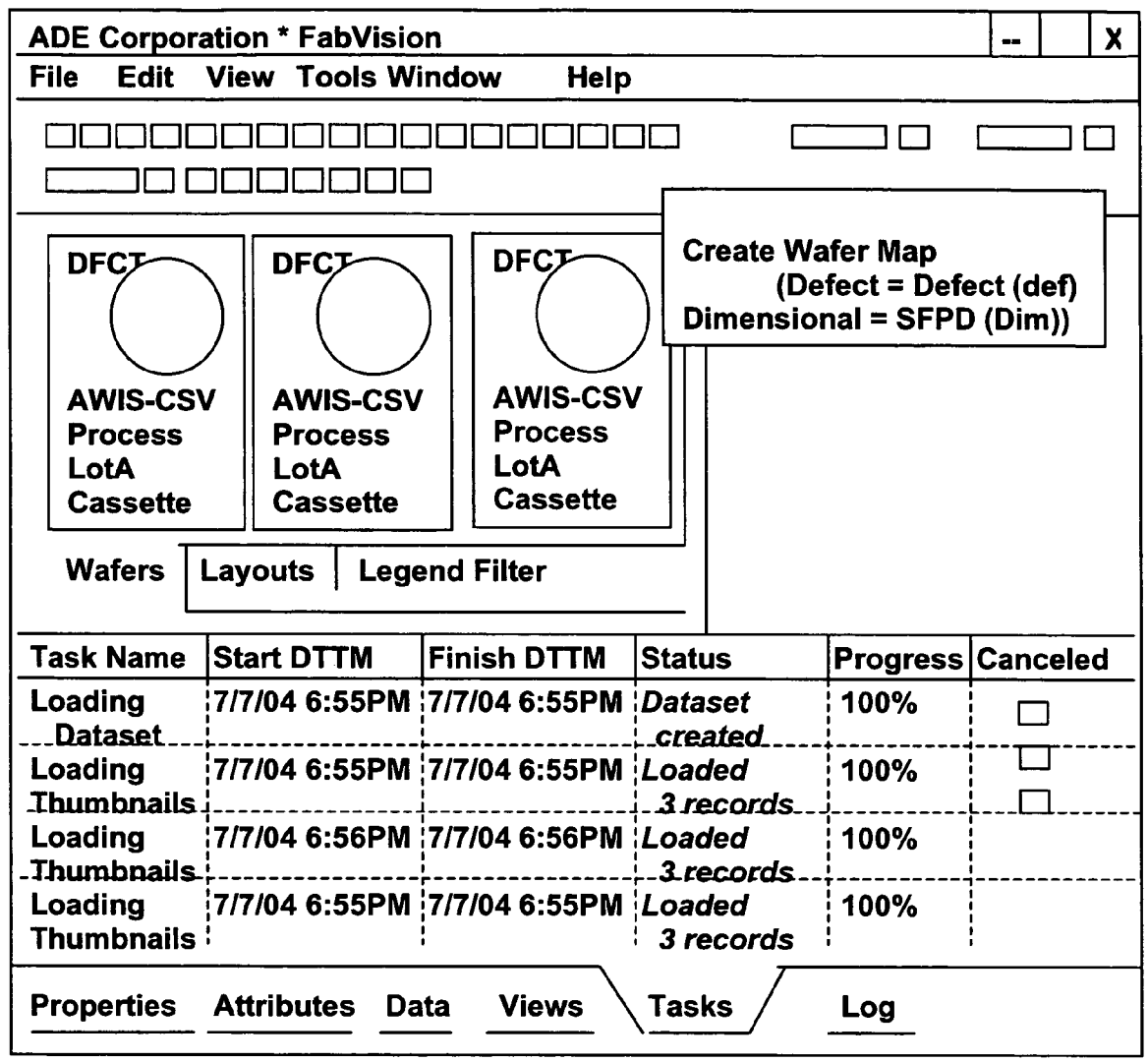
FIG. 60 is a block diagram of a Default Wafer Map Layout screen for specifying a default wafer map layout.

Referring now to FIG. 4, when the user hovers over the "default wafermap" icon on the dataset display screen, multiple layout names are displayed in the tooltip. As shown in FIG. 60, two types are displayed, one for defect and one for dimensional.

Specifying the Default Wafer Map Layout

A default wafer map layout is specified using the following process:

1. In the Utility Window 20 of FIG. 4, click the Wafers 26 tab.
2. Right-click and select Wafer Map >Set Default Layout.
3. Select one of the available wafer map layouts and click OK. An Options button is provided to allow a user to toggle the list of layouts to include only the layouts that a specific user has created or layouts created by all users.

The current default wafer map layout may be determined at any time by locating the Wafer, Map icon in the Utility Window 20's Wafers 26 tab and placing the cursor over it. A ToolTip display will report the current default wafer map layout name in parentheses.

Viewing Wafer Maps

Wafer maps may be viewed using the existing layout, or using a default layout.

Displaying a Wafer Map from the Wafers Tab Using a Selected Layout

This method selects an existing wafer map layout, then creates a wafer map using the currently selected wafers in the currently selected dataset.

1. Create a new dataset or load an existing dataset.
2. In the Utility Window 20 of FIG. 4, click the Wafers 26 tab to display the dataset.
3. Highlight the wafers of interest by clicking on individual records in an extended data wafer list or by clicking on individual thumbnails in the gallery. Use the <Shift> and <Ctrl> keys to select multiple wafers. To include all of the wafers in the dataset, right-click and select Select All.
4. Make sure the cursor is on one of the selected wafers, then right-click and select Wafer Map.
5. If multiple wafers are selected, the Composite Selected Wafers item, which may be set using a checkmark, may be set to "checked" if all of the wafers are to be combined into a single wafer map. The item may be set to "unchecked" if a separate wafer map for each wafer selected is preferred.
6. Make sure the cursor is on one of the selected wafer or wafers, then right-click and select Wafer Map>Run With Selected Layout.
7. From the list of wafer map layouts, click the desired layout and click OK. The wafer map is displayed using the selected wafer records and wafer map layout settings.

Displaying a Wafer Map from the Wafers Tab Using the Default Layout

A frequently used wafer map layout, specified as default wafer map layout as described above, may be selected for a currently selected set of wafers in the currently selected dataset, using the following procedure (which requires fewer keystrokes than the previous method and avoids having to search all of the available layouts):

1. Create a new dataset or load an existing dataset.
2. In the Utility Window 20 of FIG. 4, click the Wafers 26 tab to display the dataset.
3. Highlight the wafers of interest by clicking on individual records in the extended data wafer list or by clicking on individual thumbnails in the gallery. Use the <Shift> and <Ctrl> keys to select multiple wafers. To include all of the wafers in the dataset, right-click and select Select All.
4. Make sure the cursor is on one of the selected wafers, then right-click and select Wafer Map.
5. If multiple wafers are selected, the Composite Selected Wafers item may be set to "checked" if all of the wafers are to be combined into a single wafer map. The item may be set to "unchecked" if a separate wafer map for each wafer selected is preferred.
6. Click the Wafer Map icon above the wafer gallery or list, or make sure the cursor is on one of the selected wafers, then right-click and select Wafer Map>Run With Default Layout. The wafer map is displayed using the selected wafer records and wafer map layout settings.

It is important to note that, while the present invention has been described in the context of a fully functioning data processing system, those of ordinary skill in the art will appreciate that the processes of the present invention are capable of being distributed in the form of a computer readable medium of instructions and a variety of forms, and that the present invention applies equally regardless of the particular type of signal bearing media actually used to carry out the distribution. Examples of computer readable media include recordable-type media such as floppy discs, hard disk drives, RAM, CD-ROMs, and transmission-type media, such as digital and analog communications links.

Additionally, while the present invention has been implemented using the Windows NT™ operating system from Microsoft Corporation, and Microsoft's SQL and AccessT™ databases, those skilled in the art will appreciate that other operating systems and database management programs could be used without deviating from the spirit of the present invention.

The description of the present invention has been presented for purposes of illustration and description but is not intended to be exhaustive or limited to the invention in the form disclosed. Many modifications and variations will be apparent to those of ordinary skill in the art. This embodiment was chosen and described in order to best explain the principles of the invention, the practical application, and to enable others of ordinary skill in the art to understand the invention for various embodiments with various modifications as are suited to the particular use contemplated. Modifications of the presently disclosed invention are possible without departing from the scope of the appended claims.

The invention claimed is:

1. A system for the integrated archiving, restoring, purging, importing and exporting of semiconductor wafer data for use in silicon manufacturing and device fabrication processes, comprising:
   a network;
   a data acquisition system capable of acquiring scan data from differing types of semiconductor wafer scanning tools, the data acquisition system being capable of communicating over the network;
   a buffer system for providing temporary storage for scan data transmitted over the network from the data acquisition system and for providing fault tolerance;
   a server system for providing storage for the scan data transmitted from the buffer system over the network, the server system converting the scan data into a format used by and stored in a database management system; and
   an analysis system client station including a display and communicating with the server system over the network, the analysis system and the server system being capable of operating as a transfer manager for purging, archiving, restoring, importing and exporting scan data, wherein the analysis system comprises a composite wafer analysis module which permits scan data from multiple wafers to be overlaid into a single wafer dataset;
   wherein the transfer manager further comprises an archive and restore tool for ingesting archived scan data from a designated database and restoring it to a designated database in designated location;
   wherein the transfer manager further comprises a multi-plant data management system having the capability to transfer and share scan data between different physical sites; and
   wherein the multi-plant data management system further comprises a user specified procedure for directing the archive and restore tool to export scan data to at least one other site so that scan data from at least two sites can be reviewed for process optimization.

2. The system of claim 1, wherein the transfer manager further comprises a manual purging operation enabling a user to manually purge old scan data from the database.

3. The system of claim 1, wherein the transfer manager further comprises an automated purging operation for enabling a user to define a purge mask to determine which scan data will be purged from the database and upon what schedule.

4. The system of claim 1, wherein the transfer manager further comprises a manual archiving operating for enabling a user to manually select scan data to be archived and to designate a database and location in which it is to be stored.

5. The system of claim 1, wherein the transfer manager further comprises a manual restore operation for enabling a user to manually select archived scan data from a database to be restored to a designated database in a designated location.

6. The system of claim 1, wherein the archive and restore tool further comprises a version independent restore operation for ingesting archived scan data from a designated database as though it had been newly acquired from the data acquisition subsystem, making the restore operation independent of database version changes.

7. The system of claim 6, wherein the archive and restore tool further comprises a version independent automated restoring operation for enabling a user to define an archive mask for the archive and restore tool, the mask specifying which scan data will be restored, upon what schedule, from which database and to which database and location.

8. The system of claim 1, wherein the archive and restore tool further comprises an automated archiving operation for enabling a user to define an archive mask for the archive and restore tool, the mask specifying which scan data will be archived, upon what schedule, from which database, and to which database and location.

9. The system of claim 1, wherein the archive and restore tool further comprises an automated restoring operation for enabling a user to define an archive mask for the archive and restore tool, the mask specifying which scan data will be restored, upon what schedule, from which database and to which database and location.

10. The system of claim 1, wherein the multi-plant data management system further comprises a user specified procedure for directing the archive and restore tool to import and restore scan data from at least one other site to a central location for analysis and review, thereby enabling the central location to review scan data from a plurality of production lots, processes, and sites.

11. The system of claim 10, wherein the user specified procedure for directing the archive and restore tool to import and restore scan data further comprises parameters that can be specified for automating the importing and restoring of scan data.

12. The system of claim 1, wherein the user specified procedure for directing the archive and restore tool to export scan data further comprises parameters that can be specified for automating the exporting of scan data.

13. A method for the integrated archiving, restoring, purging, importing and exporting of semiconductor wafer data for use in silicon manufacturing and device fabrication processes, comprising the steps of:
communicating over a network;
acquiring scan data from differing types of semiconductor wafer scanning tools using a data acquisition system, the data acquisition system being capable of communicating over the communications path;
providing temporary storage and fault tolerance for scan data transmitted over the network from the data acquisition system by using a buffer system;
providing storage for the scan data transmitted from the buffer system over the network using a server system, the server system converting the scan data into a format used by and stored in a database management system; and
analyzing scan data using an analysis system client station including a display and communicating with the server system over the network, the analysis system and the server system being capable of managing the purging, archiving, restoring, importing and exporting of scan data, wherein the analysis system comprises a composite wafer analysis module which permits scan data from multiple wafers to be overlaid into a single wafer dataset;
wherein the step of managing further comprises the step of using an archive and restore tool for ingesting archived scan data from a designated database and restoring it to a designated database in a designated location;
wherein the step of managing further comprises the step of managing scan data between at least two plants using a multi-plant data management system capable of transferring and sharing scan data between different physical sites;
wherein the step of using a multi-plant data management system further comprises the step of a user directing the archive and restore tool to export scan data to at least one other site so that scan data from at least two sites can be reviewed for process optimization.

14. The method of claim 13, wherein the step of managing further comprises the step of enabling a user to manually purge old scan data from the database.

15. The method of claim 13, wherein the step of managing further comprises the step of automatically purging scan data by enabling a user to define a purge mask to determine which scan data will be purged automatically from the database and upon what schedule.

16. The method of claim 13, wherein the step of managing further comprises the step of enabling a user to manually select scan data to be archived and to designate a database and location in which it is to be stored.

17. The method of claim 13, wherein the step of managing further comprises the step of enabling a user to manually select archived scan data from a database to be restored to a designated database in a designated location.

18. The method of claim 13, wherein the step of using an archive and restore tool further comprises the step of using a version independent restore operation for ingesting archived scan data from a designated database as though it had been newly acquired from the data acquisition subsystem, making the restore operation independent of database version changes.

19. The system of claim 18, wherein the step of using an archive and restore tool further comprises the step of using a version independent automated restore operation by enabling a user to define an archive mask for the archive and restore tool, the mask specifying which scan data will be restored, upon what schedule, from which database and to which database and location.

20. The method of claim 13, wherein the step of using an archive and restore tool further comprises the step of automating an archiving operation by enabling a user to define an archive mask for the archive and restore tool, the mask specifying which scan data will be archived, upon what schedule, from which database, and to which database and location.

21. The method of claim 13, wherein the step of using an archive and restore tool further comprises the step of automating a restore operation by enabling a user to define an archive mask for the archive and restore tool, the mask specifying which scan data will be restored, upon what schedule, from which database and to which database and location.

22. The method of claim 13, wherein the step of using a multi-plant data management system further comprises the step of a user directing the archive and restore tool to import and restore scan data from at least one other site to a central location for analysis and review, thereby enabling the central location to review scan data from a plurality of production lots, processes, and sites.

23. The method of claim 22, wherein the step of directing the archive and restore tool to import and restore scan data further comprises the step of specifying parameters for automating the importing and restoring of scan data.

24. The method of claim 13, wherein the step of directing the archive and restore tool to export scan data further comprises the step of specifying parameters for automating the exporting of scan data.

25. A software program product implemented on a processor readable medium including instructions performed on a data processor for the integrated archiving, restoring, purging, importing and exporting of semiconductor wafer data for use in silicon manufacturing and device fabrication processes, the instructions comprising:

instructions for communicating over a network; instructions for acquiring scan data from differing types of semiconductor wafer scanning tools, the data acquisition system being capable of communicating over the network;

instructions for providing temporary storage and fault tolerance for scan data transmitted over the network from the data acquisition system by using a buffer system;

instructions for providing storage for the scan data transmitted from the buffer system over the network using a server system, the server system converting the scan data into a format used by and stored in a database management system;

instructions for analyzing scan data using an analysis system client station including a display and communicating with the server system over the network, the analysis system and the server system being capable of managing the purging, archiving, restoring, importing and exporting of scan data, wherein the analysis system comprises a composite wafer analysis module which permits scan data from multiple wafers to be overlaid into a single wafer dataset;

instructions for using an archive and restore tool for ingesting archived scan data from a designated database and restoring it to a designated database in a designated location;

instructions for managing scan data between at least two plants using a multi-plant data management system capable of transferring and sharing scan data between different physical sites;

instructions for directing the archive and restore tool to export scan data to at least one other site so that scan data from at least two sites can be reviewed for process optimization.

\* \* \* \* \*